(12) United States Patent
Trivedi et al.

(10) Patent No.: US 9,175,031 B2
(45) Date of Patent: *Nov. 3, 2015

(54) KETOLIDE COMPOUNDS

(75) Inventors: Bharat Trivedi, Farmington, MI (US); Prasad Deshpande, Aurangabad (IN); Ravikumar Tadiparthi, Aurangabad (IN); Sunil Gupta, Kota (IN); Santosh Diwakar, Ahmednagar (IN); Shivaji Pawar, Aurangabad (IN); Vijay Patil, Solapur (IN); Deepak Dekhane, Pune (IN); Mahesh Patel, Aurangabad (IN); Satish Bhavsar, Aurangabad (IN); Amit Mishra, Aurangabad (IN); Manish Solanki, Aurangabad (IN); Mohammad Jafri, Aligarh (IN); Sachin Bhagwat, Aurangabad (IN)

(73) Assignee: WOCKHARDT LIMITED, Chikalthana, Aurangabad O (IN)

( * ) Notice: Subject to any disclaimer, the term of this patent is extended or adjusted under 35 U.S.C. 154(b) by 66 days.

This patent is subject to a terminal disclaimer.

(21) Appl. No.: 13/991,762

(22) PCT Filed: Feb. 3, 2011

(86) PCT No.: PCT/IB2011/050464
§ 371 (c)(1),
(2), (4) Date: Sep. 17, 2013

(87) PCT Pub. No.: WO2012/076989
PCT Pub. Date: Jun. 14, 2012

(65) Prior Publication Data
US 2014/0005133 A1    Jan. 2, 2014

(30) Foreign Application Priority Data
Dec. 9, 2010   (IN) .............. 2010/MU/3352

(51) Int. Cl.
  A61K 31/70   (2006.01)
  C07H 17/08   (2006.01)
  C07H 23/00   (2006.01)
  C07D 417/04  (2006.01)
(52) U.S. Cl.
  CPC .............. C07H 17/08 (2013.01); C07D 417/04 (2013.01); C07H 23/00 (2013.01)

(58) Field of Classification Search
  CPC ...................................... C07H 17/08
  See application file for complete search history.

(56) References Cited

U.S. PATENT DOCUMENTS

| 8,541,420 B2 * | 9/2013 | Trivedi et al. ............... 514/256 |
| 2009/0075915 A1 * | 3/2009 | Kim et al. .................... 514/28 |
| 2009/0247478 A1 * | 10/2009 | Sindkhedkar et al. ......... 514/29 |

FOREIGN PATENT DOCUMENTS

| EP | 0949268 A1 | 10/1999 |
| WO | WO2008023248 A2 | 2/2008 |
| WO | WO2009137787 A1 | 11/2009 |
| WO | WO2010136971 A1 | 12/2010 |

* cited by examiner

*Primary Examiner* — Elli Peselev
(74) *Attorney, Agent, or Firm* — Bio Intellectual Property Services LLC (Bio IPS); O. (Sam) Zaghmout

(57) ABSTRACT

The invention relates to ketolide compounds of Formula (I) and their pharmaceutically acceptable salts, solvates, hydrates, polymorphs and stereoisomers having antimicrobial activity. The invention also provides pharmaceutical compositions containing the compounds of invention and methods of treating or preventing microbial infections with the compounds of invention, wherein, T is —C*H($R_1$)—P-Q; $R_1$ is hydrogen; unsubstituted or substituted lower alkyl, cycloalkyl or aryl; P is heteroaryl ring; Q is unsubstituted or substituted aryl or heteroaryl ring; and P is attached to Q via carbon-carbon link; and $R_3$ is hydrogen or fluorine, With the provision that when $R_1$ is hydrogen, $R_3$ is fluorine.

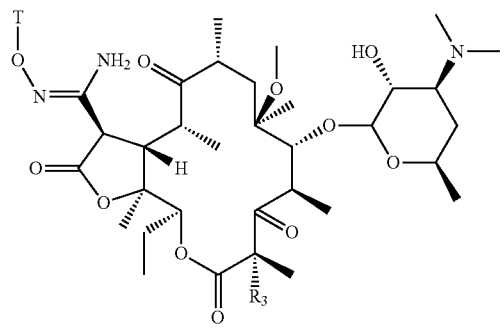

18 Claims, No Drawings

KETOLIDE COMPOUNDS

RELATED PATENT APPLICATIONS

This application claims the benefit of Indian Complete Patent Application No. 3352/MUM/2010 filed on Dec. 9, 2010, the disclosures of which are incorporated herein by reference in its entirety as if fully rewritten herein.

FIELD OF THE INVENTION

The invention relates to ketolide compounds of formula (I) and their pharmaceutically acceptable salts, solvates, hydrates, polymorphs and stereoisomers. The invention also provides pharmaceutical compositions containing these compounds and methods of treating or preventing microbial infections using these compounds.

Formula I

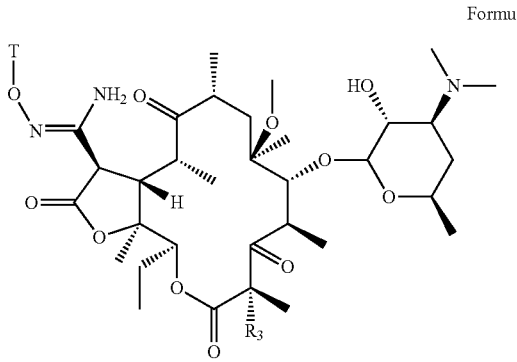

BACKGROUND OF THE INVENTION

Macrolides are a well-known family of antimicrobial agents. Erythromycin A, a 14-membered macrolide, was isolated in 1952 from *Streptomyces erythraeus*. Examples of macrolides being used as therapeutic agents are roxithromycin, clarithromycin and azithromycin (azalide). Ketolides are semisynthetic 14-membered ring macrolide derivatives, characterized by the presence of a keto function at position 3 instead of L-cladinose moiety present in the macrolactone ring. Telithromycin and Cethromycin are examples of ketolides.

U.S. Pat. No. 4,331,803 discloses the 6-O-methyl derivative of erythromycin i.e. clarithromycin. The U.S. Pat. No. 4,349,545 discloses roxithromycin. The azalide azithromycin is disclosed in U.S. Pat. No. 4,517,359. Telithromycin is described in EP 680967 A1 and corresponding U.S. Pat. No. 5,635,485 and *Bioorg. Med. Chem. Lett.* 1999, 9(21), 3075-3080. Another ketolide Cethromycin (ABT 773) is disclosed in WO 98/09978, and *J. Med. Chem.* 2000, 43, 1045.

The U.S. Pat. No. 6,900,183 describes 11,12-γ-lactone ketolides having C-21 of the lactone substituted with cyano or amino derivatives. The patent applications such as U.S. 2004/0077557 and PCT publications WO 02/16380, WO 03/42228, WO 03/072588 and WO 04/16634 disclose 11,12-γ-lactone ketolides. Our co-pending PCT publication No. WO 08/023,248 discloses several Macrolides and Ketolides.

SUMMARY OF THE INVENTION

In one general aspect, there are provided compounds of formula (I) or a pharmaceutically acceptable salt, solvate, hydrate, polymorph or stereoisomer thereof, Formula I

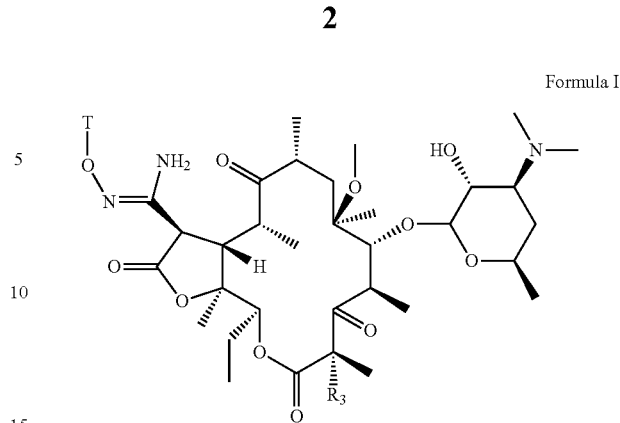

wherein,

T is —C*H(R$_1$)—P-Q;

R$_1$ is H, or unsubstituted or substituted lower alkyl, cycloalkyl or aryl;

P is heteroaryl ring;

Q is unsubstituted or substituted aryl or heteroaryl ring; and

P is attached to Q via carbon-carbon link; and

R$_3$ is hydrogen or fluorine. With proviso that when R$_1$ is H R$_3$ is fluorine;

In another general aspect, there are provided pharmaceutical compositions comprising therapeutically effective amount of a compound of formula (I) or a pharmaceutically acceptable salt, solvate, polymorph or stereoisomer thereof, optionally, with one or more pharmaceutically acceptable excipient.

In another general aspect, there is provided a method for treating or preventing microbial infection in a subject, comprising administering to a subject in need thereof a compound of formula (I) or a pharmaceutically acceptable salt, solvate, hydrate, polymorph or stereoisomer thereof.

In another general aspect, there is provided a method for treating infection caused by a microorganism in a subject, comprising administering to a subject in need thereof, a therapeutically effective amount of a compound of formula (I) or a pharmaceutically acceptable salt, solvate, hydrate, polymorph or stereoisomer thereof.

In another general aspect, there is provided a method for prophylactic treatment of a subject, comprising administering to a subject at risk of infection caused by microorganism, a prophylactically effective amount of a compound of formula (I) or a pharmaceutically acceptable salt, solvate, hydrate, polymorph or stereoisomer thereof.

In another general aspect, there is provided a method of treating infection caused by a microorganism in a subject, comprising administering to the subject in need thereof, a pharmaceutical composition comprising therapeutically effective amount of a compound of formula (I) or a pharmaceutically acceptable salt, solvate, polymorph or stereoisomer thereof, optionally with one or more pharmaceutically acceptable excipient.

In some other embodiments, there is provided a method for prophylactic treatment of a subject, comprising administering to a subject at risk of infection caused by microorganism, a pharmaceutical composition comprising therapeutically effective amount of a compound of formula (I) or a pharmaceutically acceptable salt, solvate, polymorph or stereoisomer thereof, optionally with one or more pharmaceutically acceptable excipient.

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise.

In general, the following definitions are used, unless otherwise described.

The symbol* indicates chiral center in the formula (I) which is either in the R or in S form or mixture of both forms.

The term "stereoisomer" refers to compounds, which have identical chemical composition, but differ with regard to arrangement of the atoms and the groups in space. These include enantiomers, diastereomers, geometrical isomers, atropisomer and conformational isomers. Geometric isomers may occur when a compound contains a double bond or some other feature that gives the molecule a certain amount of structural rigidity. An enantiomer is a stereoisomer of a reference molecule that is the nonsuperimposable mirror image of the reference molecule. A diastereomer is a stereoisomer of a reference molecule that has a shape that is not the mirror image of the reference molecule. An atropisomer is a conformation of a reference compound that converts to the reference compound only slowly on the NMR or laboratory time scale. Conformational isomers (or conformers or rotational isomers or rotamers) are stereoisomers produced by rotation about σ bonds, and are often rapidly interconverting at room temperature. Racemic mixtures are also encompassed within the scope of this invention. Some of the compounds of the present invention may have trans and cis isomers and geometric E- and Z- isomers. The wavy bond indicates that the compounds may be present as either of E- or Z- isomer. Also some of the compounds according to this invention may exist as diastereomers. In addition, where the process for the preparation of the compounds according to the invention give rise to mixture of stereoisomers, these isomers, may be separated by conventional techniques such as preparative chromatography and HPLC. The compounds may be prepared as a single stereoisomer or in racemic form as a mixture of some possible stereoisomer.

The term "polymorphs, solvates and hydrates" has meaning as discussed herewith. The compounds of invention may exists as different polymorphs such as crystalline or amorphous forms and as such are intended to be included in the present invention. In addition, some of the compounds may form solvates with water (i.e. hydrates), which contains various amounts of water, for instance the hydrate, hemihydrate and sesquihydrate forms. Also the compound can form solvates with common organic solvents. Such solvates and hydrates are intended to be included within the scope of this invention.

The term "lower alkyl" refers to $C_1$-$C_6$ alkyl saturated, straight or branched chain hydrocarbon radicals containing between one and six carbon atoms. Examples of $C_1$-$C_6$ alkyl radicals include but are not limited to, methyl, ethyl, propyl, butyl, pentyl, hexyl, and their branched isomers such as iso-propyl, iso-butyl or tert-butyl.

The term "cycloalkyl" refers to $C_3$-$C_6$ saturated carbocyclic radical containing between three and six carbon atoms. Examples of $C_3$-$C_6$ saturated carbocyclic radical include cyclopropyl, cyclobutyl, cyclopentyl, or cyclohexyl.

The term "substituted lower alkyl" refers to substituted $C_1$-$C_6$ alkyl, substituted by independent replacement of one or two or three of the hydrogen atoms thereon with F, Cl, Br, I, $NO_2$, $NH_2$, CN, OH, $C_1$-$C_6$ alkoxy, alkylamino, dialkylamino, mercapto, formyl, carboxy, alkoxycarbonyl and carboxamide, aryl, heteroaryl, substituted aryl, substituted heteroaryl. Examples of such substitutions are fluoromethyl, difluoromethyl, trifluoromethyl. nitromethyl, aminomethyl, cyanomethyl, hydroxymethyl and the like. Examples of $C_1$-$C_6$ alkoxy are methoxy, ethoxy, propyloxy, isopropyloxy, butyloxy, pentyloxy, hexyloxy.

The term "alkylamino" refers to a group having the structure —NH($C_1$-$C_6$ alkyl) where $C_1$-$C_6$ alkyl is as previously defined.

The term "dialkylamino" refers to a group having the structure —N($C_1$-$C_6$ alkyl) ($C_1$-$C_6$ alkyl), where $C_1$-$C_6$ alkyl is as previously defined. Examples of dialkylamino are, but not limited to, dimethylamino, diethylamino, methylethylamino and the like.

The term "aryl" refers to a mono or bicyclic ring system such as phenyl or naphthyl.

The term "heteroaryl" refers to a mono i.e. 5-6 membered or bicyclic i.e. fused aromatic ring system having at least one carbon atom of the aromatic ring replaced by an atom selected from the group of N, O, S. For example pyridyl, pyrazinyl, pyrimidinyl, pyrrolyl, pyrazolyl, imidazolyl, thiazolyl, isothiazolyl, oxazolyl, isoxazolyl, thiadiazolyl, oxadiazolyl, thienyl, triazolyl, triazinyl, furanyl, N-oxo-pyridyl, and the like. It includes the fused biaryl systems such as indolyl, quinolinyl, isoquinolinyl, benzothiazolyl, benzoxazolyl, benzothienyl, N-oxo-quinolyl, benzimidazolyl, benzopyranyl, benzoisothiazolyl, benzodiazinyl, benzofurazanyl, indazolyl, indolizinyl, benzofuryl, quinoxalinyl, pyrrolopyridinyl, furopyridinyl (such as furo[2,3-c]pyridinyl, furo[3,2-b]pyridinyl, furo[2,3-b]pyridinyl), naphthyridinyl, phthalazinyl, pyridopyridyl, quinazolinyl, thienofuryl, thienopyridyl, thienotheinyl, purinyl (such as 9H-purin-1-yl, 6-amino-9H-purin-9-yl), pyridinyl-1H-pyrazol-1-yl and the like.

The aryl or the heteroaryl group can be optionally substituted by independent replacement of one or more of hydrogen atoms thereon with substituents selected from $C_1$-$C_6$ alkyl, substituted $C_1$-$C_6$ alkyl, cyano, hydroxy, halogen, amino, formyl, carboxy, carboxamide, $C_1$-$C_6$ alkoxy, $C_1$-$C_6$ thioalkoxy, $C_1$-$C_6$ alkylcarbonyl, amino, alkylamino, dialkylamino, mercapto, nitro, carboxy, alkoxycarbonyl, aminocarbonyl, alkylthio, arylthio, heteroarylthio or haloalkyl.

The term "pharmaceutically acceptable salt" as used herein refers to one or more salts of the free base of the invention which possess the desired pharmacological activity of the free base and which are neither biologically nor otherwise undesirable. The salts are suitable for use in contact with the tissues of human and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable acid. These salts may be obtained from inorganic or organic acids. Examples of inorganic acids are hydrochloric acid, nitric acid, perchloric acid, hydrobromic acid, sulphuric acid or phosphoric acid. Examples of organic acids are acetic acid, propionic acid, oxalic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulphonic acid, p-toluene sulphonic acid, salicyclic acid and the like. Also included are the salts with various amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malonate, 2-naphthalenesulfonate, nicotinate, oleate, palmitate, pamoate, pectinate, persulfate, 3-phenylpropionate, phosphate, picrate, pivalate, propionate, stearate, sulfate, tartrate, thiocyanate, p-toluenesulfonate, undecanoate, valerate salts, and the like.

Salt of an acid moiety in the compound can also be prepared by reacting with a suitable base. These suitable salts are furthermore those of the inorganic or organic bases. Inorganic bases such as KOH, NaOH, Ca(OH)$_2$, Al(OH)$_3$. The organic base salts from basic amines such as ethylamine, triethylamine, diethanolamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "therapeutically effective amount" means that amount of compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent(s) needed to elicit the biological or medicinal response will depend on a number of factors, including but not limited to the disease or disorder being treated, the active compound(s) or pharmaceutical agent(s) being administered, the method of administration, and the condition of the patient.

The term "treat", "treating" or "treatment" as used herein refers to administering a pharmaceutical composition or a compound for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. Thus, in preferred embodiments, treating is the administration to a subject (either for therapeutic or prophylactic purposes) of therapeutically effective amount of compound of formula (I) or a pharmaceutically acceptable salt, solvate, polymorph or stereoisomer thereof.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "microorganism" or "microbe" as used herein includes bacteria, fungi, protozoa, yeast, mold, and mildew.

The term "infection" as used herein includes presence of a microorganism in or on a subject, which, if its growth were inhibited, would result in a benefit to the subject. As such, the term "infection" in addition to referring to the presence of microorganisms also refers to normal flora, which are not desirable. The term "infection" includes infection caused by bacteria, fungi, protozoa, yeast, mold, or mildew.

Typical, non-limiting examples of infections include those such as pneumonia, otitis media, sinusitus, bronchitis, tonsilitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C-F (minute-colony streptococci), viridans streptococci, *Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory diseases related to infection by *P. haem., P. multocida, Mycoplasma bovis*, or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius*, coagulase neg. *Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*.

In one general aspect, there are provided compounds of formula (I) or a pharmaceutically acceptable salt, solvate, hydrate, polymorph or stereoisomer thereof, Formula I

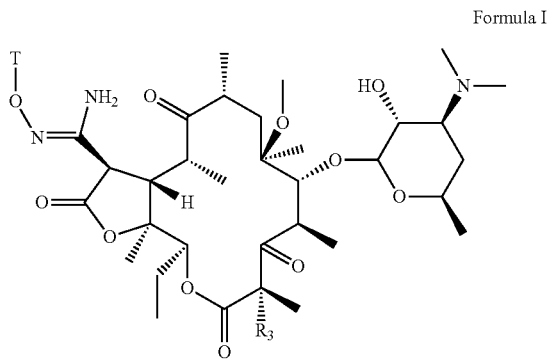

wherein,
T is —C*H($R_1$)—P-Q;
$R_1$ is hydrogen; unsubstituted or substituted lower alkyl, cycloalkyl or aryl;
P is heteroaryl ring;
Q is unsubstituted or substituted aryl or heteroaryl ring; and
P is attached to Q via carbon-carbon link; and
$R_3$ is hydrogen or fluorine,
With the provision that when $R_1$ is hydrogen, $R_3$ is fluorine.

In some embodiments, there are provided compounds of formula (I), wherein:
T is —C*H($R_1$)—P-Q;
$R_1$ is hydrogen;
$R_3$ is fluorine,
P is 5 or 6-membered heteroaryl ring with up to three heteroatoms;
Q is unsubstituted or substituted aryl or 5 or 6-membered heteroaryl ring; and
P is attached to Q via carbon-carbon link In some embodiments, there are provided compounds of formula (I), wherein:
T is —C*H($R_1$)—P-Q;
$R_1$ is hydrogen;
$R_3$ is fluorine,
P is 5 or 6-membered heteroaryl ring with up to three heteroatoms;
Q is unsubstituted or substituted aryl or 5 or 6-membered heteroaryl ring with up to two nitrogens; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is 5-membered heteroaryl ring such as isoxazole or thiadiazole;
Q is unsubstituted or substituted aryl or 6-membered heteroaryl ring with up to two nitrogens; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is 6-membered heteroaryl ring such as pyridine or pyrimidine;
Q is unsubstituted or substituted aryl or 5 or 6-membered heteroaryl ring with up to two heteroatoms; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is 5-membered heteroaryl ring such as isoxazole or thiadiazole;
Q is unsubstituted or substituted pyridine or pyrimidine; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is thiadiazole;
Q is unsubstituted or substituted pyridine or pyrimidine; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is isoxazole;
Q is unsubstituted or substituted pyridine or pyrimidine; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is thiadiazole;
Q is pyridine or pyrimidine; and
P is attached to Q via carbon-carbon link.

In some embodiments, there are provided compounds of formula (I), wherein:
T is —C*H($R_1$)—P-Q;
$R_1$ is hydrogen;
$R_3$ is fluorine,
P is isoxazole;
Q is pyridine or pyrimidine; and
P is attached to Q via carbon-carbon link.

In some embodiments, there are provided compounds of formula (I), wherein:
T is —C*H(R$_1$)—P-Q;
R$_1$ is hydrogen;
R$_3$ is fluorine,
P is pyrimidine;
Q is unsubstituted or substituted 5-membered heteroaryl; and
P is attached to Q via carbon-carbon link.

In some embodiments, there are provided compounds of formula (I), wherein:
T is —C*H(R$_1$)—P-Q;
R$_1$ is hydrogen;
R$_3$ is fluorine,
P is pyrimidine;
Q is isoxazole; and
P is attached to Q via carbon-carbon link.

In some embodiments, there are provided compounds of formula (I), wherein:
T is —C*H(R$_1$)—P-Q;
R$_1$ is unsubstituted or substituted lower alkyl, cycloalkyls, or aryl;
P is heteroaryl ring;
Q is unsubstituted or substituted aryl or heteroaryl ring; and
P is attached to Q via carbon-carbon link; and
R$_3$ is hydrogen or fluorine.

In some embodiments, there are provided compounds of formula (I), wherein:
T is —C*H(R$_1$)—P-Q;
R$_1$ is unsubstituted or substituted lower alkyl;
P is heteroaryl ring;
Q is unsubstituted or substituted aryl or heteroaryl ring; and
P is attached to Q via carbon-carbon link; and
R$_3$ is hydrogen or fluorine In some embodiments, there are provided compounds of formula (I), wherein:
T is —C*H(R$_1$)—P-Q;
R$_1$ is unsubstituted or substituted lower alkyl;
P is 5-membered heteroaryl ring with up to three heteroatoms;
Q is unsubstituted or substituted aryl or heteroaryl ring; and
P is attached to Q via carbon-carbon link; and
R$_3$ is hydrogen or fluorine In some embodiments, there are provided compounds of formula (I), wherein:
T is —C*H(R$_1$)—P-Q;
R$_1$ is unsubstituted or substituted lower alkyl;
P is 5-membered heteroaryl ring with up to three heteroatoms;
Q is unsubstituted or substituted aryl or heteroaryl ring with up to two nitrogens; and
P is attached to Q via carbon-carbon link; and
R$_3$ is hydrogen or fluorine.

In some embodiments, there are provided compounds of formula (I), wherein:
T is —C*H(R$_1$)—P-Q;
R$_1$ is methyl;
P is 5-membered heteroaryl ring with up to three heteroatoms;
Q is unsubstituted or substituted aryl or heteroaryl ring with up to two nitrogens; and
P is attached to Q via carbon-carbon link; and
R$_3$ is hydrogen or fluorine.

In some embodiments, there are provided compounds of formula (I), wherein:
T is —C*H(R$_1$)—P-Q;
R$_1$ is methyl;
P is 5-membered heteroaryl ring such as isoxazole or thiadiazole;
Q is unsubstituted or substituted aryl or heteroaryl ring with up to two nitrogens; and
P is attached to Q via carbon-carbon link; and
R$_3$ is hydrogen or fluorine.

In some embodiments, there are provided compounds of formula (I), wherein:
T is —C*H(R$_1$)—P-Q;
R$_1$ is methyl;
P is 5-membered heteroaryl ring such as isoxazole or thiadiazole;
Q is pyridine or pyrimidine; and
P is attached to Q via carbon-carbon link; and
R$_3$ is hydrogen or fluorine.

In some embodiments, there are provided compounds of formula (I), wherein:
T is —C*H(R$_1$)—P-Q;
R$_1$ is methyl;
P is thiadiazole;
Q is pyridine or pyrimidine; and
P is attached to Q via carbon-carbon link; and
R$_3$ is hydrogen or fluorine.

In some embodiments, there are provided compounds of formula (I), wherein:
T is —C*H(R$_1$)—P-Q;
R$_1$ is methyl;
P is isoxazole;
Q is pyridine or pyrimidine; and
P is attached to Q via carbon-carbon link; and
R$_3$ is hydrogen or fluorine.

In some other embodiments, there is provided a compound or a pharmaceutically acceptable salt, solvate, hydrate, polymorph or stereoisomer thereof, selected from:
a compound of formula (I) wherein T is [3-(pyrimidin-2-yl)-isoxazol-5-yl]-CH$_2$— and R$_3$ is F;
a compound of formula (I) wherein T is [5-(isoxazol-3-yl)-pyrimidin-2-yl]-CH$_2$— and R$_3$ is F;
a compound of formula (I) wherein T is [5-(pyrimidin-2-yl)-isoxazol-3-yl]-CH$_2$— and R$_3$ is F;
a compound of formula (I) wherein T is [5-(2-amino-pyridin-6-yl)-isoxazol-3-yl]-CH$_2$— and R$_3$ is F;
a compound of formula (I) wherein T is [5-(pyridin-2-yl)-isoxazol-3-yl]-CH$_2$— and R$_3$ is F;
a compound of formula (I) wherein T is [2-(2-amino-pyridin-6-yl)-1,3,4-thiadiazol-5-yl]-CH$_2$— and R$_3$ is F;
a compound of formula (I) wherein T is [2-(pyrimidin-2-yl)-1,3,4-thiadiazol-5-yl]-CH$_2$— and R$_3$ is F;
a compound of formula (I) wherein T is [2-(2-amino-pyridin-5-yl)-1,3,4-thiadiazol-5-yl]-CH$_2$— and R$_3$ is F;
a compound of formula (I) wherein T is [2-(pyridin-2-yl)-1,3,4-thiadiazol-5-yl]-CH$_2$— and R$_3$ is F;
a compound of formula (I) wherein T is [5-(pyrazin-2-yl)-isoxazol-3-yl]-CH$_2$— and R$_3$ is F; a compound of formula (I) wherein T is [2-(6-amino-pyrimidin-2-yl)-1,3,4-thiadiazol-5-yl]-CH$_2$ and R$_3$ is F—;
a compound of formula (I) wherein T is [2-(3-amino-phenyl)-1,3,4-thiadiazol-5-yl]-CH$_2$— and R$_3$ is F;
a compound of formula (I) wherein T is [2-(2-amino-pyridin-6-yl)-pyridin-6-yl]-CH$_2$— and R$_3$ is F;
a compound of formula (I) wherein T is [5-(6-amino-pyrimidin-2-yl)-isoxazol-3-yl]-CH$_2$— and R$_3$ is F;

a compound of formula (I) wherein T is (RS)-[2-(pyridin-2-yl)-1,3,4-thiadiazol-5-yl]-CH(CH$_3$)— and R$_3$ is H;

a compound of formula (I) wherein T is (R)-[2-(pyridin-2-yl)-1,3,4-thiadiazol-5-yl]-CH(CH$_3$)— and R$_3$ is H;

a compound of formula (I) wherein T is (S)-[2-(pyridin-2-yl)-1,3,4-thiadiazol-5-yl]-CH(CH$_3$)— and R$_3$ is H;

a compound of formula (I) wherein T is (RS)-[3-(pyridin-2-yl)-isoxazol-5-yl]-CH(CH$_3$)— and R$_3$ is H;

a compound of formula (I) wherein T is (R)-[3-(pyridin-2-yl)-isoxazol-5-yl]-CH(CH$_3$)— and R$_3$ is H;

a compound of formula (I) wherein T is (S)-[3-(pyridin-2-yl)-isoxazol-5-yl]-CH(CH$_3$)— and R$_3$ is H;

a compound of formula (I) wherein T is (RS)-[5-(pyrimidin-2-yl)-isoxazol-3-yl]-CH(CH$_3$)— and R$_3$ is H;

a compound of formula (I) wherein T is (R)-[5-(pyrimidin-2-yl)-isoxazol-3-yl]-CH(CH$_3$)— and R$_3$ is H;

a compound of formula (I) wherein T is (S)-[5-(pyrimidin-2-yl)-isoxazol-3-yl]-CH(CH$_3$)— and R$_3$ is H;

a compound of formula (I) wherein T is (R)-[5-(pyridin-2-yl)-isoxazol-3-yl]-CH(CH$_3$)— and R$_3$ is H;

a compound of formula (I) wherein T is (S)-[5-(pyridin-2-yl)-isoxazol-3-yl]-CH(CH$_3$)— and R$_3$ is H;

a compound of formula (I) wherein T is (R)-[5-(pyridin-2-yl)-isoxazol-3-yl]-CH(C$_2$H$_5$)— and R$_3$ is H;

a compound of formula (I) wherein T is (S)-[5-(pyridin-2-yl)-isoxazol-3-yl]-CH(C$_2$H$_5$)— and R$_3$ is H;

a compound of formula (I) wherein T is (RS)-[2-(pyrimidin-2-yl)-1,3,4-thiadiazol-5-yl]-CH(CH$_3$)— and R$_3$ is H;

a compound of formula (I) wherein T is (R)-[2-(pyrimidin-2-yl)-1,3,4-thiadiazol-5-yl]-CH(CH$_3$)— and R$_3$ is H;

a compound of formula (I) wherein T is (S)-[2-(pyrimidin-2-yl)-1,3,4-thiadiazol-5-yl]-CH(CH$_3$)— and R$_3$ is H;

a compound of formula (I) wherein T is (S)-[2-(2-aminopyridin-6-yl)-1,3,4-thiadiazol-5-yl]-CH(CH$_3$)— and R$_3$ is H;

a compound of formula (I) wherein T is (R)-[2-(2-aminopyridin-6-yl)-1,3,4-thiadiazol-5-yl]-CH(CH$_3$)— and R$_3$ is H;

a compound of formula (I) wherein T is (RS)-[2-(2-aminopyridin-5-yl)-1,3,4-thiadiazol-5-yl]-CH(CH$_3$)— and R$_3$ is H;

a compound of formula (I) wherein T is (S)-[2-(2-aminopyridin-5-yl)-1,3,4-thiadiazol-5-yl]-CH(CH$_3$)— and R$_3$ is H;

a compound of formula (I) wherein T is (R)-[2-(2-aminopyridin-5-yl)-1,3,4-thiadiazol-5-yl]-CH(CH$_3$)— and R$_3$ is H;

a compound of formula (I) wherein T is (RS)-[2-(pyrazin-2-yl)-1,3,4-thiadiazol-5-yl]-CH(CH$_3$)— and R3 is H;

a compound of formula (I) wherein T is (R)-[2-(pyrazin-2-yl)-1,3,4-thiadiazol-5-yl]-CH(CH$_3$)— and R$_3$ is H;

a compound of formula (I) wherein T is (S)-[2-(pyrazin-2-yl)-1,3,4-thiadiazol-5-yl]-CH(CH$_3$)— and R$_3$ is H;

a compound of formula (I) wherein T is (RS)-[2-(pyridin-2-yl)-1,3,4-oxadiazol-5-yl]-CH(CH$_3$)— and R$_3$ is H;

a compound of formula (I) wherein T is (S)-[2-(3-aminophenyl)-1,3,4-thiadiazol-5-yl]-CH(CH$_3$)— and 3 is H;

a compound of formula (I) wherein T is (S)-[2-(2-hydroxypyridin-6-yl)-1,3,4-thiadiazol-5-yl]-CH(CH$_3$)— and R$_3$ is H;

a compound of formula (I) wherein T is (S)-[5-(isoxazol-3-yl)-pyrimidin-2-yl]-CH(CH$_3$)— and R$_3$ is H;

a compound of formula (I) wherein T is (S)-[5-(2-aminopyridin-6-yl)-isoxazol-3-yl]-CH(CH$_3$)— and R$_3$ is H;

a compound of formula (I) wherein T is (S)-[2-(4-hydroxypyridin-6-yl)-1,3,4-thiadiazol-5-yl]-CH(CH$_3$)— and R$_3$ is H;

a compound of formula (I) wherein T is (R)-[2-(pyridin-2-yl)-1,3,4-thiadiazol-5-yl]-CH(CH$_2$OH)— and R$_3$ is H;

a compound of formula (I) wherein T is (S)-[2-(pyridin-2-yl)-1,3,4-thiadiazol-5-yl]-CH(CH$_2$OH)— and R$_3$ is H;

a compound of formula (I) wherein T is (RS)-[2-(pyridin-2-yl)-1,3,4-thiadiazol-5-yl]-CH(C$_2$H$_5$)— and R$_3$ is H;

a compound of formula (I) wherein T is (S)-[2-(pyridin-2-yl)-1,3,4-thiadiazol-5-yl]-CH(C$_2$H$_5$)— and R$_3$ is H;

a compound of formula (I) wherein T is (R)-[2-(pyridin-2-yl)-1,3,4-thiadiazol-5-yl]-CH(C$_2$H$_5$)— and R$_3$ is H;

a compound of formula (I) wherein T is (S)-[2-(pyridin-2-yl)-1,3,4-thiadiazol-5-yl]-CH(CH$_3$)— and R$_3$ is F;

a compound of formula (I) wherein T is (R)-[2-(2-aminopyridin-6-yl)-1,3,4-thiadiazol-5-yl]-CH(CH$_3$)— and R$_3$ is F;

a compound of formula (I) wherein T is (S)-[2-(2-aminopyridin-6-yl)-1,3,4-thiadiazol-5-yl]-CH(CH$_3$)— and R$_3$ is F;

a compound of formula (I) wherein T is (S)-[2-(pyrimidin-2-yl)-1,3,4-thiadiazol-5-yl]-CH(CH$_3$)— and R$_3$ is F;

a compound of formula (I) wherein T is (S)-[2-(pyrazin-2-yl)-1,3,4-thiadiazol-5-yl]-CH(CH$_3$)— and R$_3$ is F;

a compound of formula (I) wherein T is (S)-[5-(pyrimidin-2-yl)-isoxazol-3-yl]-CH(CH$_3$)— and R$_3$ is F;

a compound of formula (I) wherein T is (S)-[2-(3-aminophenyl)-1,3,4-thiadiazol-5-yl]-CH(CH$_3$)— and R$_3$ is F;

a compound of formula (I) wherein T is (S)-[5-(pyridin-2-yl)-isoxazol-3-yl]-CH(CH$_3$)— and R$_3$ is F;

a compound of formula (I) wherein T is (S)-[5-(isoxazol-3-yl)-pyrimidin-2-yl]-CH(CH$_3$)— and R$_3$ is F;

a compound of formula (I) wherein T is (R)-[5-(isoxazol-3-yl)-pyrimidin-2-yl]-CH(CH$_3$)— and R$_3$ is F; and a compound of formula (I) wherein T is (S)-[5-(2-aminopyridin-6-yl)-isoxazol-3-yl]-CH(CH$_3$)— and R$_3$ is F.

In some other embodiments, there is provided a compound or a pharmaceutically acceptable salt, solvate, hydrate, polymorph or stereoisomer thereof, selected from:

a compound of formula (I) wherein T is [5-(isoxazol-3-yl)-pyrimidin-2-yl]-CH$_2$— and R$_3$ is F;

a compound of formula (I) wherein T is [2-(pyrimidin-2-yl)-1,3,4-thiadiazol-5-yl]-CH$_2$— and R$_3$ is F;

a compound of formula (I) wherein T is (S)-[2-(pyridin-2-yl)-1,3,4-thiadiazol-5-yl]-CH(CH$_3$)— and R$_3$ is H;

a compound of formula (I) wherein T is (S)-[2-(pyrimidin-2-yl)-1,3,4-thiadiazol-5-yl]-CH(CH$_3$)— and R$_3$ is H;

a compound of formula (I) wherein T is (S)-[2-(2-aminopyridin-6-yl)-1,3,4-thiadiazol-5-yl]-CH(CH$_3$)— and R$_3$ is H;

a compound of formula (I) wherein T is (S)-[2-(2-aminopyridin-5-yl)-1,3,4-thiadiazol-5-yl]-CH(CH$_3$)— and R$_3$ is H;

a compound of formula (I) wherein T is (S)-[5-(isoxazol-3-yl)-pyrimidin-2-yl]-CH(CH$_3$)— and R$_3$ is H;

a compound of formula (I) wherein T is (S)-[2-(pyridin-2-yl)-1,3,4-thiadiazol-5-yl]-CH(CH$_2$OH)— and R$_3$ is H;

a compound of formula (I) wherein T is (S)-[2-(pyridin-2-yl)-1,3,4-thiadiazol-5-yl]-CH(C$_2$H$_5$)— and R$_3$ is H;

a compound of formula (I) wherein T is (S)-[2-(pyridin-2-yl)-1,3,4-thiadiazol-5-yl]-CH(CH$_3$)— and R$_3$ is F;

a compound of formula (I) wherein T is (S)-[2-(2-aminopyridin-6-yl)-1,3,4-thiadiazol-5-yl]-CH(CH$_3$)— and R$_3$ is F;

a compound of formula (I) wherein T is (S)-[2-(pyrimidin-2-yl)-1,3,4-thiadiazol-5-yl]-CH(CH$_3$)— and R$_3$ is F;

a compound of formula (I) wherein T is (S)-[2-(3-aminophenyl)-1,3,4-thiadiazol-5-yl]-CH(CH$_3$)— and R$_3$ is F;

a compound of formula (I) wherein T is (S)-[5-(isoxazol-3-yl)-pyrimidin-2-yl]-CH(CH$_3$)— and R$_3$ is F; and a compound of formula (I) wherein T is (S)-[5-(2-aminopyridin-6-yl)-isoxazol-3-yl]-CH(CH$_3$)— and R$_3$ is F.

In some embodiments, there are provided compounds of formula (I), wherein:

Formula I

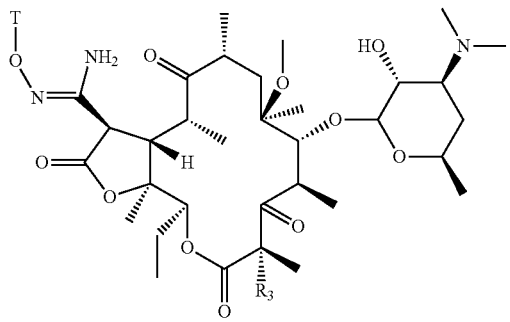

T is —C*H($R_1$)—P-Q;
$R_1$ is hydrogen;
$R_3$ is fluorine,
P is 1,3,4-thiadiazole or pyrimidine;
Q is pyrimidine-2-yl or isoxazole-3-yl; and
P is attached to Q via carbon-carbon link.

In some other embodiments, there is provided a compound or a pharmaceutically acceptable salt, solvate, hydrate, polymorph or stereoisomer thereof, selected from:

(11S,21R)-3-decladinosyl-11,12-dideoxy-2-fluoro-6-O-methyl-3-oxo-12,11-{oxycarbonyl-[E-N-[(5-pyrimidin-2-yl-1,3,4-thiadiazol-2-yl)-methoxy]-carboxamidino]methylene}-erythromycin A;

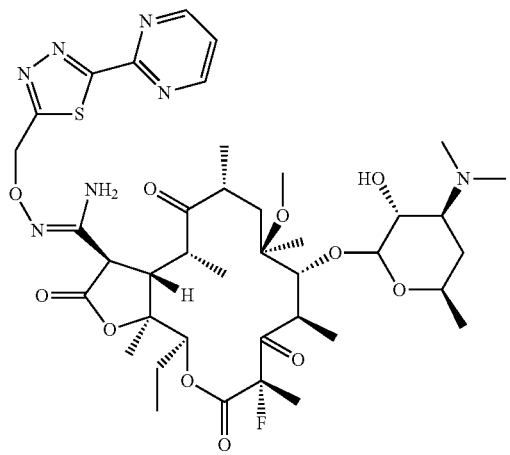 [SMILES: CC[C@@H]1OC(=O)[C@@](C)(F)C(=O)[C@H](C)[C@@H](OC2O[C@H](C)C[C@H](N(C)C)[C@H]2O)[C@](C)(OC)C[C@@H](C)C(=O)[C@H](C)[C@H]2[C@H](/C(N)=N/OCc3nnc(-c4ncccn4)s3)C(=O)O[C@@]21C]

(11S,21R)-3-decladinosyl-11,12-dideoxy-2-fluoro-6-O-methyl-3-oxo-12,11-{oxycarbonyl-[E-N-[(5-isoxazol-3-yl-pyrimidin-2-yl)-methoxy]-carboxamidino]methylene}-erythromycin A.

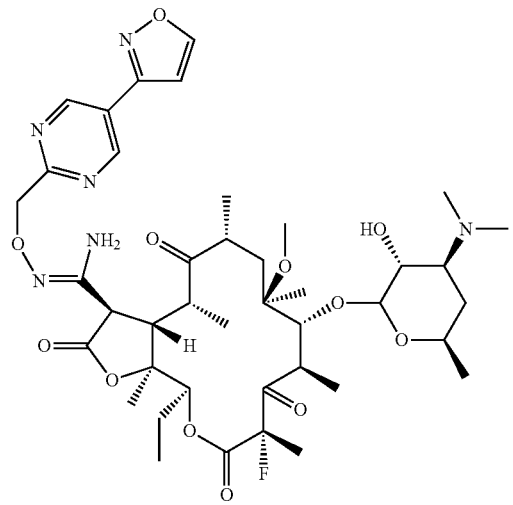 [SMILES: CC[C@@H]1OC(=O)[C@@](C)(F)C(=O)[C@H](C)[C@@H](OC2O[C@H](C)C[C@H](N(C)C)[C@H]2O)[C@](C)(OC)C[C@@H](C)C(=O)[C@H](C)[C@H]2[C@H](/C(N)=N/OCc3ncc(-c4ccon4)cn3)C(=O)O[C@@]21C]

In some embodiments, there are provided compounds of formula (I), wherein:

Formula I

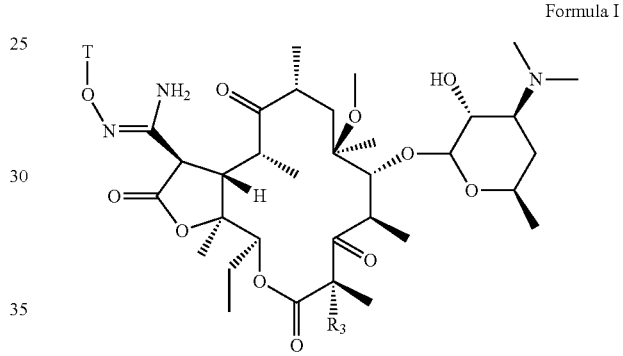

T is —C*H($R_1$)—P-Q;
$R_1$ is methyl;
P is 1,3,4-thiadiazole;
Q is pyridine-2-yl or pyrimidin-2-yl; and
P is attached to Q via carbon-carbon link; and
$R_3$ is hydrogen.

In some other embodiments, there is provided a compound or a pharmaceutically acceptable salt, solvate, hydrate, polymorph or stereoisomer thereof, selected from:

(11S,21R)-3-decladinosyl-11,12-dideoxy-6-O-methyl-3-oxo-12,11-{oxycarbonyl-[E-N-[1-(5-pyridin-2-yl-1,3,4-thiadiazol-2-yl)-(S)-ethoxy]-carboxamidino]methylene}-erythromycin A;

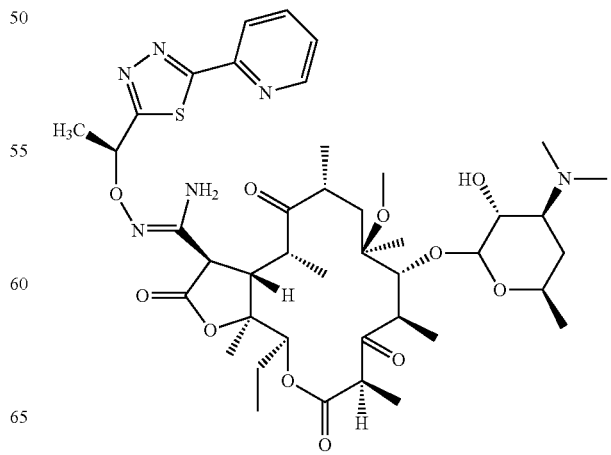

(11S,21R)-3-decladinosyl-11,12-dideoxy-6-O-methyl-3-oxo-12,11-{oxycarbonyl-[E-N-[1-(5-pyrimidin-2-yl-1,3,4-thiadiazol-2-yl)-(S)-ethoxy]-carboxamidino]methylene}-erythromycin A.

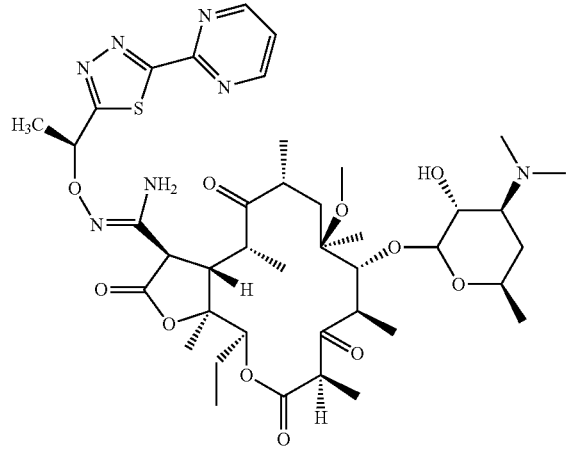 [SMILES: CC[C@@H]1OC(=O)[C@H](C)C(=O)[C@H](C)[C@@H](OC2O[C@H](C)C[C@H](N(C)C)[C@H]2O)[C@](C)(OC)C[C@@H](C)C(=O)[C@H](C)[C@H]2[C@H](/C(N)=N/O[C@@H](C)c3nnc(-c4ncccn4)s3)C(=O)O[C@@]21C]

In some other embodiment, there is provided a process for preparation of a compound of formula (3-e)

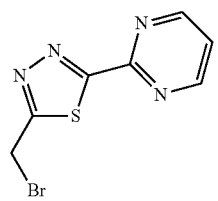

3-e comprising;

(i) converting a compound of formula (3-a) to a compound of formula (3-b);

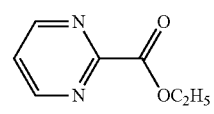

3-a

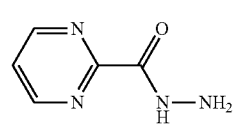

3-b (ii) converting a compound of formula (3-b) to a compound of formula (3-c);

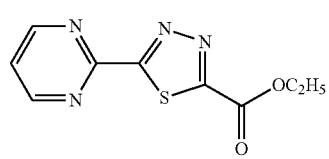

3-c (iii) converting a compound of formula (3-c) to a compound of formula (3-d)

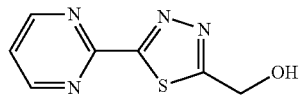

3-d (iv) converting a compound of formula (3-d) to a compound of formula (3-e).

In other embodiments, there is provided a process for preparation of a compound of formula (4-e)

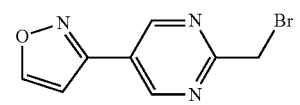

4-e comprising:

(i) converting 2-methyl-pyrimidine-4-carbaldehyde (4-a) to obtain a compound of formula (4-b);

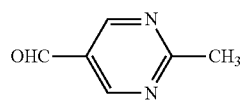

4-a

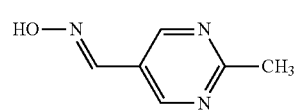

4-b (ii) converting a compound of formula (4-b) to a compound of formula (4-c);

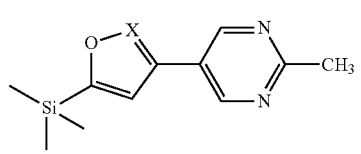

4-c (iii) converting a compound of formula (4-c) to a compound of formula (4-d); and

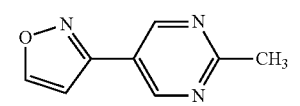

4-d (iv) converting a compound of formula (4-d) to a compound of formula (4-e);

In some embodiments, there is provided a process for preparation of a compound of formula (19-d)

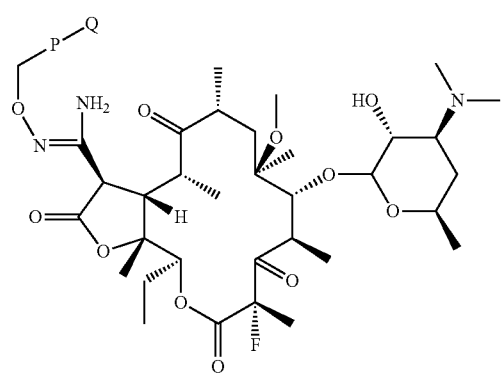

comprising:

(i) reacting a compound of formula (19-a) with a compound of formula (19-b) to obtain a compound of formula (19-c).

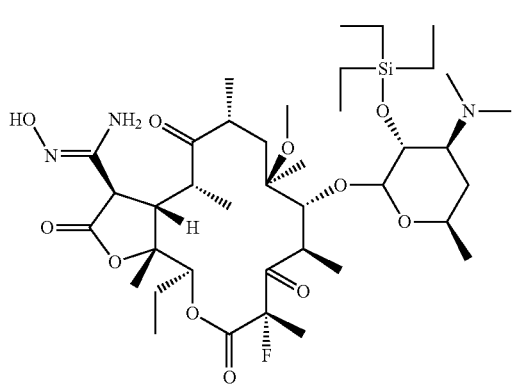

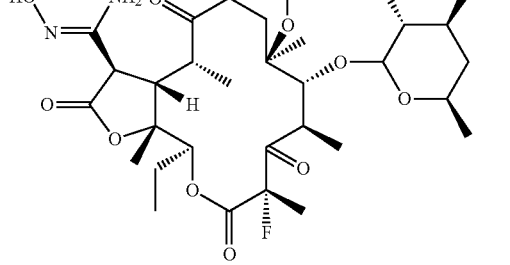

Z = Br or R—SO₂—O— where R = methyl, nosyl P and Q = as defined (ii) converting a compound of formula (19-c) to a compound of formula (19-d).

In some embodiments, there is provided a process for preparation of a compound of formula (15-f)

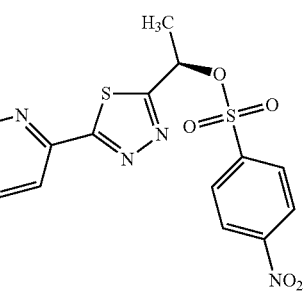

comprising;

(i) converting a compound of formula (15-a) to a compound of formula (15-b);

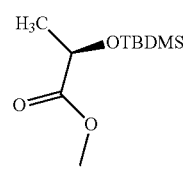

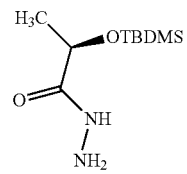

(ii) converting a compound of formula (15-b) to a compound of formula (15-c);

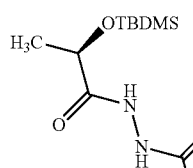

(iii) converting a compound of formula (15-c) to a compound of formula (15-d)

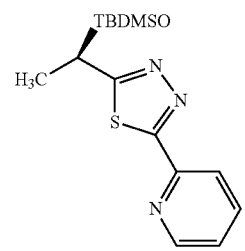

(iv) converting a compound of formula (15-d) to a compound of formula (15-e); and

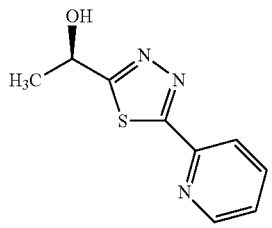
15-e (v) converting a compound of formula (15-e) to a compound of formula (15-f).

In some embodiments, there is provided a process for preparation of a compound of formula (16-d)

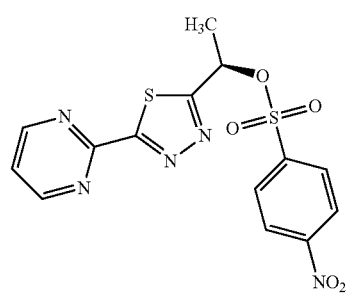
16-d comprising:
(i) reacting pyrimidine-2-carbonylchloride with a compound of formula (15-b) to obtain a compound of formula (16-a);

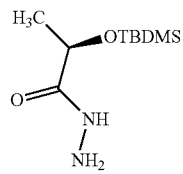
15-b

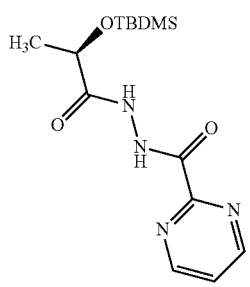
16-a (ii) converting a compound of formula (16-a) to a compound of formula (16-b);

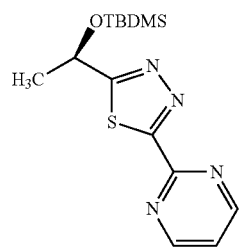
16-b (iii) converting a compound of formula (16-b) to a compound of formula (16-c); and

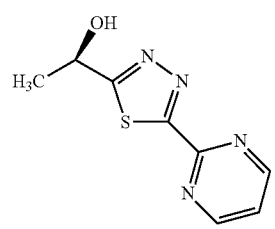
16-c (iv) converting a compound of formula (16-c) to a compound of formula (16-d);

In some embodiments, there is provided a process for preparation of a compound of formula (17-e)

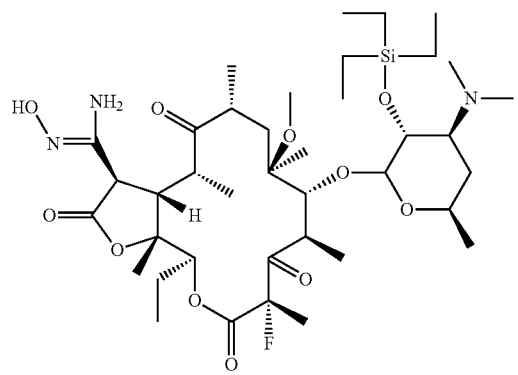
17-e comprising:
(i) converting a compound of formula (17-a) to a compound of formula (17-b)

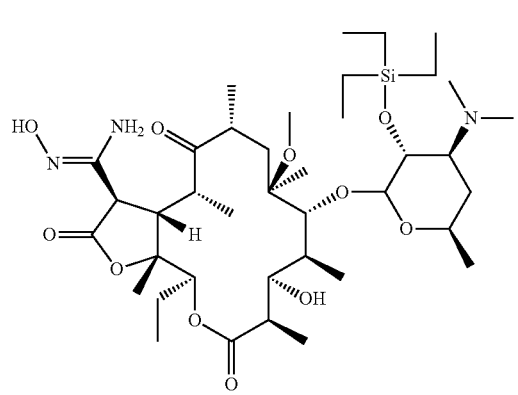
17-a

-continued 17-b
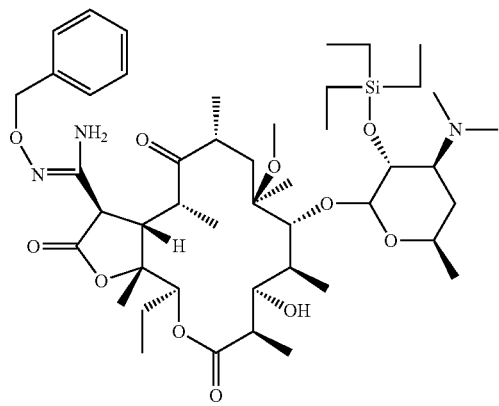

(ii) converting a compound of formula (17-b) to a compound of formula (17-c)

17-c
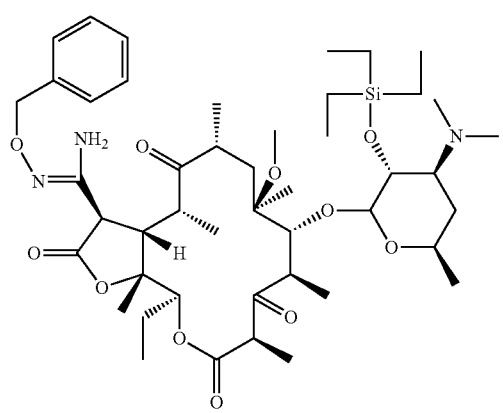

(iii) converting a compound of formula (17-c) to a compound of formula (17-d); and 17-d
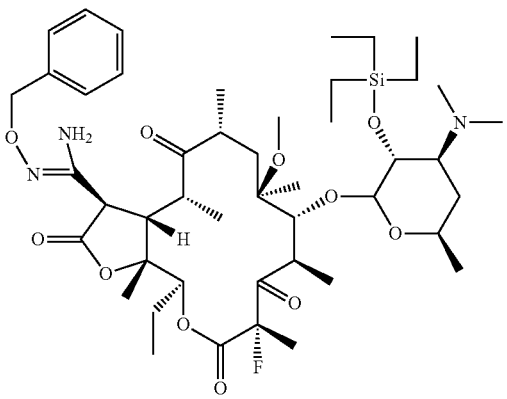

(iv) converting a compound of formula (17-d) to a compound of formula (17-e).

In some other embodiments, there is provided a process for preparation of a compound of formula (18-e)

18-e
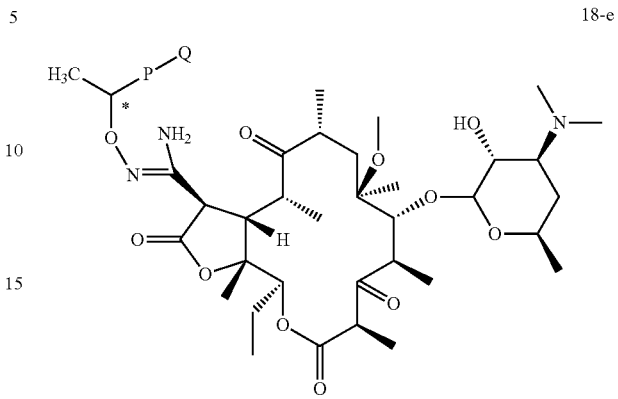

comprising, (i) reacting a compound of formula (18-a) with a compound formula (18-b) to a obtain a compound of formula (18-c)

18-a
18-b
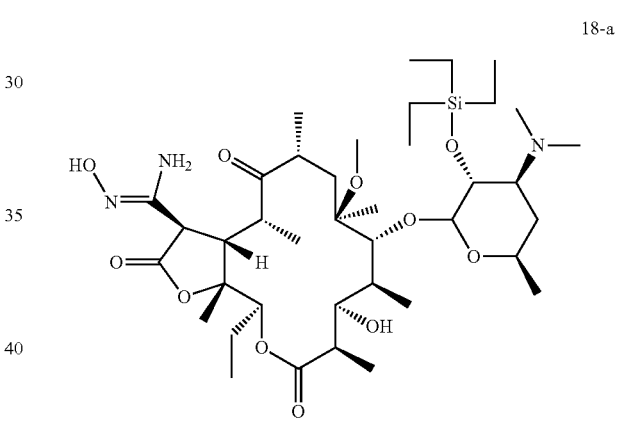

Z = Br or R—SO$_2$—O—
where R = methyl, nosyl;
P and Q is as defined 18-c
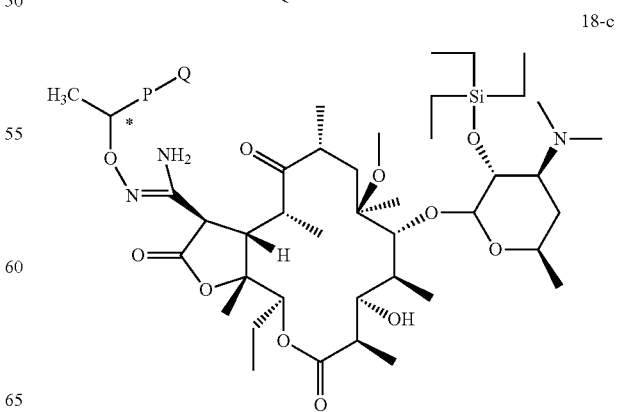

(ii) converting a compound of formula (18-c) to a compound of formula (18-d), and

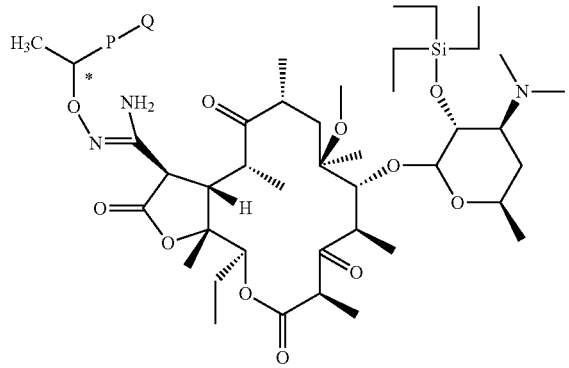

18-d (iii) converting a compound of formula (18-d) to a compound of formula (18-e).

In some embodiments, there is provided a process for preparation of a compound of formula (19-d')

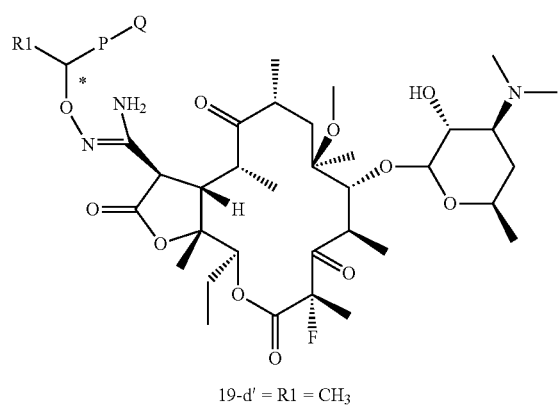

19-d' = R1 = CH₃ comprising,
(i) reacting a compound of formula (19-a) with a compound formula (19-b') to a obtain a compound of formula (19-c'), and

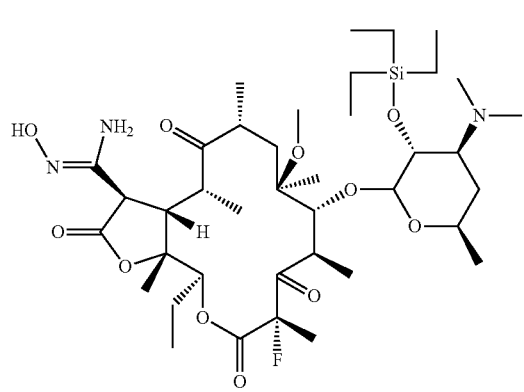

19-a

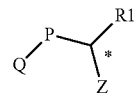

19-b'

Z = Br or R—SO₂—O—  where R = methyl, nosyl
R1 = CH₃
P and Q = as defined

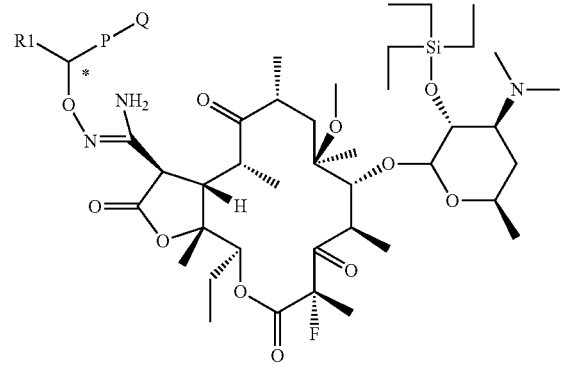

19-c' = R1 = CH₃

(ii) converting a compound of formula (19-c') to a compound of formula (19-d').

In some embodiments, there is provided, a process for the preparation of compounds of Formula (I), wherein the variables have the previously defined meanings, the method comprising the process will be better understood in connection with the following synthetic Schemes In some embodiments, there are provided pharmaceutical compositions comprising therapeutically effective amount of a compound of formula (I) or a pharmaceutically acceptable salt, solvate, polymorph or stereoisomer thereof, optionally, with one or more pharmaceutically acceptable excipient.

The term "pharmaceutically acceptable excipient" refers to a substance other than the active ingredient and includes pharmaceutically acceptable carriers, diluents, stabilizers binders, coloring agents, buffers, lubricants, disintegrating agents, surfactants, glidants, plasticizers, fillers, extenders, emollients, wetting agents, and so on. The pharmaceutically acceptable excipient often facilitates delivery of the active ingredient. The type and amount of any the excipient used depends largely on the therapeutic response desired and other factors such as route of administration and so on.

Any suitable route of administration may be employed for providing the patient with an effective dosage of the compounds of the invention. For example, oral, rectal, vaginal, parenteral (subcutaneous, intramuscular, intravenous), nasal, transdermal, topical and like forms of administration may be employed. Suitable dosage forms include tablets, pills, powders, troches, dispersions, solutions, suspensions, emulsions, capsules, injectable preparations, patches, ointments, creams, lotions, shampoos, and the like.

In some embodiments, the pharmaceutical compositions according to the invention are administered parenterally or orally.

In some embodiments, there is provided a method for treating or preventing microbial infection in a subject, comprising administering to a subject in need thereof a compound of formula (I) or a pharmaceutically acceptable salt, solvate, hydrate, polymorph or stereoisomer thereof.

In some embodiments, there is provided a method for treating infection caused by a microorganism in a subject, comprising administering to a subject in need thereof, a therapeutically effective amount of a compound of formula (I) or a pharmaceutically acceptable salt, solvate, hydrate, polymorph or stereoisomer thereof.

In some other embodiments, there is provided a method for prophylactic treatment of a subject, comprising administering to a subject at risk of infection caused by microorganism, a prophylactically effective amount of a compound of formula (I) or a pharmaceutically acceptable salt, solvate, hydrate, polymorph or stereoisomer thereof.

In some other embodiments, there is provided a method for treating infection caused by a microorganism in a subject, comprising administering to the subject in need thereof, a pharmaceutical composition comprising therapeutically effective amount of a compound of formula (I) or a pharmaceutically acceptable salt, solvate, polymorph or stereoisomer thereof, optionally, with one or more pharmaceutically acceptable excipient.

In some other embodiments, there is provided a method for prophylactic treatment of a subject, comprising administering to a subject at risk of infection caused by microorganism, a pharmaceutical composition comprising therapeutically effective amount of a compound of formula (I) or a pharmaceutically acceptable salt, solvate, polymorph or stereoisomer thereof, optionally, with one or more pharmaceutically acceptable excipient.

The prophylactic or therapeutic dose of the ketolide compounds of Formula (I) and pharmaceutically acceptable salts thereof, in the acute or chronic management of disease will vary with the severity of condition to be treated, and the route of administration. In addition, the dose, and perhaps the dose frequency, will also vary according to the age, body weight and response of the individual patient. In general, the total daily dose range, for the compounds of the invention, for the conditions described herein, is from about 10 mg to about 5000 mg. It may be necessary to use dosages outside these ranges in some cases as will be apparent to those skilled in the art.

Further, it is noted that the clinician or treating physician will know how and when to interrupt, adjust, or terminate therapy in conjunction with individual patient's response.

General Procedures

As per scheme-1, heteroaryl aldoxime of formula 1-a is reacted with N-chlorosuccinamide or sodium hypochlorite, in a suitable solvent such as N,N-dimethylformamide or N,N-dimethylacetamide at a temperature ranging from 25° C. to 35° C. to provide corresponding heteroaryl chloroamidoxime of formula 1-b.

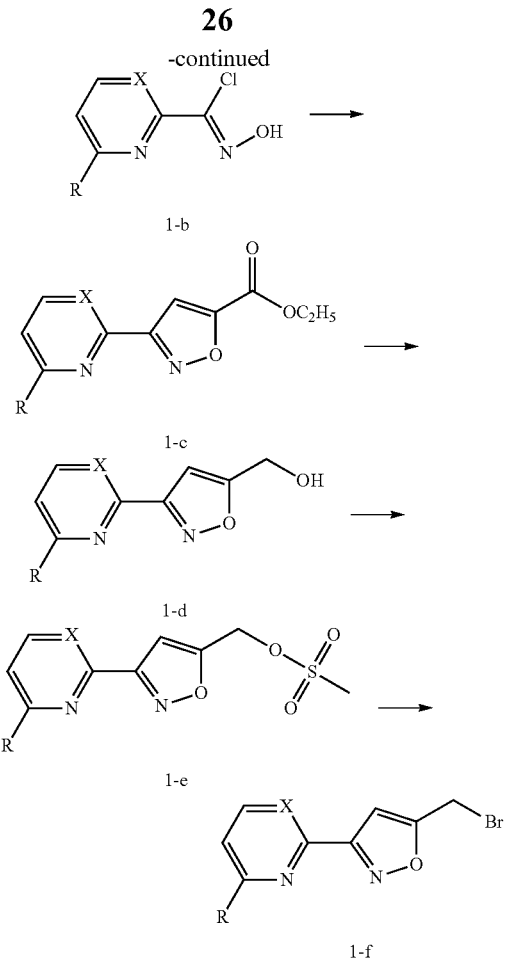

R = H or BocNH—
X = CH or N

The compound of formula 1-b is treated with ethyl propiolate in the presence of organic base such as triethylamine in a suitable solvent such as toluene or xylene, at a temperature ranging from 25° C. to 50° C. to provide corresponding ethyl ester, which in turn was reduced using sodium borohydride in methanol or ethanol at a temperature ranging from 0° C. to 35° C. to provide corresponding methanol derivative of formula 1-d. This intermediate was then reacted with methanesulfonylchloride in the presence of base such as triethylamine in a suitable solvent such as dichloromethane or chloroform at a temperature ranging from −5° C. to 35° C. to provide corresponding methanesulfonic acid ester of formula 1-e, which is further reacted with lithium bromide in a suitable solvent such acetone; at a temperature ranging from 35° C. to 55° C., to provide corresponding bromide intermediate of formula 1-f.

Scheme-1

Scheme-2

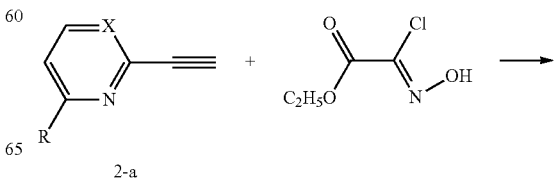

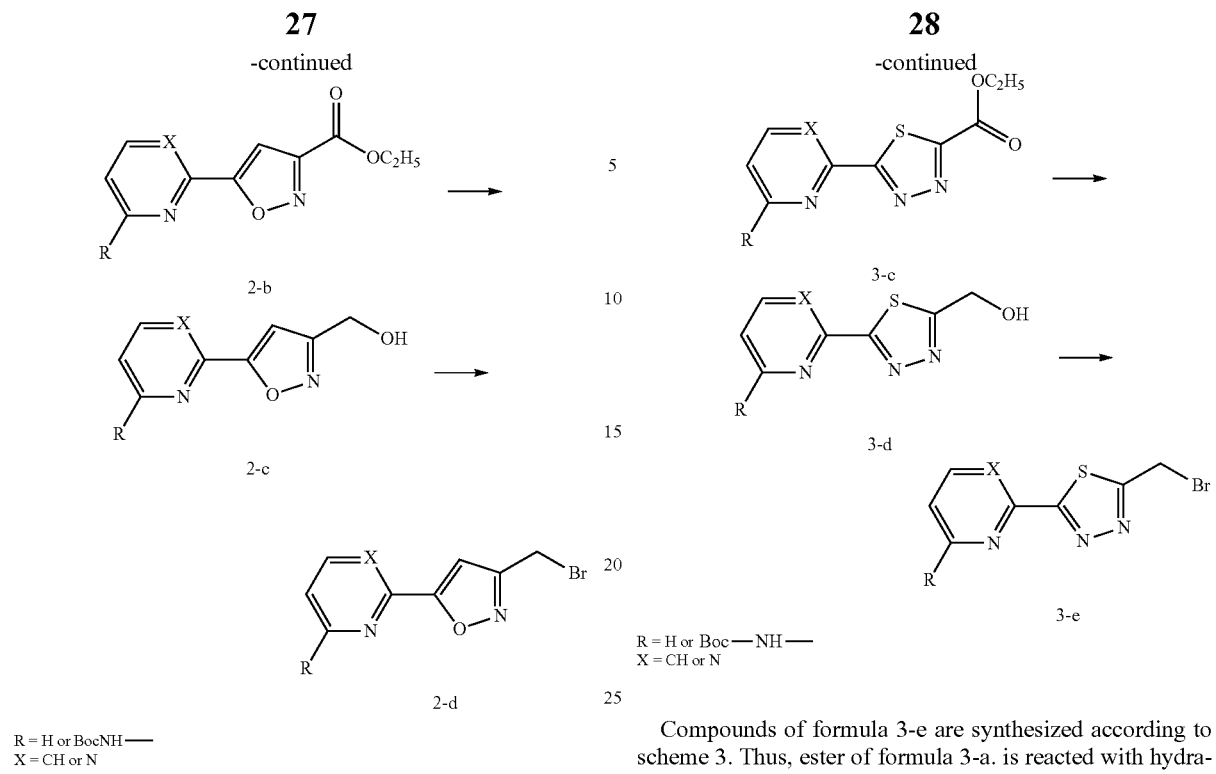

As per scheme-2, ethynyl heteroaryl compound of formula 2-a is reacted with ethylchlorooxamidoacetate in the presence of organic base such as triethylamine, in a suitable solvent such as toluene at a temperature ranging from 80° C. to 95° C. to provide corresponding ethyl ester derivative of formula 2-b.

The ester derivative 2-b is reacted with reducing agent such as sodium borohydride in a suitable solvent such as methanol or ethanol at a temperature ranging from 0° C. to 35° C. to provide corresponding methanol derivative of formula 2-c, which is reacted with methanesulfonyl chloride in the presence of organic base such as triethylamine, in a suitable solvent such as dichloromethane or chloroform at a temperature ranging from −5° C. to 35° C. to provide corresponding methanesulfonic acid ester, which is further reacted with lithium bromide in a suitable solvent such as acetone at a temperature ranging from 35° C. to 55° C., to provide corresponding methyl bromide derivative of formula 2-d.

Scheme-3

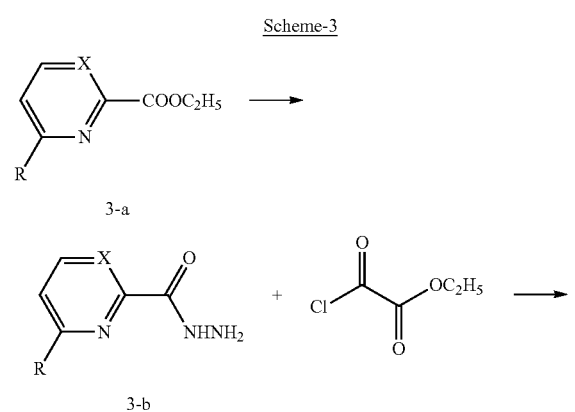

Compounds of formula 3-e are synthesized according to scheme 3. Thus, ester of formula 3-a. is reacted with hydrazine or hydrazine hydrate in a suitable solvent such as methanol or ethanol at a temperature ranging from 25° C. to 85° C. to provide corresponding hydrazide derivative of formula 3-b.

It is then treated with mono ethyl ester of oxalyl chloride in the presence of organic base such as triethylamine in a suitable solvent such as dichloromethane or chloroform or tetrahydrofuran at a temperature ranging from −5° C. to 35° C., followed by optionally changing to solvent selected from tetrahydrofuran or 1,4-dioxane and the reaction mixture is treated with Lawesson's reagent at a temperature ranging from 40° C. to 70° C. to provide the requisite Thiadiazole derivative of formula 3-c.

The ester (3-c) is reacted with reducing agent such as sodium borohydride in a suitable solvent ethanol or aqueous ethanol at a temperature ranging from −5° C. to 35° C. to provide corresponding methanol derivative of formula 3-d.

The alcohol (3-d) is reacted with methanesulfonylchloride in the presence of organic base such as triethylamine in a suitable solvent such as dichloromethane or chloroform at a temperature ranging from −5° C. to 35° C. to provide corresponding mesylate derivative, which is further reacted with lithium bromide in a suitable solvent such as acetone at a temperature ranging from 35° C. to 55° C. to provide corresponding bromide of formula 3-e.

Optionally, heteroaryl-1,3,4-thiadiazolyl-methyl bromide derivative of formula 3-e is prepared by reacting methanol intermediate (3-d) with carbontetrabromide along with triphenylphosphine in a suitable solvent such as dichloromethane at a temperature ranging from 0° C. to 35° C.

Scheme-4

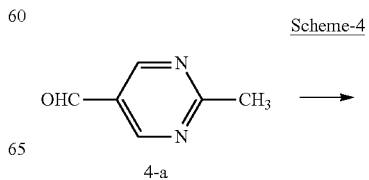

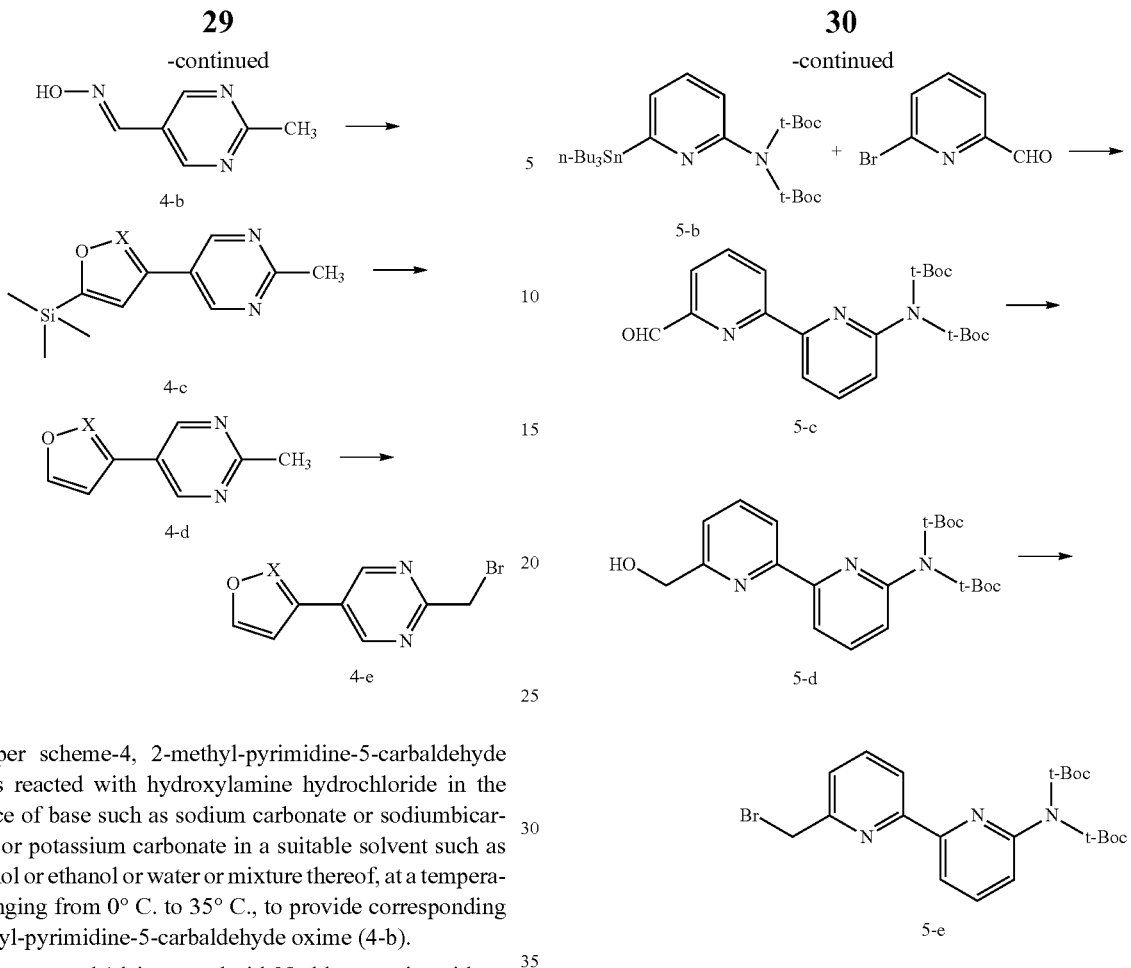

As per scheme-4, 2-methyl-pyrimidine-5-carbaldehyde (4-a) is reacted with hydroxylamine hydrochloride in the presence of base such as sodium carbonate or sodiumbicarbonate or potassium carbonate in a suitable solvent such as methanol or ethanol or water or mixture thereof, at a temperature ranging from 0° C. to 35° C., to provide corresponding 2-methyl-pyrimidine-5-carbaldehyde oxime (4-b).

The compound 4-b is reacted with N-chlorosuccinamide or sodium hypochlorite, in a suitable solvent such as N,N-dimethylformamide or N,N-dimethylacetamide at a temperature ranging from 0° to 35° C. to provide corresponding methyl substituted pyrimidinyl chloroamidoxime compound, which is further treated with trimethylsilylacetylene in a suitable solvent such as diethyl ether or N,N-dimethylformamide, or mixture thereof, at a temperature ranging from −5° C. to 35° C. to provide corresponding compound 4-c.

The compound 4-c is converted to compound 4-d by reacting it with base such as sodium carbonate or potassium carbonate or sodiumbicarbonate in a suitable solvent such as methanol or ethanol at a temperature ranging from 0° C. to 50° C.

The compound 4-d is reacted with N-bromosuccinamide in the presence of radical initiator such as benzoyl peroxide or azoisobutyronitrile (AIBN) in carbon tetrachloride at a temperature ranging from 65° C. to 80° C. to provide corresponding isoxazolyl-pyrimidinyl methyl bromide compound 4-e.

Scheme-5

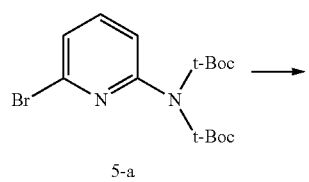

As per scheme-5, 2-bromo-6-N,N-di-t-butyloxycarbonylamino-pyridine (5-a) is reacted with hexabutyldistannane in the presence of palladium catalyst such as Palladium-tetrakis (triphenylphosphine) or bis(triphenylphosphine)palladium (II)dichloride in a suitable solvent such as dimethoxyethane or DMF or toluene, at a temperature ranging from 80° C. to 90° C., to provide corresponding tributyltin derivative of pyridine 5-b.

The compound 5-b is coupled with 2-bromo-pyridine-6-carbaldehyde using catalyst such as palladium-tetrakis(triphenylphosphine) in the presence of lithium chloride and base such as triethylamine in toluene at a temperature ranging from 100° C. to 110° C. to provide a corresponding coupled product 5-c.

The compound 5-c is reacted with a reducing agent such as sodium borohydride in a suitable solvent tetrahydrofuran or ethanol or methanol or aqueous ethanol or mixture thereof, at a temperature ranging from 25° C. to 35° C. to provide corresponding substituted pyridinyl methylalcohol compound 5-d.

The compound 5-d is reacted with methanesulfonylchloride in the presence of organic base such as triethylamine in a suitable solvent such as dichloromethane or chloroform at a temperature ranging from 0° C. to 25° C. to provide corresponding methanesulfonic acid ester of substituted pyridinyl methylalcohol, which is further reacted with lithium bromide in a suitable solvent such as acetone at a temperature ranging from 35° C. to 55° C. to provide corresponding substituted bispyridinyl methyl bromide compound 5-e.

Scheme-6

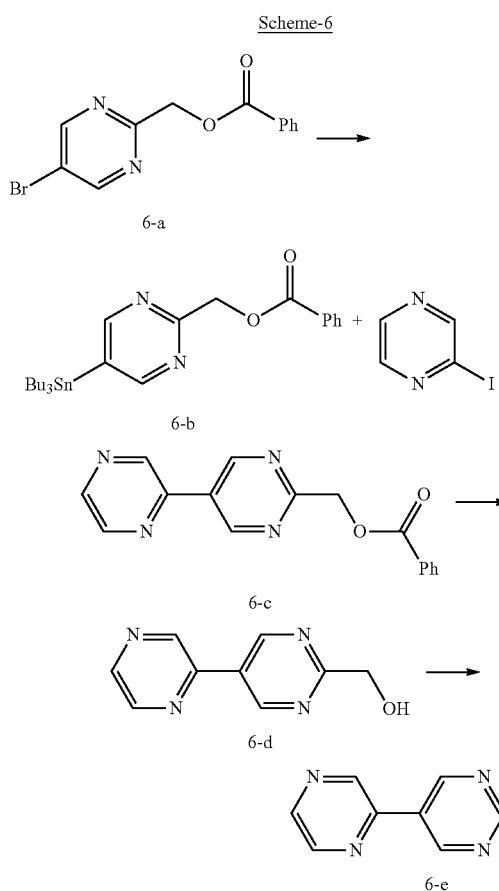

Scheme-7

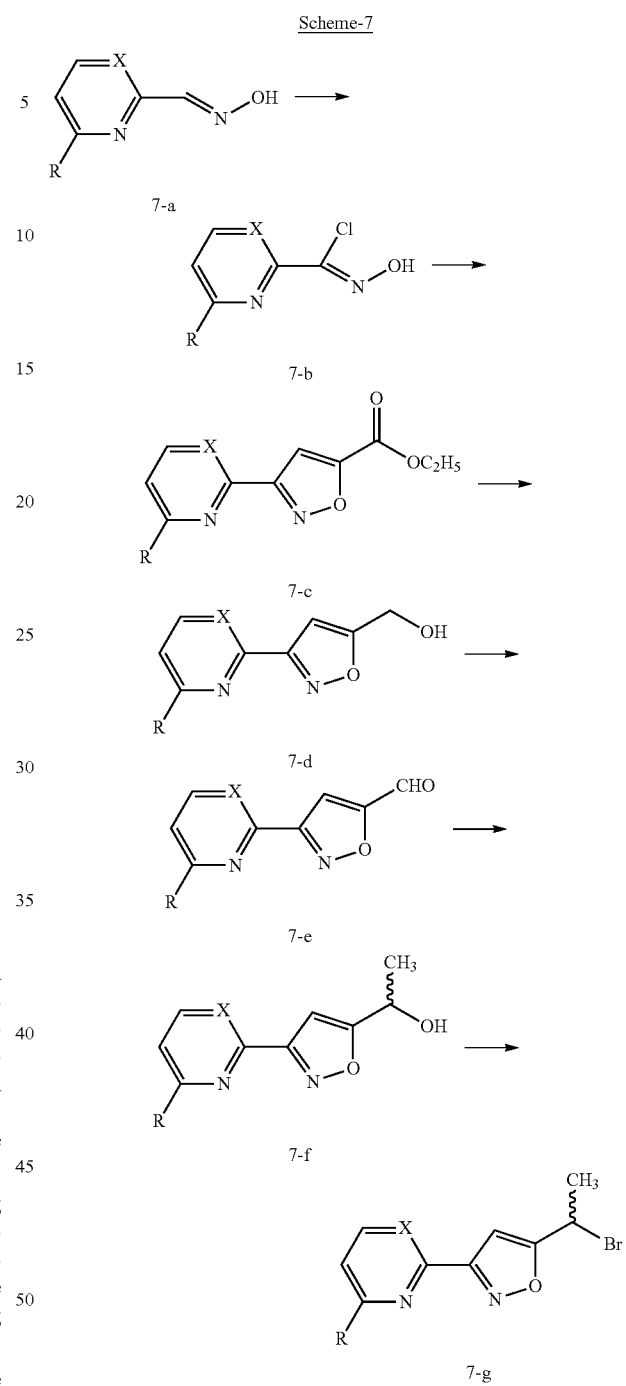

X = CH or N
R = H or BocNH—— or OBn

Compound 6-e is synthesized according to scheme-6, in which 5-bromo-2-benzoyloxymethyl-pyrimidine (6-a) is reacted with hexabutyldistannane in the presence of palladium catalyst such as Palladium-tetrakis(triphenylphosphine) or bis(triphenylphosphine)palladium(II)dichloride in a suitable solvent such as toluene, dimethoxyethane or DMF, at a temperature ranging from 80° C. to 110° C., to provide corresponding tributyltin derivative of pyrimidine 6-b.

The compound 6-b is coupled with 2-iodo-pyrazine using catalyst such as bis(triphenylphosphine)palladium(II)dichloride or palladium-tetrakis(triphenylphosphine) in the presence of base such as triethylamine in DMF at a temperature ranging from 100° C. to 110° C. to provide a corresponding coupled product 6-c.

The compound 6-c is saponified by stirring with a base such as sodium methoxide in a suitable solvent such as methanol at a temperature ranging from 25° C. to 35° C. to provide corresponding substituted pyrimidinyl methylalcohol compound 6-d.

The compound 6-d is reacted with methanesulfonylchloride in the presence of organic base such as triethylamine in a suitable solvent such as dichloromethane or chloroform at a temperature ranging from 0° C. to 25° C. to provide corresponding methanesulfonic acid ester of substituted pyrimidinyl methylalcohol, which is further reacted with lithium bromide in a suitable solvent such as acetone at a temperature ranging from 35° C. to 55° C. to provide corresponding substituted pyrimidinyl methyl bromide compound 6-e.

As per scheme-7, heteroaryl aldoxime of formula 7-a is reacted with N-chlorosuccinamide or sodium hypochlorite, in a suitable solvent such as N,N-dimethylformamide or N,N-dimethylacetamide or mixture thereof, at a temperature ranging from 25° C. to 35° C. to provide corresponding heteroaryl chloroamidoxime compound 7-b. It is then treated with ethyl propiolate in the presence of organic base such as triethylamine, diisopropylethylamine in a suitable solvent such as toluene or xylene at a temperature ranging from 25° C. to 50° C. to provide corresponding ethyl ester of formula 7-c.

The ester intermediate in turn is reacted with reducing agent such as sodium borohydride in a suitable solvent such as methanol or ethanol or tetrahydrofuran (THF) or mixture thereof, at a temperature ranging from 0° C. to 35° C. to provide corresponding alcohol of formula 7-d.

The alcohol (7-d) is reacted with oxidizing agent such as Dess-Martin periodinane or pyridiniumchlorochromate (PCC) or pyridiniumfluorochromate (PFC) in a suitable solvent such as dichloromethane or dichloroethane or chloroform or mixture thereof, at a temperature ranging from 25° C. to 35° C. to provide corresponding aldehyde derivative of formula 7-e. The aldehyde (7-e) is reacted with methylmagnesiumiodide in a suitable solvent such as dichloromethane or dichloroethane or chloroform or tetrahydrofuran (THF) or mixture thereof, at a temperature ranging from 0° C. to 10° C. to provide corresponding alcohol (7-f). Which is converted to corresponding bromomethyl derivative 7-g by reacting either with methanesulfonyl chloride in the presence of base such as triethylamine and isolating corresponding alkyl sulfonate and treating it with lithium bromide in acetone at reflux temperature or optionally, by reacting with carbon tetrabromide along with triphenylphosphine in a suitable solvent such as tetrahydrofuran (THF) at a temperature ranging from 10° C. to 35° C.

Scheme-8

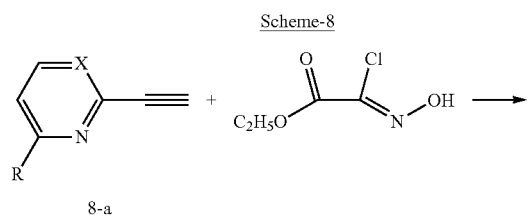

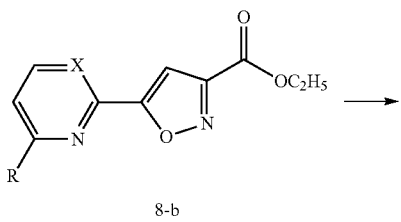

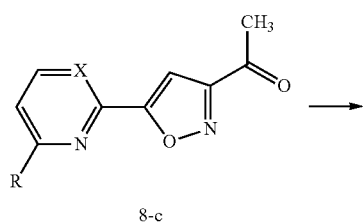

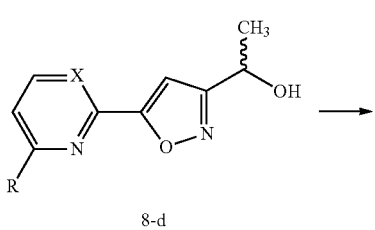

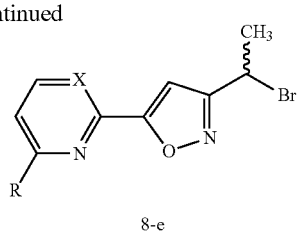

X = CH or N
R = H or BocNH— or OBn

As per scheme-8, ethynyl heteroaryl derivative of formula 8-a is reacted with ethylchloro oxamidoacetate in the presence of organic base such as triethylamine in a suitable solvent such as toluene at a temperature ranging from 80° C. to 110° C. to provide corresponding ester (8-b). It is in turn reacted with methylmagnesiumiodide in a suitable solvent such as dichloromethane or dichloroethane or chloroform or tetrahydrofuran (THF) or mixture thereof, at a temperature ranging from 0° C. to 10° C. to provide corresponding ketone derivative (8-c). The ketone is reduced using sodium borohydride in a suitable solvent such as methanol or ethanol or tetrahydrofuran (THF) or mixture thereof, at a temperature ranging from 0° C. to 35° C. to provide corresponding alcohol derivative of formula 8-d.

The alcohol is converted to the corresponding mesylate derivative using methanesulfonylchloride in the presence of organic base such as triethylamine, in a suitable solvent such as dichloromethane or dichloroethane or chloroform or tetrahydrofuran (THF) or mixture thereof, at a temperature ranging from 0° C. to 15° C., which is then converted to corresponding heteroaryl-isoxazolyl bromide of formula 8-e by treating it with lithium bromide in a suitable solvent such as acetone; at a temperature ranging from 45° C. to 55° C.

Scheme-9

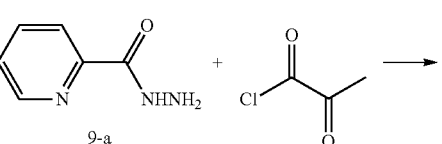

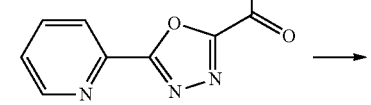

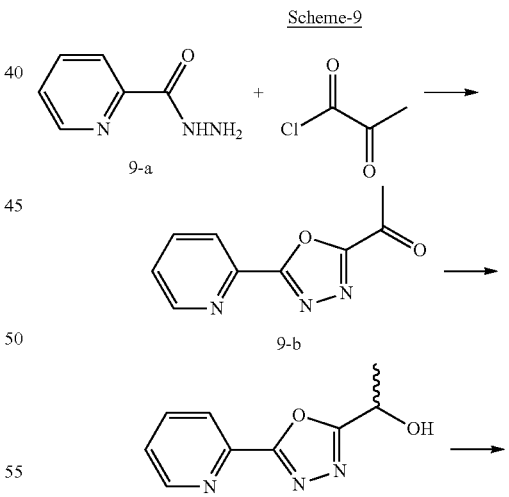

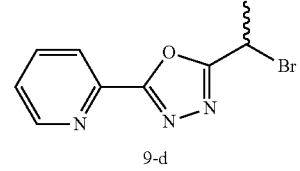

As per scheme-9, 2-picolinic acid hydrazide (9-a) is reacted with pyruvic acid chloride in the presence of organic base such as triethylamine in dichloromethane at a temperature 0° C. to 5° C. for up to 3 hr. The reaction mixture is further treated with p-toluene sulfonyl chloride and is allowed to stir at ambient temperature for up to 16 hr to provide pyridine-1,3,4-oxadiazole compound 9-b. The compound 9-b, thus obtained, is reacted with reducing agent sodium borohydride in methanol or ethanol at a temperature 35° C. to provide pyridine-1,3,4-oxadiazole ethanol (9-c). The compound 9-c is reacted with methanesulfonylchloride in the presence of triethylamine in dichloromethane at a temperature ranging from 0° C. to 15° C. to provide corresponding methanesulfonyl ester of pyridinyl-1,3,4-oxadiazolyl-ethanol, which is converted to corresponding pyridine-1,3,4-oxadiazolyl ethyl bromide (9-d) by treating sulfonyl ester with lithium bromide in acetone at reflux temperature.

Scheme-10

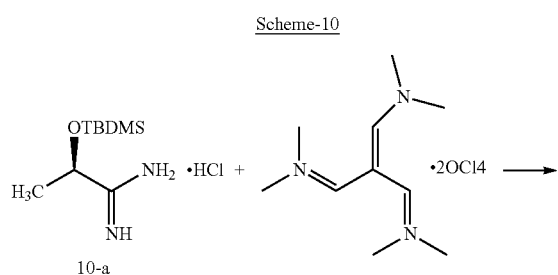
10-a

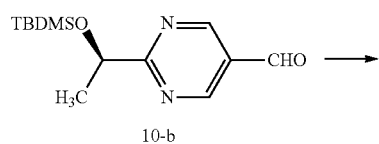
10-b

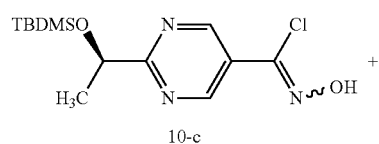
10-c

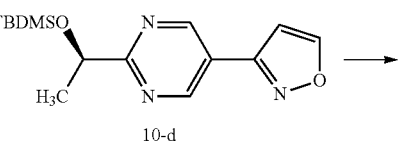
10-d

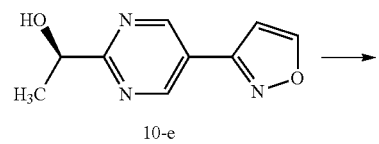
10-e

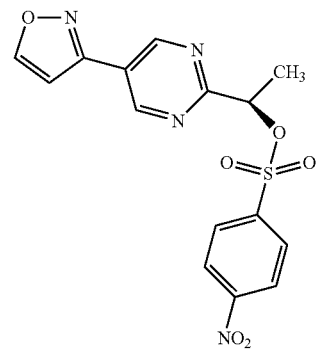
10-f

Chiral nosylate (10-f) is synthesized according to scheme 10. R enantiomer of amidine hydrochloride compound 10-a is reacted with vinamidium diperchlorate salt and aqueous sodium hydroxide in acetonitrile at 25° C. to 35° C. temperature, to provide corresponding pyrimidine carbaldehyde compound 10-b. The compound 10-b is reacted with hydroxylamine hydrochloride in presence of sodium carbonate in aqueous methanol at ambient temperature to provide corresponding oxime, which is subsequently reacted with N-chlorosuccinamide in DMF at the same temperature to provide corresponding chloroamidate compound 10-c. The compound 10-c is stirred with triethylamine and trimethylsilyl acetylene in DMF and diethyl ether mixture at −10° C. to 25° C. to provide corresponding trimethylsilyl protected isoxazolyl-pyrimidine compound, which upon treatment with sodium carbonate in methanol at ambient temperature provided isoxazolyl-pyrimidinyl compound 10-d. The TBDMS group is removed by reacting 10-d with HF.pyridine reagent in acetonitrile at 25° C. to 35° C. to provide compound 10-e with free hydroxyl function. The hydroxyl group is then protected by reaction of 10-e with p-nitrophenylsulfonylchloride in presence of triethylamine in dichloromethane at 0° C. to 5° C. temperature to yield corresponding p-nitrophenylsulfonyl ester compound 10-f.

Scheme-11

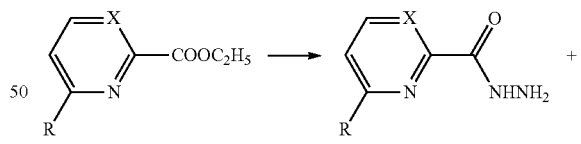
11-a                            11-b

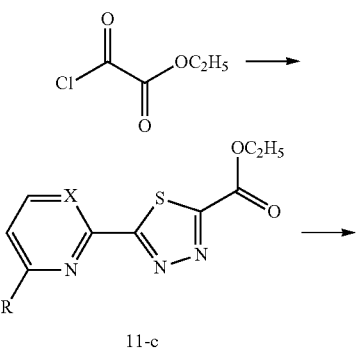
11-c

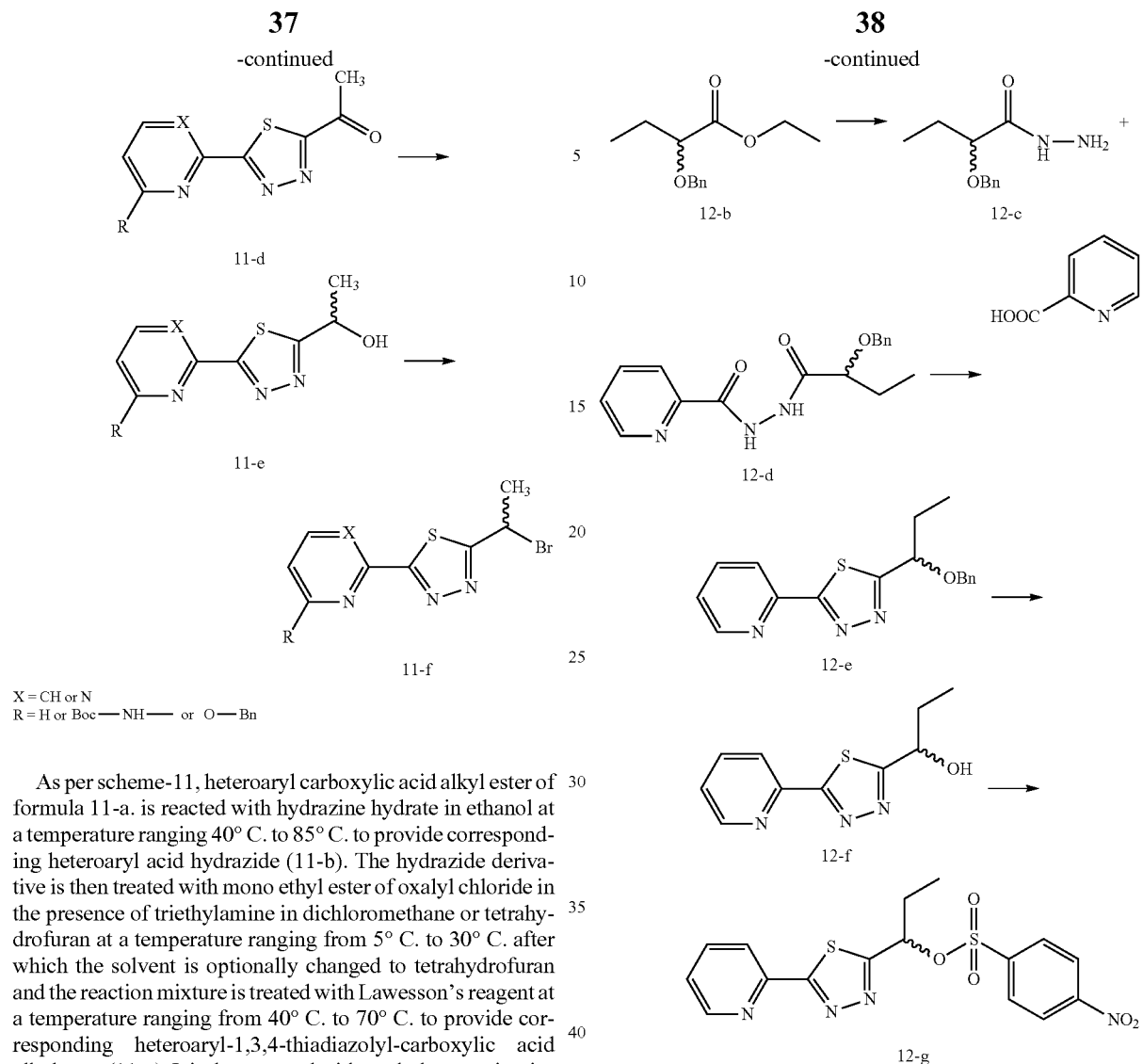

X = CH or N
R = H or Boc—NH— or O—Bn

As per scheme-11, heteroaryl carboxylic acid alkyl ester of formula 11-a. is reacted with hydrazine hydrate in ethanol at a temperature ranging 40° C. to 85° C. to provide corresponding heteroaryl acid hydrazide (11-b). The hydrazide derivative is then treated with mono ethyl ester of oxalyl chloride in the presence of triethylamine in dichloromethane or tetrahydrofuran at a temperature ranging from 5° C. to 30° C. after which the solvent is optionally changed to tetrahydrofuran and the reaction mixture is treated with Lawesson's reagent at a temperature ranging from 40° C. to 70° C. to provide corresponding heteroaryl-1,3,4-thiadiazolyl-carboxylic acid alkyl ester (11-c). It is then reacted with methylmagnesiumiodide in a suitable solvent such as dichloromethane or tetrahydrofuran (THF) or mixture thereof, preferably dichloromethane at a temperature ranging from 0° C. to 10° C. to provide corresponding heteroaryl-1,3,4-thiadiazolyl-ethan-2-one (11-d). The ketone is reduced using sodium borohydride in ethanol or methanol at a temperature ranging from 0° C. to 35° C. to provide corresponding alcohol (11-e). The alcohol (11-e) is reacted with methanesulfonylchloride in the presence of triethylamine, in dichloromethane at a temperature ranging from −10° C. to 40° C., preferably 0° C. to 15° C. to provide corresponding methanesulfonic acid ester of heteroaryl-1,3,4-thiadiazolyl ethanol, which is converted to corresponding bromide (11-f) by treating with lithium bromide in acetone, at a reflux temperature.

Scheme-12

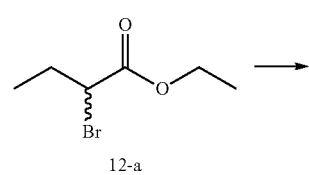

12-a

As per scheme-12, ethyl-2-bromobutyrate (12-a) is reacted with benzyl alcohol in presence of potassium hydroxide in DMF at 25° C. to 35° C. up to 3 hr to provide ethyl-2-benzyloxybutyrate (12-b). Compound 12-b is treated with hydrazine hydrate in ethanol at reflux temperature to provide corresponding acid hydrazide compound 12-c. The compound 12-c is treated with 2-picolinic acid in the presence of dehydrating agent EDC along with HOBt and N-methyl morpholine in DMF at a temperature 0° C. to 30° C. for 1 hr to provide uncyclized compound 12-d. The compound 12-d is further treated with Lawesson's reagent in tetrahydrofuran at a reflux temperature for 4 hr to provide corresponding pyridinyl-1,3,4-thiadiazolyl compound 12-e. The compound 12-e is stirred with borontribromide in dichloromethane at a temperature ranging from 0° C. to 5° C. for 1 hr followed by at 35° C. for overnight, to provide corresponding pyridinyl-1,3,4-thiadiazolyl propanol compound 12-f. The compound 12-f is treated with p-nitrophenylsulfonyl chloride in the presence triethylamine in a dichloromethane at a temperature ranging from 0° C. to 15° C. to provide corresponding p-nitrophenyl sulfonic acid ester compound 12-g.

Scheme-13

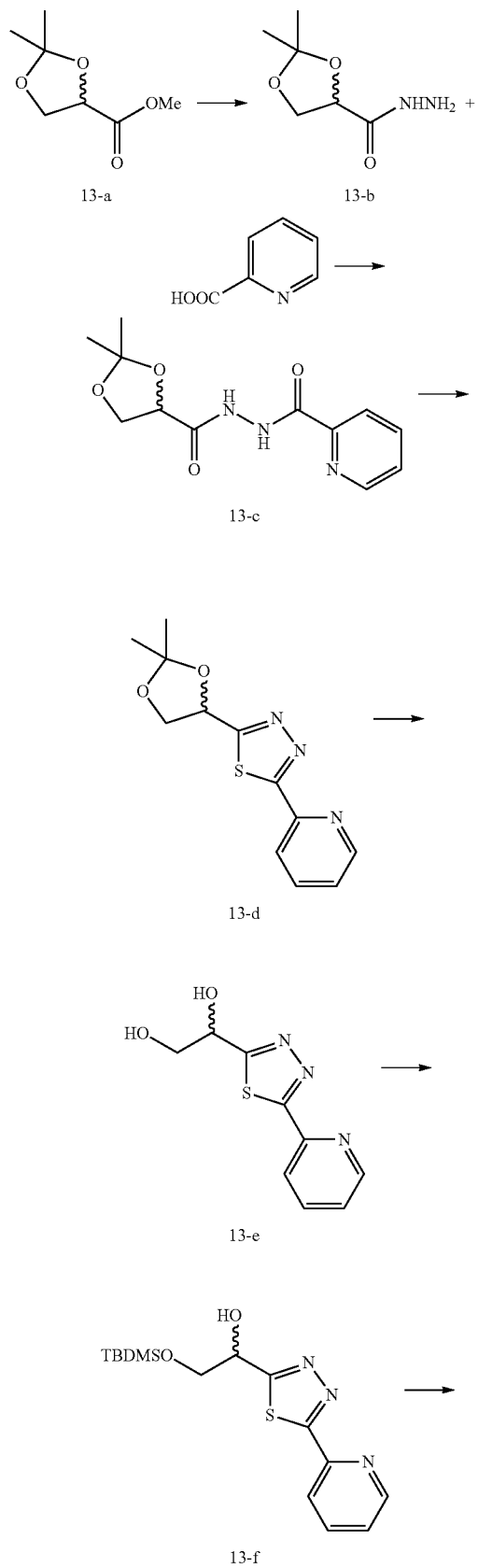

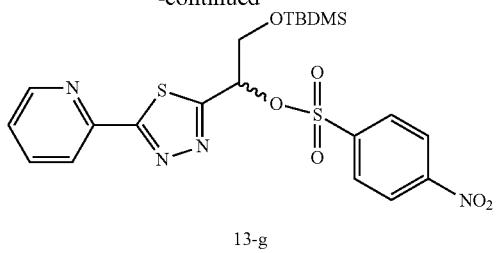

As per scheme-13, O-isopropylidene methyl ester 13-a is reacted with hydrazine hydrate in methanol at 50° C. to 55° C. temperature for overnight to provide corresponding acid hydrazide compound 13-b. The compound 13-b is treated with 2-picolinic acid in the presence of dehydrating agent EDC along with HOBt and N-methyl morpholine in DMF at a temperature 0° C. to 30° C. for 16 hr to provide compound 13-c. It is further treated with Lawesson's reagent in tetrahydrofuran at a 35° C. temperature for 36 hr to provide corresponding pyridinyl-1,3,4-thiadiazolyl compound 13-d.

The protected diol in turn is stirred with aqueous hydrochloric acid in acetone at 40° C. temperature for 6 hr, to provide corresponding pyridinyl-1,3,4-thiadiazolyl ethanediol compound 13-e. It is then reacted with TBDMS chloride in presence of triethylamine and DMAP in dichloromethane at 0° C. to 35° C. for 24 hr to afford monoTBDMS protected compound 13-f, which is stirred with p-nitrophenylsulfonyl chloride in the presence triethylamine in a dichloromethane at a temperature ranging from 0° C. to 5° C. to provide corresponding p-nitrophenyl sulfonate ester compound 13-g.

Scheme-14

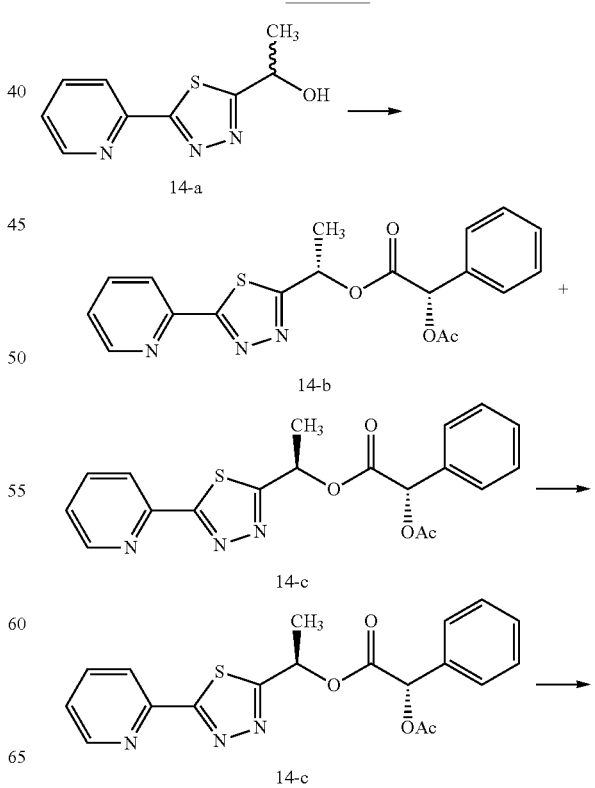

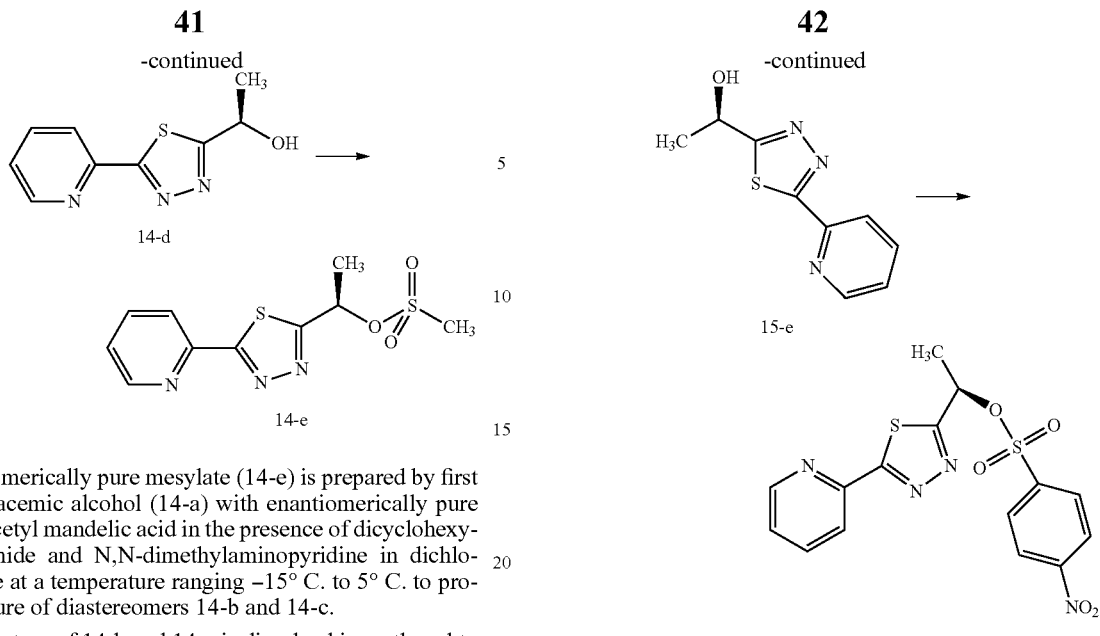

Enantiomerically pure mesylate (14-e) is prepared by first reacting racemic alcohol (14-a) with enantiomerically pure (S)—O-acetyl mandelic acid in the presence of dicyclohexylcarbodiimide and N,N-dimethylaminopyridine in dichloromethane at a temperature ranging −15° C. to 5° C. to provide mixture of diastereomers 14-b and 14-c.

This mixture of 14-b and 14-c is dissolved in methanol to provide clear solution and then cooled to 25° C. to provide selective crystallization of one diastereomer 14-c as a white solid. The compound 14-c is hydrolyzed by treating it with aqueous sodium hydroxide or potassium hydroxide in methanol at temperature ranging from −15° C. to 5° C. to provide enantiomerically pure compound 14-d. The alcohol (14-d) is then reacted with methanesulfonyl chloride in the presence of triethylamine in dichloromethane at a temperature ranging from −10° C. to 5° C. to provide enantiomerically pure corresponding methanesulfonic acid ester compound 14-e.

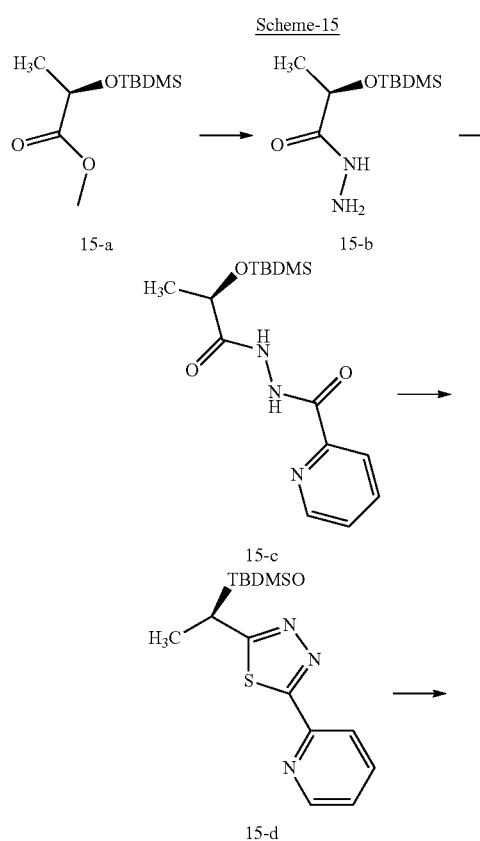

As per scheme-15, commercially available D-Methyl lactate is first protected with TBDMS-Cl, to provide a compound 15-a. and then reacted with hydrazine hydrate at reflux temperature in ethanol to provide corresponding acid hydrazide compound 15-b. The compound 15-b is coupled with 2-picolinic acid using dehydrating agent EDC in the presence of N-methyl morpholine and HOBt in a solvent such as DMF at 25° C. to 35° C. temperature to afford compound 15-c. The cyclization of compound 15-c is effected by reacting it with Lawesson's reagent in THF at reflux temperature to provide pyridinyl-1,3,4-thiadiazole TBDMS protected compound 15-d. The TBDMS group in compound 15-d is removed by using 2 N aqueous hydrochloric acid in acetonitrile at temperature 25° C. to 35° C. to provide a compound 15-e. The compound 15-e is reacted with p-nitrophenylsulfonyl chloride in the presence triethylamine in dichloromethane at a temperature between 10° C. to 25° C. to provide R enantiomer of p-nitrophenylsulfonic acid ester (nosylate) of pyridine-1,3,4-thiadiazole as compound 15-f.

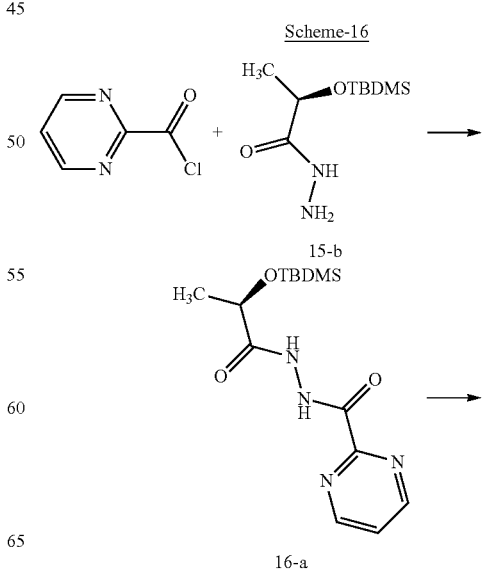

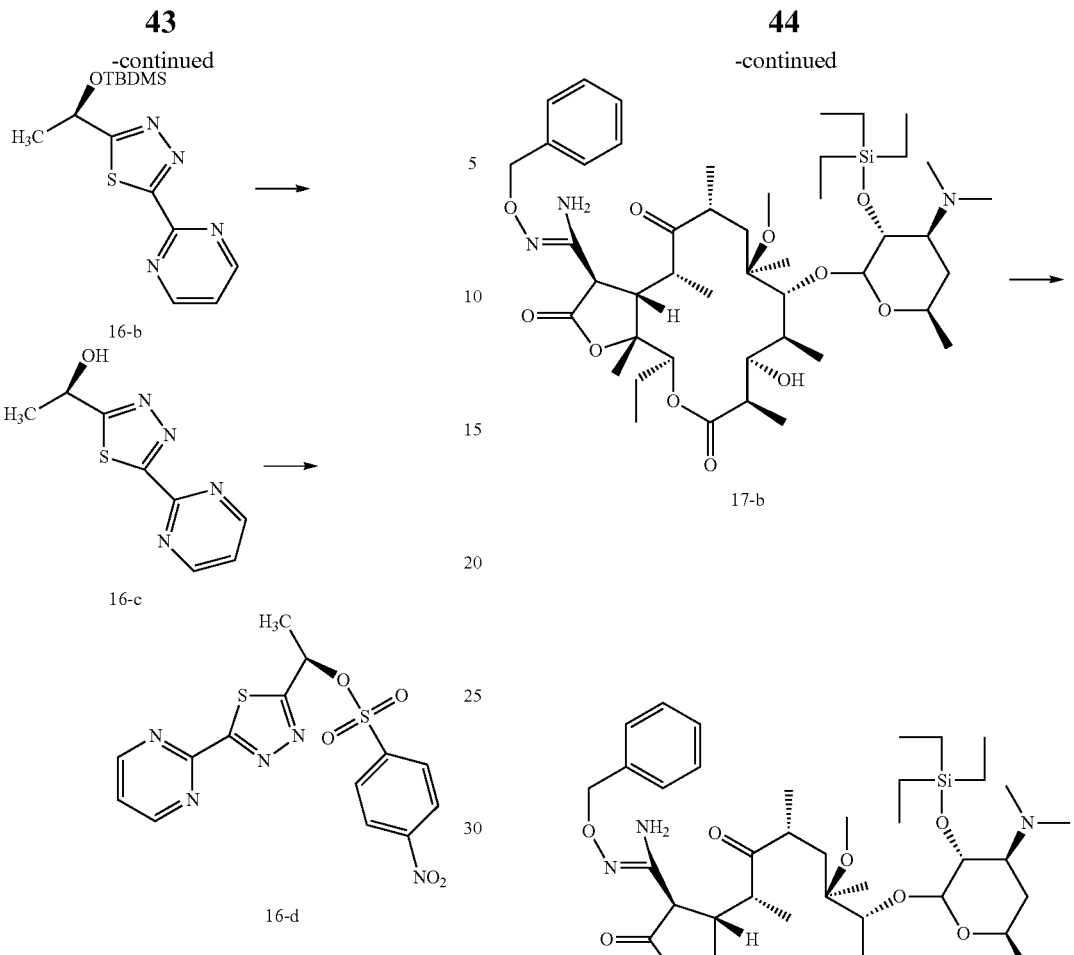

As per scheme-16, pyrimidine-2-carbonylchloride (prepared from 2-cyanopyrimidine by using aqueous sodium hydroxide and subsequent treatment with thionylchloride in toluene) is reacted with R enantiomer of TBDMS protected D-lactic acid hydrazide (15-b), in toluene at a temperature 10° C. to 15° C. for 1 hr to provide compound 16-a. The compound 16-a is cyclized by reacting with Lawesson's reagent in THF at reflux temperature to provide TBDMS protected pyrimidinyl-1,3,4-thiadiazolyl compound 16-b. The TBDMS group is removed by using 2 N aqueous hydrochloric acid in acetonitrile at temperature 25° C. to 35° C. to provide a compound 16-c. which is reacted with p-nitrophenylsulfonyl chloride in the presence triethylamine in dichloromethane at a temperature between 0° C. to 5° C. to provide chirally pure (R)-p-nitrophenylsulfonic acid ester (nosylate) of pyrimidine-1,3,4-thiadiazole as compound 16-d.

Scheme-17

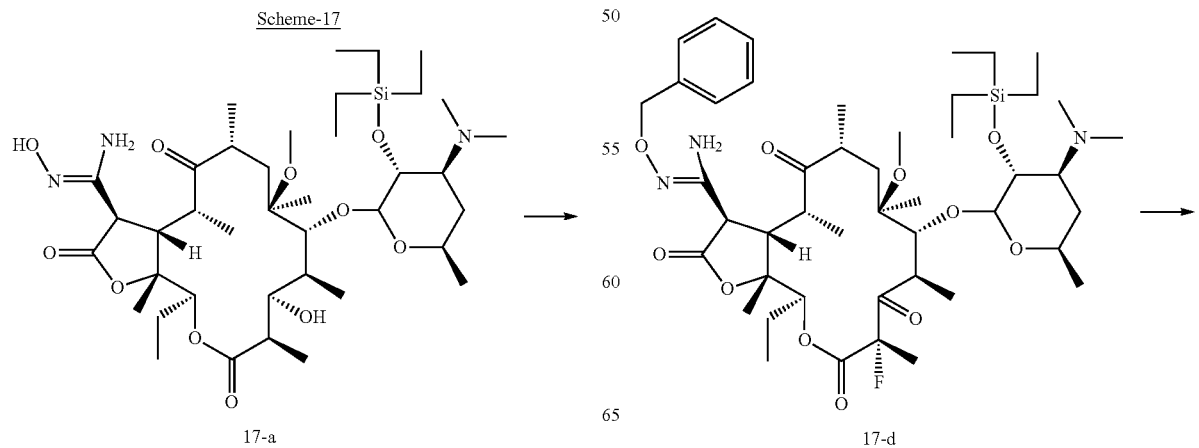

General Procedure for Synthesis of Ketolides of Invention:

Scheme-18

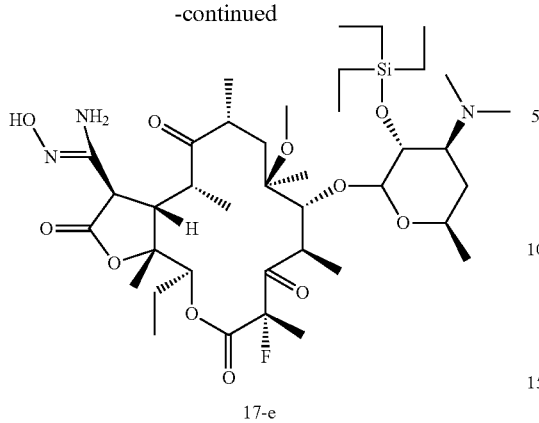

17-e

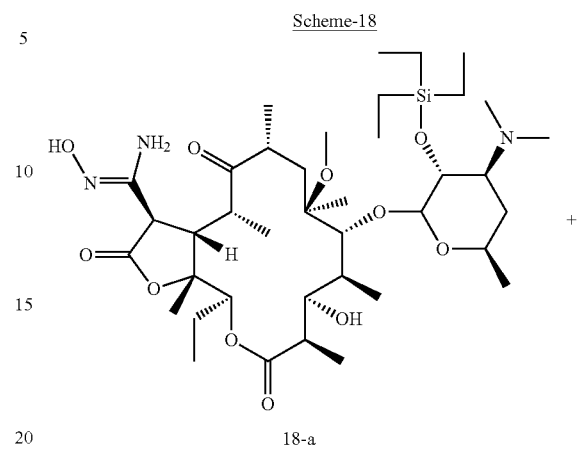

18-a

As per scheme-17, (11S,21R)- 3-decladinosyl-11,12-dideoxy-6-O-methyl-2'-O-triethylsilyl-12,11-{oxycarbonyl-[E-(N-hydroxy)-carboxamidino]methylene}-erythromycin A (17-a) is reacted with triethylbenzylammonium bromide (generated in situ by mixing benzyl bromide and triethylamine in tetrahydrofuran) in the presence of powdered potassium hydroxide tetrahydrofuran at a temperature ranging from 20° to 35° C., to provide corresponding benzyl ether amidoxime macrolide compound 17-b.

Alternatively, compound 17-b is prepared by reacting amidoxime macrolide 17-a with benzyl bromide in presence of base such as potassium hydride or potassium carbonate or potassium t-butoxide in presence of phase transfer catalyst such as 18-crown-6-ether in a solvent such as toluene or xylene or acetone or ethyl methyl ketone at a temperature ranging from 20° C. to 35° C.

Compound 17-b is oxidized under standard condition using either NCS and DMS oxidizing species (Kim Corey reagent) or with Dess-Martin periodinane reagent, in a suitable solvent such as dichloromethane or dichloroethane or chloroform at a temperature ranging from −50° C. to 10° C. to provide a benzyl ether amidoxime ketolide compound 17-c. The compound 17-c is fluorinated by reacting it with fluorinating agent such as N-Fluorodibenzenesulfnimide (NFSI) or select-fluor, in the presence of base such as lithium t-butoxide or sodium t-butoxide in a suitable solvent such as N,N-dimethylformamide (DMF) or N,N-dimethylacetamide (DMAC) or tetrahydrofuran (THF), at a temperature ranging from −40° to 0° C. to provide corresponding fluorinated ketolide compound 17-d, which is further subjected to hydrogenolysis using 20% palladium hydroxide or 10% palladium on carbon or a mixture thereof and in the presence of hydrogen source such as hydrogen gas under pressure in solvent such as methanol or ethanol or ethyl acetate or mixture thereof at a temperature ranging from 20° C. to 50° C. to provide fluorinated ketolide compound 17-e.

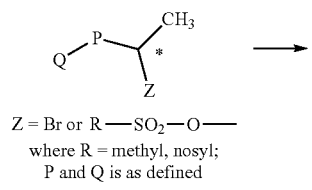

Z = Br or R—SO$_2$—O—
where R = methyl, nosyl;
P and Q is as defined

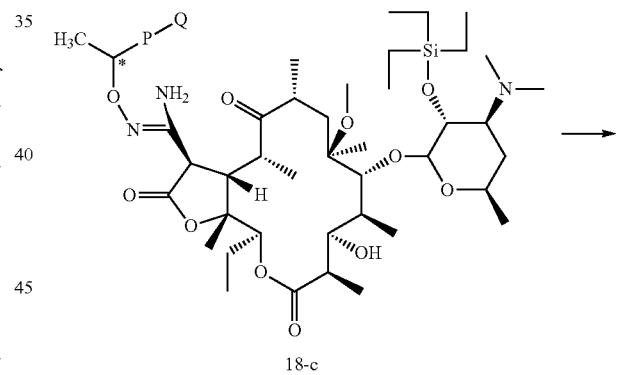

18-c

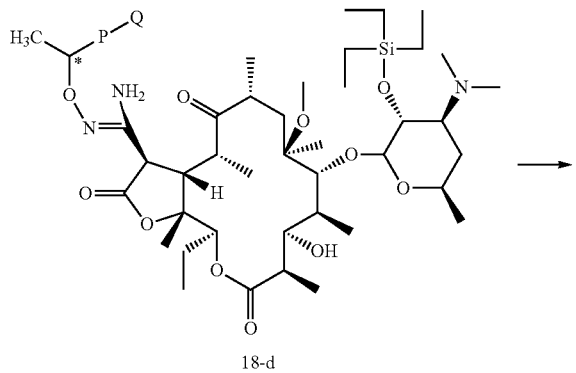

18-d

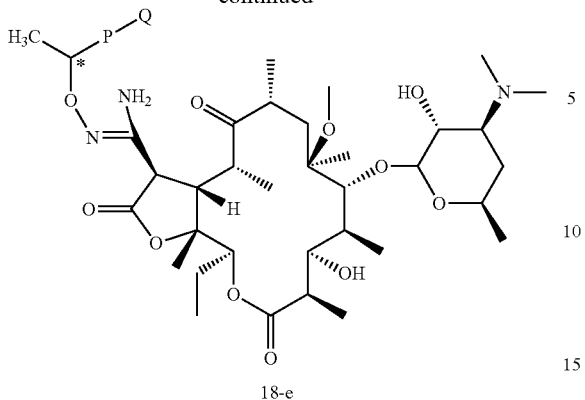

18-e

As per scheme-18, amidoxime compound of formula 18-a, is reacted with racemic or enantiomerically pure appropriate bromide, mesylate, tosylate or nosylate derivative of formula 18-b in the presence of suitable organic base such as potassium hydride or potassium tertbutoxide or inorganic base such as potassium hydroxide with phase transfer catalyst such as 18-crown-6 ether in a suitable solvent such as toluene at a temperature ranging from −10° C. to 50° C. to provide ether derivative of formula 18-c.

It is then oxidized under Corey-Kim oxidizing conditions (made from NCS and DMS) or with Dess-Martin periodinane reagent, in a suitable solvent such as dichloromethane or dichloroethane or chloroform, at a temperature ranging from −50° C. to 10° C. to provide a 2'-O-triethylsilyl protected ketolide of formula 18-d.

It is in turn reacted with suitable silyl deprotecting agent such as pyridine-hydrogenfluoride, tetrabutylammonium fluoride, aqueous hydrochloric acid, in a suitable solvent such as acetonitrile or tetrahydrofuran or dioxane at a temperature ranging from 0° C. to 40° C. to provide ketolide derivative of Formula (18-e).

Optionally, ketolide of formula 18-e (when ring Q bears a substituent like Boc-NH) is treated with pyridine-hydrogenfluoride or trifluoro acetic acid in acetonitrile to provide corresponding amino derivative.

Optionally, compound 18-e (when ring Q bears a substituent like OBn) is subjected to hydrogenolysis using palladium on carbon under hydrogen pressure in solvent such as methanol to provide corresponding hydroxyl derivative.

Scheme-19

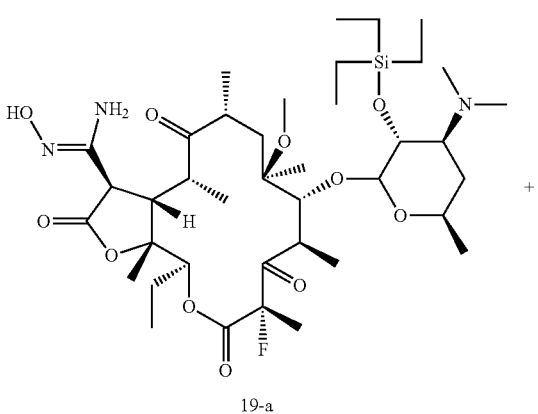

19-a

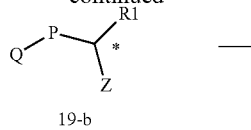

19-b

Z = Br or R—SO$_2$—O—
where R = methyl, nosyl;
19-b = R1 = H; 19-b' = R1 = CH$_3$
P and Q is as defined

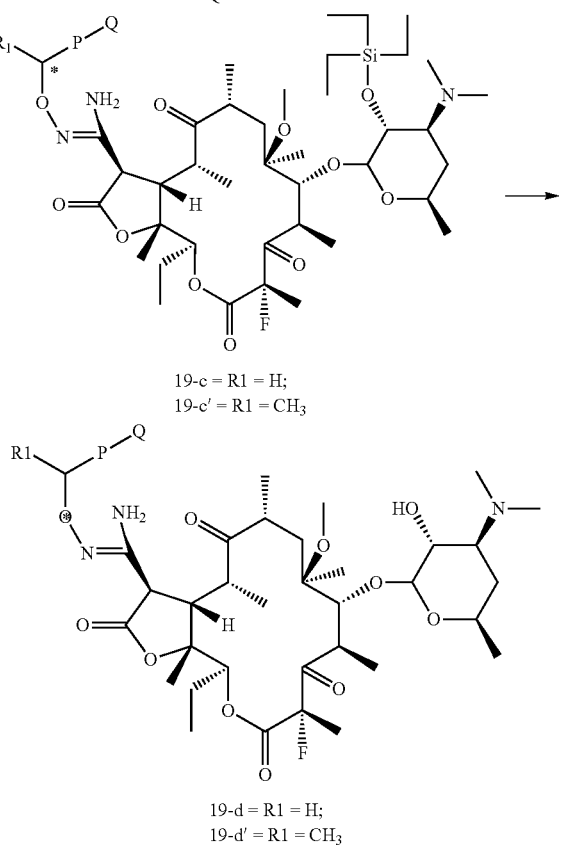

19-c = R1 = H;
19-c' = R1 = CH$_3$ 19-d = R1 = H;
19-d' = R1 = CH$_3$

As per scheme-19, amidoxime compound 19-a, is reacted with racemic or enantiomerically pure appropriate bromide, mesylate, tosylate or nosylate derivative of heteroaryl of formula 19-b in the presence of suitable organic base such as potassium hydride or potassium tertbutoxide or inorganic base such as potassium hydroxide with phase transfer catalyst such as 18-crown-6 ether in a suitable solvent such as toluene at a temperature ranging from −10° C. to 50° C. to provide corresponding ether derivative of formula 19-c.

Which is then reacted with suitable silyl deprotecting agent such as pyridine-hydrogenfluoride, tetrabutylammonium fluoride, aqueous hydrochloric acid, in a suitable solvent such as acetonitrile or tetrahydrofuran or dioxane at a temperature ranging from 0° C. to 40° C. to provide the 19-d.

Additionally, compound 19-d' is prepared in a similar manner reacting 19-a with 19-b' to provide 19-c', followed by converting 19-c' to 19-d'.

Optionally, compound 19-d or 19-d' (when ring Q bear a substituent like Boc-NH or di-Boc-N) is treated with pyridine-hydrogenfluoride or trifluoro acetic acid in acetonitrile to provide corresponding amino derivative.

Optionally, compound 19-d or 19-d' (when ring Q bear a substituent like OBn) is subjected to hydrogenolysis using palladium on carbon under hydrogen pressure in solvent such as methanol to provide corresponding hydroxyl derivative.

EXPERIMENTAL

Preparation 1

2-(5-Bromomethyl-isoxazol-3-yl)-pyridine

Step-1: Pyridin-2-imidoyl chloride

To a mixture of ethyl 2-pyridin-aldoxime (15 gm) and N-chlorosuccinamide (25 gm) in DMF (30 ml) was stirred at 30° C. over a period of 2 h. The reaction mixture was quenched with ice-cold water (150 ml). The suspension was filtered and the wet cake washed with small quantity of water to provide pure title compound in 7 gm quantity (55%) as a white solid.
Mass: m/z: 157 (M+1)

Step-2: 2-(5-Ethoxycarbonyl-isoxazol-3-yl)-pyridine

To a mixture of pyridin-2-imidoyl chloride (15 gm), triethylamine (25 ml) in toluene (150 ml) was added ethyl propiolate (10 gm) stirred at 30° C. over a period of 0.5 h. The reaction was monitored by TLC. The reaction mixture was quenched with water (100 ml). The layers were separated. The organic layer was dried over sodium sulfate. It was evaporated under vacuum to provide a crude mass. Crude mass was purified by using silica gel column chromatography to provide title compound in 8.2 gm quantity (62%) as a liquid. The compound was characterized by proton NMR.
$H^1$-NMR (CDCl$_3$) δ: 1.39-1.42 (t, 3H), 4.41-4.46 (q, 2H), 7.34-7.37 (m, 1H), 7.55 (s, 1H), 7.78-7.82 (dt, 1H), 8.08-8.1 (d, 1H), 8.67-8.68 (d, 1H).

Step-3: 2-(5-Hydroxymethyl-isoxazol-3-yl)-pyridine

To a mixture of 2-(5-ethoxycarbonyl-isoxazol-3-yl)-pyridine (6.5 gm), in ethanol (80 ml) was added sodium borohydride (2 gm) in lots at 30° C. It was stirred at 30° C. over a period of 1.5 h. The reaction was monitored by TLC. Upon consumption of starting material, aqueous ammonium chloride solution was added. The mixture was extracted with ethyl acetate. Combined organic layers was washed with water and concentrated under vacuum to provide title compound in 7.7 gm quantity. It was purified by using silica gel column chromatography to afford tile compound in 4.5 g (85%) quantity as off-white solid.
$H^1$-NMR (DMSO) δ: 4.61-4.63 (d, 2H), 5.68-5.71 (t, 1H), 6.86 (s, 1H), 7.46-7.49 (m, 1H), 7.90-7.94 (m, 1H), 7.98-8.0 (d, 1H), 8.68-8.69 (d, 1H).

Step-4: 2-(5-Methanesulfonyloxymethyl-isoxazol-3-yl)-pyridine

To a mixture of 2-(5-hydroxymethyl-isoxazol-3-yl)-pyridine (4.0 gm), and triethylamine (6.5 ml) in dichloromethane (40 ml) was added methanesulfonyl chloride (2.8 ml) at 0° C. The reaction mixture was stirred at 0° C. over a period of 1 h. The reaction was quenched by addition of water and layers were separated. Aqueous layer was extracted with dichloromethane (40 ml×2). Combined organic layer was washed with aqueous sodium bicarbonate solution followed by water and evaporated under vacuum to provide the title compound in 5.1 gm quantity (84%) as a semisolid, which was used without purification for the next reaction.

Step-5: 2-(5-Bromomethyl-isoxadiazol-3-yl)-pyridine

A mixture of 2-(5-methanesulfonyloxymethyl-isoxazol-3-yl)-pyridine (5.0 gm), lithium bromide (3.4 gm) in acetone (50 ml) was stirred at reflux temperature over a period of 2 h. The reaction mixture was evaporated under vacuum to provide a crude mass, which was triturated with chilled water (50 ml) to provide a suspension. The suspension was filtered at suction to afford the title compound in 3.1 gm quantity (85%).
Mass: m/z: 255.1 (M+2).

Preparation 2

2-(3-Bromomethyl-isoxazol-5-yl)-pyrimidine

Step-1: 2-(3-Ethoxycarbonyl-isoxazol-5-yl)-pyrimidine

To a mixture of 2-ethynyl-pyrimidine (28 gm) and ethyl-chlorooxamidoacetate (45 gm) in toluene (340 ml) was added triethylamine (42 ml) at 90° C., and it was stirred for 0.5 h. The reaction was monitored by TLC. Reaction was allowed to cool at 30° C. and water was added. Organic layers were separated. Organic layer was evaporated under vacuum and the crude mass was triturated with n-hexane. The suspension was filtered and the wet cake washed with small quantity of n-hexane to provide title compound in 35.1 gm quantity (59%) as a cream colored solid.
Mass: m/z: 220.1 (M+1)

Step-2: 2-(3-Hydroxymethyl-isoxazol-5-yl)-pyrimidine

To a mixture of 2-(3-ethoxycarbonyl-isoxazol-5-yl)-pyrimidine (35 gm) in 2:1 v/v ethanol:THF mixture (525 ml) was added sodium borohydride (7.5 gm) in lots at 0° C. It was stirred at 30° C. temperature over a period of 4 h. The reaction mixture was evaporated under vacuum to provide a residue and to the residue, (150 ml) was added. The suspension was extracted with ethyl acetate (4.5 ltr). Combined organic layers was washed with water and concentrated under vacuum to provide crude mass in 23 gm quantity, which was recrystallized from ethanol to provide the title compound in 15.1 gm quantity (53%) as pale yellow solid.
Mass: m/z: 178.1 (M+1)

Step-3: 2-(3-Methanesulfonyloxymethyl-isoxazol-5-yl)-pyrimidine

To a mixture of 2-(3-hydroxymethyl-isoxazol-5-yl)-pyrimidine (14 gm) and triethylamine (22 ml) in dichloromethane (400 ml), was added methanesulfonyl chloride (7.2 ml) at 0° C. The reaction mixture was stirred at 0° C. over a period of 0.5 h. The reaction was quenched by addition of water and layers were separated. Organic layer was evaporated under vacuum to provide title compound in 19.7 gm quantity (97.7%) as a yellow solid. This was used as such for the next reaction.

Step-4: 2-(3-Bromomethyl-isoxazol-5-yl)-pyrimidine

A mixture of 2-(3-methanesulfonyloxymethyl-isoxazol-5-yl)-pyrimidine (19 gm), lithium bromide (13 gm) in acetone (190 ml) was stirred at 30° C. temperature over a period of 2 h. The reaction was monitored by TLC. The reaction mixture was evaporated under vacuum to provide a crude mass which upon stirring with water (150 ml) provided suspension. Filtration of suspension under suction afforded the title compound in 15.2 gm quantity (75.3%) as a solid.

Mass: m/z: 239.9 and 241.9 (M+1)

Preparation 3

2-(5-Bromomethyl-1,3,4-thiadiazol-2-yl)-pyridine

Step-1: Pyridin-2-carboxylic acid hydrazide

A mixture of ethyl pyridin-2-carboxylate (90 gm) and hydrazine (60 gm) in ethanol (400 ml) was stirred at 80° C. over a period of 4 h. Solvent was evaporated under vacuum to provide a crude mass. The crude mass was stirred with diethyl ether and the suspension was filtered and the wet cake washed with small quantity of ethanol (50 ml) to provide title compound in 76 gm quantity (93%) as a white solid.

Mass: m/z: 138 (M+1).

Step-2: 2-(5-Ethoxycarbonyl-1,3,4-thiadiazol-2-yl)-pyridine

To a mixture of pyridin-2-carboxylic acid hydrazide (76 gm), triethylamine (155 ml) in dichloromethane (600 ml) was added mono ethyl oxalyl chloride (80 gm) over a period of 0.5 h at 0° C. The reaction mixture was stirred for 2 h. The reaction was quenched by addition of water (100 ml), layers were separated and organic layer was washed with aqueous sodium bicarbonate solution (100 ml). Organic layer was evaporated in vacuum to provide crude mass in 110 gm quantity. To a crude mass in tetrahydrofurane (500 ml) was added Lowesson's reagent (208 gm) and the mixture was stirred at 60° C. over a period of 4 h. Solvent was evaporated and the crude mass was triturated with dicholomethane ether mixture. The suspension was filtered and the wet cake washed with small quantity of methanol (100 ml) to provide title compound in 45 gm quantity (35% after 2 steps) as off white solid.

$H^1$-NMR (CDCl$_3$) δ: 1.37-1.38 (t, 3H), 4.30-4.38 (q, 2H), 7.51-7.54 (m, 1H), 7.89-7.92 (m, 1H), 8.26-8.28 (d, 1H), 8.59-8.60 (d, 1H). Mass: m/z: 236 (M+1).

Step-3: 2-(5-Hydroxymethyl-1,3,4-thiadiazol-2-yl)-pyridine

To a mixture of 2-(5-ethoxycarbonyl-1,3,4-thiadiazol-2-yl)-pyridine (8 gm) in ethanol (80 ml), was added sodium borohydride (2.51 gm) in lots at 30° C. It was stirred at 30° C. over a period of 2 h. The solvent was evaporated under vacuum to provide a crude mass. To the crude mass, water (100 ml) was added and it was extracted with dichloromethane (200 ml×2). Combined organic layers was washed with water and concentrated under vacuum to provide title compound in 6.1 gm quantity (92%).

$H^1$-NMR (CDCl$_3$) δ: 4.87-4.88 (d, 2H), 6.264- 6.26 (bs, 1H), 7.54-7.57 (m, 1H), 7.98-8.02 (m, 1H), 8.22-8.24 (d, 1H), 8.67 (d, 1H). Mass: m/z: 194 (M+1).

Step-4: 2-(5-Methanesulfonyloxymethyl-1,3,4-thiadiazol-2-yl)-pyridine

To a mixture of 2-(5-hydroxymethyl-1,3,4-thiadiazol-2-yl)-pyridine (6 gm), and triethylamine (13.1 ml) in dichloromethane (150 ml) was added methanesulfonylchloride (5.31 gm) at 0° C. The reaction mixture was stirred at 0° C. over a period of 1 h. The reaction was quenched by addition of water and layers were separated. Aqueous layer was extracted with dichloromethane (50 ml×2). Combined organic layer was washed with aqueous sodium bicarbonate solution followed by water and evaporated under vacuum to provide title compound in 7.5 gm quantity (88%) as oil.

Mass: m/z: 272 (M+1).

Step-5: 2-(5-Bromomethyl-1,3,4-thiadiazol-2-yl)-pyridine

A suspension of 2-(5-methansulfonuloxymethyl-1,3,4-thiadiazol-2-yl)-pyridine (7.5 gm), lithium bromide (3.84 gm) in acetone (75 ml) was stirred at reflux temperature over a period of 1 h. The reaction was monitored by TLC. The reaction mixture was evaporated under vacuum to provide a crude mass. Crude mass was stirred with ice-cold water to provide a suspension. The solid was filtered under suction to afford the title compound in 6.5 gm quantity (92%) as a light brownish solid.

$H^1$-NMR (CDCl$_3$) δ: 5.16 (s, 1H), 7.57-7.6 (m, 1H), 8.01-8.04 (m, 1H), 8.24-8.26 (d, 1H), 8.69-8.7 (d, 1H); Mass: m/z: 255 (M−1).

Preparation 4

2-Bromomethyl-5-isoxazol-3-yl-pyrimidine

Step-1: 2-Methyl-5-formyl-pyrimidine

To a mixture of vinamidium diperchlorate salt (310 gm, prepared as per procedure described in Collection Czechoslov Chem. Commun Vol. 30, 1965) and acetamidine hydrochloride (106 gm) in actonitrile (2.5 L) at 30° C. was added w/v 50% aqueous sodium hydroxide (96.8 gm dissolved in 97 ml water) solution drop wise over a period of 2 h under stirring. The suspension was stirred for 3 h and pH of the reaction mixture was adjusted to 7 by addition of acetic acid (~147 ml). The solid was filtered and washed with acetonitrile (750 ml). The filtrate was evaporated under vacuum to provide a residue. The residue was stirred with water (750 ml) and the mixture was extracted with dichloromethane (300 ml×5). The layers were separated and organic layer was evaporated to provide title compound in 52 gm quantity (52%) as a low melting solid.

$H^1$NMR: (DMSO-d$_6$) δ 11.08 (bs, 1H), 10.08 (s, 1H), 9.09 (s, 2H), 2.69 (s, 3H).

Step-2: 2-Methyl-pyrimidine-5-carbaldehyde oxime

To a mixture of 2-methyl-5-formyl-pyrimidine (180 gm) and hydroxylamine hydrochloride (128 gm) in 50% v/v aqueous methanol (3600 ml) was added sodium carbonate (94 gm). The reaction mixture was stirred at 30° C. for 0.5 h. The resulting suspension was cooled and filtered at −10° C. to provide single isomer of title compound in 113.5 gm quantity (56%) as a solid.

$H^1$NMR: (DMSO-d$_6$) δ 11.64 (s, 1H), 8.83 (s, 2H), 8.14 (s, 1H), 2.60 (s, 3H).

Further processing of the filtrate such as evaporation and salt removal, provided a mixture of isomers in 51 gm quantity which can be used for the next reaction.

Step-3: 2-Methyl-5-(5-trimethylsilylethynyl-isoxazol-3-yl)-pyrimidine

To a solution of 2-methyl-pyrimidine-5-carbaldehyde oxime (145 gm) in DMF (435 ml) was added N-chlorosuccinamide (169.6 gm) in portions at 30° C. for 0.5 h. As the TLC indicated completion of the reaction, diethyl ether (1450 ml) was added. The reaction mixture was cooled to −5° to 0° C. To a cooled reaction mixture, was added triethylamine (589 ml) followed by trimethylsilylacetylene (450 ml). The mixture was stirred at −5° C. for additional 1 h. The solid separated was filtered at suction. Filtrate was washed with water (300 ml×4) followed by brine solution (500 ml) and organic layer was concentrated under vacuum to provide a solid in 158 gm quantity which was used as it is for further reaction.

Step-4: 2-Methyl-5-isoxazol-3-yl-pyrimidine

To a mixture of 2-methyl-5-(5-trimethylsilylethynyl-isoxazol-3-yl)-pyrimidine (158 gm) in methanol (1450 ml) was added sodiumbicarbonate (177 gm). The reaction mixture was stirred at 40° C. up to 1 hr. The reaction mixture was filtered. The solid obtained was washed with ethyl acetate and the filtrate was evaporated under vacuum to provide a residue. The residue was stirred with water (800 ml) and extracted with dichloromethane (500 ml×3). The layers were separated and the organic layer was evaporated to provide a residue (133 gm) which upon silica gel column chromatography afforded title compound in 79 gm quantity in 46.4% yield after three steps.

$H^1$NMR: (DMSO-$d_6$) δ 9.15 (s, 2H), 9.09 (d, 1H), 7.27 (d, 1H), 2.67 (s, 3H); Mass: m/z: 162 (M+1).

Step-5: 2-Bromomethyl-5-isoxazol-3-yl-pyrimidine

A mixture of 2-methyl-5-isoxazol-3-yl-pyrimidine (30 gm), N-bromosuccinamide (49.8 gm), and 98% benzoyl peroxide (13.54 gm) in carbon tetrachloride (1200 ml) was heated to 75° C. temperature. The reaction mixture was stirred at 75° C. for 24 h. The reaction mixture was filtered under suction at 25° C. to 35° C. temperature. The solid was washed with carbon tetrachloride (400 ml). The filtrate was washed with saturated aqueous sodium bicarbonate solution (400 ml×2) and evaporated under vacuum to provide a crude material (52 gm) which upon silica gel column chromatography afforded desired compound in 14 gm quantity (40%), dibromo compound in 16.8 gm and starting material 6.5 gm quantities.

$H^1$NMR: (DMSO-$d_6$) δ 9.30 (s, 2H), 9.13 (s, 1H), 7.32 (d, 1H), 4.74 (s, 2H).

Preparation 5

2-di-(tert-butyloxy-carbonyl)-amino-6-(2-bromomethyl-pyridin-6-yl)-pyridine

Step-1: 2-Di-(tert-butyloxy-carbonyl)-amino-6-tributylstannyl-pyridine

A solution of 2-bromo-6-N,N-di-t-butyloxy-carbonyl-amino-pyridine (13 gm) in dimethoxyethane (260 ml) was added hexabutyldistannane (20.21 gm), followed palladium-tetrakis(triphenylphosphine) (2.01 gm) at 25° C., and the resulting mixture was degassed for 30 min. The reaction mixture was heated under stirring at a temperature 80° C. for 24 hours. The reaction mixture was cooled to ambient temperature and filtered through celite. The filtrate was stirred with water (250 ml) and extracted with ethyl acetate (150 ml×3). The combined organic extract was washed with water (100 ml×2), dried over $Na_2SO_4$. The evaporation of solvents under vacuum afforded titled product as an oil (17.8 gm) in 87% yield, which was used as such for the next reaction.

Mass: m/z (M+H): 584.1

Step-2: 2-Di-(tert-butyloxy-carbonyl)-amino-6-(2-formyl-pyridin-6-yl)-pyridine A suspension of 2-di-(tert-butyloxy-carbonyl)-amino-6-tributylstannyl-pyridine (15.3 gm), 2-bromo-pyridine-6-carbaldehyde (7.0 gm), triethyl amine (10.60 gm), palladium-tetrakis(triphenylphosphine) (1.51 gm) and lithium chloride (2.9 gm), in toluene (140 ml), was degassed for 0.5 hr at 25° C. The suspension was heated at reflux for 6 hours. The reaction mixture was cooled to ambient temperature and filtered through celite. The filtrate was stirred with water (250 ml) and extracted with ethyl acetate (100 ml×2). The combined organic extracts was dried over $Na_2SO_4$, and evaporated under vacuum. The resulting crude mass was purified by using silica gel column chromatography (ethyl acetate/hexane) to yield title compound in 2.0 gm quantity in 19.1% yield.

Mass m/z (M+H): 400.1.

Step-3: 2-Di-(tert-butyloxy-carbonyl)-amino-6-(2-hydroxy-methyl-pyridin-6-yl)-pyridine A solution of 2-di-(tert-butyloxy-carbonyl)-amino-6-(2-formyl-pyridin-6-yl)-pyridine (1.9 gm) in tetrahydrofuran:methanol mixture (1:1, 20 ml) was treated with sodium borohydride (200 mg) in portions at a temperature between 25° C. to 35° C. As the TLC showed the complete consumption of starting material, it was concentrated under vacuum. The crude mass was stirred with water (25 ml) and extracted with ethyl acetate (50 ml×2). The combined organic extract was washed with saturated sodium bicarbonate solution (25 ml×2) followed by brine solution (25 ml). The organic layer was dried over $Na_2SO_4$, and concentrated under vacuum to provide a crude mass. It was purified by using silica gel column chromatography (ethyl acetate/hexane) to afford the tile compound in 1.5 gm quantity in 79% yield.

Mass: m/z: $(M+H)^+$: 402.1.

Step-4: 2-Di-(tert-butyloxy-carbonyl)-amino-6-(2-methanesulfonyloxy-methyl-pyridin-6-yl)-pyridine A solution of 2-di-(tert-butyloxy-carbonyl)-amino-6-(2-hydroxy-methyl-pyridin-6-yl)-pyridine (1.5 gm) and triethylamine (1.13 gm) in dichloromethane (15 ml) was cooled to −5° C. and treated with methanesulfonyl chloride (0.395 gm). As TLC showed completion of the reaction, to it was added water (10 ml) followed by dichloromethane (50 ml). The organic layer was separated and washed with water (25 ml×2), dried over $Na_2SO_4$, and concentrated under vacuum to provide title compound in 1.6 gm quantity in 90% yield, which was used as such for the next reaction.

Mass: m/z: (M+1): 480.1.

Step-5: 2-Di-(tert-butyloxy-carbonyl)-amino-6-(2-bromomethyl-pyridin-6-yl)-pyridine A suspension of 2-di-(tert-butyloxy-carbonyl)-amino-6-(2-methanesulfonyloxy-methyl-pyridin-6-yl)-pyridine (1.6 gm) and lithium bromide (435 mg) in acetone (17 ml) was heated at a reflux temperature for 3 hours. As TLC showed completion of reaction, the reaction mixture was cooled to ambient temperature. The suspension was filtered under suction and concentrated under vacuum. The obtained residue was stirred with water (25 ml) and extracted with ethyl acetate (30 ml×2). The combined organic extracts was washed with saturated brine solution (25 ml), and dried over Na$_2$SO$_4$. The organic layer was concentrated under vacuum to provide a crude mass, which was purified by using silica gel column chromatography (ethyl acetate/hexane) to provide title compound in 1.1 gm quantity in 70% yield.

Mass: m/z (M+H): 465.2.

Preparation 6

(RS)-2-(5-(1-Bromoethyl)-isoxazol-3-yl)-pyridine

Step-1: Pyridin-2-imidoyl chloride

To a mixture of pyridin-2-carbaldehyde-oxime (15 gm) and N-chlorosuccinamide (25 gm) in DMF (30 ml) was stirred at 30° C. over a period of 2 h. The reaction mixture was quenched with ice cold water (150 ml). The suspension was filtered and the wet cake washed with small quantity of water to provide pure title compound in 7 gm quantity (55%) as a white solid.

Mass: m/z: 157 (M+1)

Step-2: 2-(5-Ethoxycarbonyl-isoxazol-3-yl)-pyridine

To a mixture of pyridin-2-imidoyl chloride (15 gm), triethylamine (25 ml) in toluene (150 ml) was added ethyl propiolate (10 gm) stirred at 30° C. over a period of 0.5 h. The reaction was monitored by TLC. The reaction mixture was quenched with water (100 ml). The layers were separated. The organic layer was dried over sodium sulfate. It was evaporated under vacuum to provide a crude mass. Crude mass was purified by silica gel column chromatography to provide title compound in 8.2 gm quantity (62%) as a liquid.

H$^1$-NMR (CDCl$_3$) δ: 1.39-1.42 (t, 3H), 4.41-4.46 (q, 2H), 7.34-7.37 (m, 1H), 7.55 (s, 1H), 7.78-7.82 (dt, 1H), 8.08-8.1 (d, 1H), 8.67-8.68 (d, 1H).

Step-3: 2-(5-Hydroxymethyl-isoxazol-3-yl)-pyridine

To a mixture of 2-(5-ethoxycarbonyl-isoxazol-3-yl)-pyridine (6.5 gm), in ethanol (80 ml) was added sodium borohydride (2 gm) in lots at 30° C. It was stirred at 30° C. over a period of 1.5 h. The reaction was monitored by TLC. Upon consumption of ethyl ester, aqueous ammonium chloride solution was added. The mixture was extracted with ethyl acetate. Combined organic layers was washed with water and concentrated under vacuum to provide title compound in 7.7 gm quantity. It was purified by silica gel column chromatography to afford tile compound in 4.5 g (85%) quantity as a off-white solid.

H$^1$-NMR (DMSO) δ: 4.61-4.63 (d, 2H), 5.68-5.71 (t, 1H), 6.86 (s, 1H), 7.46-7.49 (m, 1H), 7.90-7.94 (m, 1H), 7.98-8.0 (d, 1H), 8.68-8.69 (d, 1H).

Step-4: 2-(5-formyl-isoxazol-3-yl)-pyridine

To a mixture of 2-(5-hydroxymethyl-isoxazol-3-yl)-pyridine in dichloromethane (30 ml) was added Des-Martin periodanane reagent (15% solution in DCM, 51 ml) at 30° C. The reaction mixture was stirred at 30° C. over a period of 0.5 h. The reaction was monitored by TLC. The reaction was quenched by addition of 1:1 sodiumthiosulfate and sodiumbicarbonate aqueous solution. The layers were separated. Aqueous layer was extracted with dichloromethane. Combined organic layer was evaporated under vacuum to provide title aldehyde in 3 gm quantity (quantitative).

H$^1$-NMR (CDCl$_3$) δ: 7.61 (s, 1H), 7.66-7.7 (t, 1H), 7.98-8.1 (d, 1H), 8.68-8.7 (d, 1H), 10.01 (s, 1H).

Step-5: (RS)-2-(5-(1-Hydroxyethyl)-isoxazol-3-yl)-pyridine

To a mixture of 2-(5-formyl-isoxazol-3-yl)-pyridine (3 gm) in THF (30 ml) was added methyl magnesium iodide (19 ml, 1.4 M solution in THF) at 0° C. over a period of 15 minutes. The reaction was stirred for 1.5 h and monitored by TLC. The reaction was quenched by addition of aqueous ammonium chloride solution (20 ml) and extracted with ethyl acetate (100 ml×2). Combined organic layers was washed with water and evaporated under vacuum to provide 1.9 gm crude mass, which was purified by using silica gel column chromatography to provide a title compound in 1.0 gm quantity (42%) as a solid.

H$^1$-NMR (CDCl$_3$) δ: 1.62-1.64 (d, 3H), 3.14 (s, 1H), 5.04-5.07 (q, 1H), 6.86 (s, 1H), 7.33-7.36 (m, 1H), 7.77-7.81 (dt, 1H), 8.03-8.05 (d, 1H), 8.66-8.68 (d, 1H).

Step-6: (RS)-2-(5-(1-Bromoethyl)-isoxazol-3-yl)-pyridine

To a mixture of (RS)-2-(5-(1-hydroxy-ethyl)-isoxazol-3-yl)-pyridine (0.9 gm), and triphenylphosphene (1.77 gm) in dichloromethane (20 ml) was added carbontetrabromide (6 gm) at 0° C. The reaction mixture was stirred at 30° C. over a period of 2.5 h. The reaction was monitored by TLC. The reaction was quenched by addition of water and layers were separated. Combined organic extract was washed with brine and evaporated under vacuum to provide the 1.7 gm crude mass which was purified by using silica gel column chromatography to provide title compound in 0.8 gm quantity (65%).

H$^1$-NMR (CDCl$_3$) δ: 2.09-2.11 (d, 3H), 5.2-5.25 (q, 1H), 6.94 (s, 1H), 7.32-7.36 (m, 1H), 7.76-7.81 (m, 1H), 8.05-8.08 (t, 1H), 8.66-8.67 (d, 1H); Mass: M+1=254.1.

Preparation 7

(RS)-2-(3-(1-bromo-ethyl)-isoxazol-5-yl)-pyrimidine

Step-1: 2-(3-Ethoxycarbonyl-isoxazol-5-yl)-pyrimidine

To a mixture of 2-ethynyl-pyrimidine (28 gm) and ethylchlorooxamidoacetate (45 gm) in toluene (340 ml) was added triethylamine (42 ml) at 90° C., and it was stirred for 0.5 h. The reaction was monitored by TLC. Reaction was allowed to cool at 30° C. and water added. Organic layer was separated. Solvent was evaporated under vacuum and the crude mass was triturated with n-hexane. The suspension was filtered and the wet cake washed with small quantity of n-hexane to provide title compound in 35.1 gm quantity (59%) as a cream colored solid.

Mass: m/z: 220.1 (M+1).

Step-2: 2-(3-(1-Oxo-ethyl)-isoxazol-5-yl)-pyrimidine

To a mixture of THF: toluene (6.5 ml: 5 ml) was added triethylamine (16.3 ml) followed by methyl magnesium iodide (28.6 ml, 1.4 M solution in THF) at 0° C. To the reaction mixture, was added 2-(3-ethoxycarbonyhisoxazol-5-yl)-pyrimidine (2.0 gm) dissolved in toluene (35 ml) in at 0° C. over a period of 15 minutes. The reaction was stirred for 2 h. It was quenched by addition of 1N aqueous hydrochloric acid (43 ml). It was extracted with toluene. Combined organic layers was washed with saturated sodium bicarbonate solution followed by water. Organic layer was evaporated under vacuum to provide a crude mass which upon purification by using silica gel column chromatography provided title compound in 1.2 gm quantity (70%) as solid.

H$^1$NMR: (DMSO-d$_6$) δ 9.00 (d, 2H), 7.62 (t, 1H), 7.41 (s, 1H), 2.63 (S, 3H).

Step-3: (RS)-2-(3-(1-Hydroxyethyl)-isoxazol-5-yl)-pyrimidine

To a mixture of 2-(3-(1-oxo-ethyl)-isoxazol-5-yl)-pyrimidine (1.2 gm) in methanol (20 ml) was added sodium borohydride (0.485 gm) in lots at 0° C. It was stirred at 30° C. over a period of 2 h. The reaction mixture was evaporated under vacuum to provide a residue. The residue was stirred with water and extracted with ethyl acetate (25 ml X3). Combined organic layers was washed with aqueous sodium bicarbonate solution followed by water and concentrated under vacuum to provide title compound in 1.1 gm quantity (91%). It as used as without purification for the next reaction.

Step-4: (RS)-2-(3-(1-Bromoethyl)-isoxazol-5-yl)-pyrimidine

A mixture of (RS)-2-(3-(1-hydroxymethyl)-isoxazol-5-yl)-pyrimidine (1.1 gm), in dichloromethane (20 ml) was added carbon tetrabromide (7.64 gm) followed by triphenylphosphine (1.8 gm) at 0° C. The reaction mixture was stirred at 0° C. for 0.5 h and at 30° C. for 2 h. The reaction mixture evaporated under vacuum to provide a crude mass, which upon silica gel column chromatography afforded the title compound in 0.7 gm quantity (50%) as a solid.

H$^1$NMR: (DMSO-d$_6$) δ 8.96 (d, 2H), 7.59-7.61 (t, 1H), 7.42 (s, 1H), 5.51-5.56 (q, 1H), 2.01-2.03 (d, 3H).

Preparation 8

(RS)-2-[5-(1-Bromoethyl)-1,3,4-thiadiazol-2-yl]-pyridine

Step-1: Pyridin-2-carboxylic acid hydrazide

A mixture of ethyl pyridin-2-carboxylate (90 gm) and hydrazine (60 gm) in ethanol (400 ml) was stirred at 80° C. over a period of 4 h. Solvent was evaporated and to provide a crude mass. The mass was stirred with diethyl ether and the suspension was filtered and the wet cake washed with small quantity of ethanol (50 ml) to provide title compound in 76 gm quantity (93%) as a white solid.

Mass: m/z: 138 (M+1).

Step-2: 2-(5-Ethoxycarbonyl-1,3,4-thiadiazol-2-yl)-pyridine

To a mixture of pyridin-2-carboxylic acid hydrazide (76 gm), triethylamine (155 ml) in dichloromethane (600 ml) was added mono ethyl oxalyl chloride (80 gm) over a period of 0.5 h at 0° C. The reaction mixture was stirred for 2 h. The reaction was monitored by TLC. The reaction was quenched by addition of water (100 ml), layers were separated and organic layer was washed with aqueous sodiumbicarbonate solution (100 ml). Organic layer was evaporated in vacuum to provide crude mass in 110 gm quantity. To a crude mass in tetrahydrofuran (500 ml) was added Lowesson's reagent (208 gm) and the mixture was stirred at 60° C. over a period of 4 h. Solvent was evaporated and the crude mass was triturated with dicholomethane ether mixture. The suspension was filtered and the wet cake washed with small quantity of methanol (100 ml) to provide title compound in 45 gm quantity (35% after 2 steps) as off white solid.

H$^1$-NMR (CDCl$_3$) δ: 1.37-1.38 (t, 3H), 4.30-4.38 (q, 2H), 7.51-7.54 (m, 1H), 7.89-7.92 (m, 1H), 8.26-8.28 (d, 1H), 8.59-8.60 (d, 1H). Mass: m/z: 236 (M+1).

Step-3: 2-[5-(1-Oxo-ethyl)-1,3,4-thiadiazol-2-yl]-pyridine

To a mixture of 2-(5-ethoxycarbonyl-1,3,4-thiadiazol-2-yl)-pyridine (2 gm) in THF (40 ml) was added methyl magnesium iodide (15 ml, 1.4 M solution in THF) at −40° C. over a period of 15 minutes. The reaction mixture was stirred for 2 h at −40° C. It was quenched by addition of aqueous ammonium chloride solution (20 gm) and stirred at 0° C. over a period of 10 minutes. It was extracted with ethyl acetate (100 ml×2). Combined organic layers was washed with water and evaporated under vacuum to provide a title compound in 1.5 gm quantity (86%) as off white solid.

H$^1$-NMR (CDCl$_3$) δ: 2.84 (s, 3H), 7.25-7.46 (m, 1H), 7.86-7.9 (m, 1H), 8.39-8.41 (d, 1H), 8.67-8.68 (d, 1H); Mass: m/z: 206 (M+1).

Step-4: (RS)-2-[5-(1-Hydroxyethyl)-1,3,4-thiadiazol-2-yl]-pyridine

To a mixture of 2-[5-(1-oxo-ethyl)-1,3,4-thiadiazol-2-yl]-pyridine (1.5 gm), in methanol (25 ml) was added sodium borohydride (0.2 gm) in lots at 30° C. It was stirred over a period of 2 h. The reaction was monitored by TLC. Solvent was evaporated under vacuum and water (20 ml) was added. The mixture was extracted with ethyl acetate (100 ml×2). Combined organic layers was washed with water and concentrated under vacuum to provide title compound in 1.0 gm quantity (67%). It as used as without purification for the next reaction.

Mass: m/z: 208 (M+1).

Step-5: (RS)-2-[5-(1-Methanesulfonyloxy-ethyl)-1,3,4-thiadiazol-2-yl]-pyridine

To a mixture of (RS)-2-(5-(1-hydroxy-ethyl)-1,3,4-thiadiazol-2-yl)-pyridine (1.0 gm), and triethylamine (2 ml) in dichloromethane (50 ml) was added methanesulfonyl chloride (0.9 gm) at −10° C. The reaction mixture was stirred over a period of 1 h. The reaction was quenched by addition of water and layers were separated. Aqueous layer was extracted with dichloromethane. Combined organic layer was washed with aqueous sodium bicarbonate followed by water and evaporated under vacuum to provide the title compound in 1.0 gm quantity (73%) as an oil.

Mass: m/z: 286 (M+1).

Step-6: (RS)-2-[5-(1-Bromoethyl)-1,3,4-thiadiazol-2-yl]-pyridine

A mixture of (RS)-2-[5-(1-methanesulfonyloxy-ethyl)-1,3,4-thiadiazol-2-yl]-pyridine (1.0 gm), lithium bromide (0.5 gm) in acetone (20 ml) was stirred at reflux over a period of 1 h. The reaction mixture was evaporated under vacuum to provide a crude mass. Crude mass was stirred with ice cold water and extracted with dichloromethane (50 ml×2). The combined organic layer was evaporated under vacuum to afford the title compound in 0.8 gm quantity (85%) as oil.

H¹-NMR (CDCl$_3$) δ: 2.2 (d, 2H), 5.51-5.57 (q, 1H), 7.38-7.41 (m, 1H), 7.83-7.87 (m, 1H), 8.32-8.34 (d, 1H), 8.63-8.64 (d, 1H); Mass: m/z: 272 (M+2).

Preparation 9

(R)-2-[5-(1-Methanesulfonyloxy-ethyl)-1,3,4-thiadiazol-2-yl]-pyridine

Step-1: (R)-2-[5-(1-Hydroxy-ethyl)-1,3,4-thiadiazol-2-yl]-pyridine

To a mixture of (RS)-2-(5-(1-hydroxy-ethyl)-1,3,4-thiadiazol-2-yl)-pyridine (7.5 gm), and N,N-dimethyl aminopyridine (0.5 gm) and in was added (R)—O-acetyl-mandelic acid (7.1 gm) dichloromethane (150 ml) at −10° C. was added a solution of dicyclohexylcarbodiimide (11.19 gm) in dichloromethane (25 ml). The reaction mixture was stirred over a period of 1 h. The reaction mixture was filtered under suction and the filtrate was evaporated under vacuum to provide a residue which was purified by silica gel column chromatography to provide a mixture of two diastereomers in 10.0 gm quantity as a semi-solid.

HPLC ratio of diastereomer 2:diastereomer 1: 42.46:42.11. Mass: m/z: 384 (M+1)

The mixture of two diastereomers (10 gm) obtained as above was stirred in methanol (25 ml) to provide a clear solution. The reaction mixture was allowed stir at 25° C. for 0.5 h to provide precipitation. The solid was filtered at suction and the wet cake was washed with methanol (5 ml). The wet solid (5 gm) was suspended in methanol (15 ml). It was stirred for 0.5 h and filtered under suction to provide a solid. The solid was dried to provide diastereomer-2 in 3.8 gm quantity as a solid. Filtrate was enriched with diastereomer-1.

HPLC ratio of diastereomer-2:diastereomer-1 as a solid: 99.5:0.5

Mass: m/z: 384 (M+1). NMR (CDCl$_3$) δ: 1.79-1.81 (d, 3H), 2.23 (s, 3H), 5.96 (s, 1H), 6.29-6.33 (q, 1H), 7.55-7.58 (m, 1H), 7.76-7.80 (m, 1H), 7.91-7.93 (d, 1H), 8.01-8.04 (d, 1H).

HPLC ratio of diastereomer-2:diastereomer-1 (from filtrate): 21.23:56.35

Mass: m/z: 384 (M+1).

Chirally pure diastereomer-2 was obtained as above (3.8 gm) was dissolved in methanol (40 ml) and to the reaction mixture was added KOH (1.1 gm dissolved in 4 ml water) at −5° C. The reaction mixture was stirred at −5° C. for 2 h. Solvent was evaporated. pH of reaction mixture was adjusted between 4 to 5 using 2N aqueous hydrochloric acid. It was extracted with dichloromethane (100 ml×2). Combined organic layer was washed with saturated sodium bicarbonate solution. Layers were separated and evaporated under vacuum to provide chirally pure R enantiomer in 2.1 gm with chiral purity 99.11 by HPLC.

NMR (CDCl$_3$) δ: 1.42-1.6 (d, 3H), 5.19-5.24 (q, 1H), 7.45-7.48 (m, 1H), 7.86-7.91 (m, 1H), 8.13-8.15 (d, 1 H), 8.54 (bs, 1 H), 8.77-8.78 (d, 1 H). Mass: m/z: 208 (M+1). [α]D 25=+15.33° (c 0.5, CHCl$_3$).

Step-2: (R)-2-(5-Methanesulfonyloxymethyl-1,3,4-thiadiazol-2-yl)-pyridine

To a mixture of (R)-2-[5-(1-hydroxy-ethyl)-1,3,4-thiadiazol-2-yl]-pyridine (2.0 gm), and triethylamine (4.18 ml) in dichloromethane (100 ml) was added methanesulfonylchloride (1.6 gm) at −10° C. The reaction mixture was stirred at −10° C. over a period of 1 h. The reaction was quenched by addition of water and layers were separated. Aqueous layer was extracted with dichloromethane. Combined organic layer was washed with aqueous sodium bicarbonate solution followed by water and evaporated under vacuum to provide title compound in 2.4 gm quantity (87%) with chiral purity 98.66% by HPLC.

Mass: m/z: 286 (M+1)

Preparation 10

(R)-2-[5-(1-nosyloxy-ethyl)-1,3,4-thiadiazol-2-yl]-pyridine from methyl-D-lacate Step-1: Preparation of R-2-(tert-butyl-dimethylsilyloxy)-propionic acid hydrazide A mixture of R-2-(tert-butyl-dimethylsilyloxy)-propionic acid methyl ester (417 gm) and hydrazine (144 gm) in ethanol (400 ml) was stirred at 80° C. over a period of 4 h. Solvent was evaporated and to provide a crude mass. The crude mass was stirred with water (150 ml) and extracted with ethyl acetate (800 ml×2). The organic layer was dried on sodium sulfate and evaporated under vacuum to provide title compound in 417 gm quantity in quantitative yield as a liquid.

Mass: m/z: (M+1). 219.2, Purity by GC: 76.48% (RT-14.14)

Step-2: Preparation of R-pyridine-2-carboxylic acid N'-[2-(tert-butyl-dimethylsilyloxy)-propionyl]-hydrazide To a mixture of 2-picolinic acid (258 gm), R-2-(tert-butyl-dimethylsilyloxy)-propionic acid hydrazide (415 gm) in DMF (1000 ml) was added EDC hydrochloride (546 gm) followed by N-methyl morpholine (418 ml) over a period of 0.5 h at 0° C. to 5° C. HOBt (29 gm) was added in one lot. Additional DMF (245 ml) was added. The resulting suspension was stirred for 2 hr at 25° C. The reaction mixture was poured under stirring in water (7000 ml), and extracted with ethyl acetate (4000 ml×2). Combined organic layer was dried over sodium sulfate and concentrated in vacuum to provide syrup as a title compound in 602 gm quantity in 98% yield.

Mass (m/z) (M+1): 325.2.

Step-3: Preparation of R-2-{5-[1-(tert-butyl-dimethylsilyloxy)-ethyl]-1,3,4-thiadiazol-2-yl}-pyridine To a mixture of R-pyridine-2-carboxylic acid N'-[2-(tert-butyl-dimethylsilyloxy)-propionyl]-hydrazide (600 gm) and Lawesson's reagent (448 gm) in THF (1800 ml) was refluxed for 16 hr under stirring. The reaction mixture was cooled to 25° C. and poured in aqueous sodiumbicarbonate solution (prepared from sodiumbicarbonate 366 gm and water 3000 ml) under stirring. The mixture was extracted with ethyl acetate (2000 ml×2). The combined organic layer was washed with water (2000 ml) and dried over sodium sulfate. Organic layer was evaporated under vacuum to provide title compound in 570 gm quantity in 95.3% yield as a syrup.

Mass (m/z) (M+1): 322.2, Purity by GC: 89.68% (RT 28.80)

Step-4: Preparation of R-1-(5-pyridin-2-yl-[1,3,4]thiadiazol-2-yl)-ethanol

To a mixture of R-2-{5-[1-(tert-butyl-dimethylsilyloxy)-ethyl]-1,3,4-thiadiazol-2-yl}-pyridine (568 gm), in acetonitrile (1800 ml) was added 2N aqueous hydrochloric acid (1800 ml) in one lot under stirring at 32° C. It was stirred over a period of 19 hr. The reaction mixture was poured in aqueous sodium carbonate solution (prepared by dissolving 560 gm of sodium carbonate in 1800 ml water) under stirring. The organic layer was separated. Aqueous layer was extracted with ethyl acetate (1000 ml×2). Combined organic layer was dried over sodium sulfate and concentrated to afford semi-solid in 400 gm quantity, which was purified by stirring in ethyl acetate (400 ml) and filtering resultant suspension, to provide title compound in 230 gm quantity in 63% yield as a solid.

Mass: m/z: 208 (M+1), Chemical purity: 99.83% (RT 14.82).

Step-5: Preparation of R-5-(1-nosyloxyethyl)-1,3,4-thiadiazol-2-yl-pyridine

To a mixture of R-1-(5-pyridin-2-yl-[1,3,4]thiadiazol-2-yl)-ethanol (228 gm), and triethylamine (230 ml) in dichloromethane (2000 ml) was added a solution of p-nitrophenyl-sulfonyl chloride (246 gm) dissolved in dichloromethane (500 ml) at 10° C. under stirring. The reaction mixture was stirred over a period of 2 h at 25° C. To the resulting yellow suspension, was added water (2000 ml) and dichloromethane (1000 ml) under stirring. The layers were separated and dried over sodium sulfate to provide a brown coloured solid in 514 gm quantity. The solid was stirred in a mixture of dichloromethane (250 ml) and diethyl ether (500 ml) at 30° C. The suspension was filtered at suction and washed with a mixture of dichloromethane:diethyl ether mixture (1:2 ratio, 300 ml). the solid was dried under vacuum to provide title compound in 410 gm quantity in 95% yield as a pale yellow solid.

Mass: m/z: (M+1) 393.0, Chemical Purity=97.67%, Chiral Purity=99.97%, $[\alpha]_D^{25}$=+135.79 (c=0.5% in acetonitrile)

Preparation 11

(11S,21R)-3-decladinosyl-11,12-dideoxy-2-fluoro-6-O-methyl-3-oxo-2'-O-triethylsilyl-12,11-{oxycarbonyl-[E-(N-hydroxy)-carboxamidino]methylene}-erythromycin A

Step-1: Preparation of (11S,21R)-3-decladinosyl-11,12-dideoxy-6-O-methyl-2'-O-triethylsilyl-12,11-{oxycarbonyl-[E-(N-benzyloxy)-carboxamidino]methylene}-erythromycin A To a solution of triethylamine (4.5 ml) in THF (170 ml) was added benzyl bromide (3.1 ml) via syringe at 30° C. It was stirred for 4 hours to provide a suspension. To the suspension was added (11S,21R)-3-decladinosyl-11,12-dideoxy-6-O-methyl-2'-O-triethylsilyl-12,11-{oxycarbonyl-[E-(N-hydroxy)-carboxamidino]methylene}-erythromycin A (17 g) as in one lot, followed by freshly powdered potassium hydroxide (1.57 g) in one lot. The reaction mixture was stirred for 3.5 h at 30° C. After TLC check the reaction was filtered at suction to remove salts. The filtrate was concentrated to complete dryness under vacuum below 45° C. to provide a 19 gm powder. It was stirred with chilled water (180 ml) for 5 h to provide a suspension. The solid was filtered at suction and air dried to provide title compound in 17.8 gm (93.8%) quantity as a light yellow solid (HPLC purity 96.62%).

MS: m/z=876.2 (M+1)

Step-2: Preparation of (11S,21R)-3-decladinosyl-11, 12-dideoxy-6-O-methyl-3-oxo-2'-O-triethylsilyl-12, 11-{oxycarbonyl-[E-(N-benzyloxy)-carboxamidino] methylene}-erythromycin A To the stirred solution of N-chlorosuccinimide (7.5 gm) in dichloromethane (75 ml) was added dimethyl sulfide (4.8 ml) at −15° C. The reaction mixture was stirred at −15° C. for 1 h. The step-1 product (17 gm) dissolved in dichloromethane (35 ml) was added to the reaction mixture at −40° C. The resulting reaction mixture was stirred at −40° C. temperature for 3 hr. Triethyl amine (6.8 ml) was added and stirred for overnight at 30° C. The reaction mixture diluted with ethyl acetate (220 ml) and washed with 0.5M aqueous sodium hydroxide solution (100 ml). The organic layer was separated and washed with brine solution. The organic layer was concentrated under vacuum to dryness to provide a 14 gm powder. The powder was stirred with chilled water (140 ml) for 5 h to provide a suspension. The suspension was filtered and was air dried to provide 14 gm pale yellow powder. The powder was stirred in methanol (42 ml) and filtered to provide 11.2 gm (66%) title compound as a white solid (HPLC purity 97.3%).

MS=(m/z)=874.2 (M+1)

Step-3: Preparation of (11S,21R)-3-decladinosyl-11, 12-dideoxy-2-fluoro-6-O-methyl-3-oxo-2'-O-triethylsilyl-12,11-{oxycarbonyl-[E-(N-benzyloxy)-carboxamidino]methylene}-erythromycin A To a solution of step-2 product (11 gm) in DMF (110 ml) was added lithium tert-butoxide (1.51 gm) as a solid in lots over a period of 30 minutes at −15° C. N-Fluorodibenzene-sulfnimide (NFSI, 4.19 gm) dissolved in DMF (40 ml) over a period of 30 minutes at −15° C. The reaction mixture was stirred for 0.5 h at −15° C. To the reaction mixture was added aqueous ammonium chloride solution (13 gm in 750 ml water) under stirring. The suspension was stirred for 0.5 h and was filtered at suction. The solid was dissolved in ethyl acetate (200 ml) and was washed with 0.5 M aqueous sodium hydroxide solution (50 ml). The organic layer separated and evaporated under vacuum to dryness to provide title compound as a solid in 10.3 gm (91.8%) quantity (HPLC purity 90.12%).

MS: m/z=892.2 (M+1)

Step-4: Preparation of (11S,21R)-3-decladinosyl-11, 12-dideoxy-2-fluoro-6-O-methyl-3-oxo-2'-O-triethylsilyl-12,11-{oxycarbonyl-[E-(N-hydroxy)-carboxamidino]methylene}-erythromycin A To a solution of step-3 product (9 gm) in 1:1 mixture of methanol: ethyl acetate mixture (180 ml) was added a mixture of 10% Pd on carbon (1.35 gm) and 20% Pd(OH)$_2$ (1.35 gm). The reaction mixture was subjected to hydrogenolysis in shaker at 70 psi hydrogen pressure for 48 h. As the TLC showed completion of reaction, it was filtered at suction over a bed of celite. The filtrate was evaporated under vacuum to dryness to provide 6.7 gm solid, which was stirred with n-pentane (120 ml) and filtered to provide title compound in 5.8 gm quantity (71.6%) as a white solid (HPLC purity 90.39%).

MS: m/z=802.1 (M+1)

General Procedure for the Preparation of Compounds of Formula (I), wherein $R_3$ is H

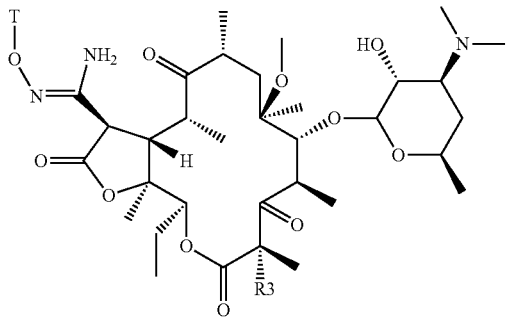

$R_3 = H$;
T is as defined

General Procedure for the Preparation of Compounds of Formula (I), wherein $R_3$ is F

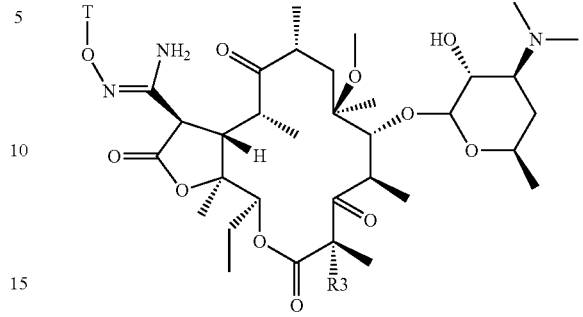

$R_3 = F$;
T is as defined (11S,21R)- 3-decladinosyl-11,12-dideoxy-6-O-methyl-2'-O-triethylsilyl-12,11-{oxycarbonyl-[E-(N-hydroxy)-carboxamidino]methylene}-erythromycin A in toluene is reacted in the presence of base such as potassium hydride or potassium tertbutoxide and a phase transfer catalyst 18-crown-6 ether, with racemic or enantiomerically pure appropriate side chain of formula Z—C*H(R1)-P-Q where Z is bromide, or appropriate ester such as mesylate, tosylate or nosylate and $R_1$, P and Q are as described, at a temperature ranging from 25° C. to 35° C. to provide corresponding etherified compound as (11S,21R)-3-decladinosyl-11,12-dideoxy-6-O-methyl-2'-O-triethylsilyl-12,11-{oxycarbonyl-[E-(N-hetero aryl-heteroaryl-(RS) or (R) or (S)-alkoxy)-carboxamidino]methylene}-erythromycin-A.

The compound (11S,21R)- 3-decladinosyl-11,12-dideoxy-6-O-methyl-2'-O-triethylsilyl-12,11-{oxycarbonyl-[E-(N-heteroaryl-heteroaryl-(RS) or (R) or (S)-alkoxy)-carboxamidino]methylene}-erythromycin-A is oxidized by treating under standard condition using either Corey-Kim oxidizing species (made from NCS and DMS) in dichloromethane at a temperature ranging from −50° C. to 10° C. to provide corresponding oxidized compound as (11S,21R)-3-decladinosyl-11,12-dideoxy-6-O-methyl-3-oxo-2'-O-triethylsilyl-12,11-{oxycarbonyl-[E-(N-heteroaryl-heteroaryl-(RS) or (R) or (S)-alkoxy)-carboxamidino]methylene}-erythromycin-A.

The compound (11S,21R)- 3-decladinosyl-11,12-dideoxy-6-O-methyl-3-oxo-2'-O-triethylsilyl-12,11-{oxycarbonyl-[E-(N-heteroaryl-heteroaryl-(RS) or (R) or (S)-alkoxy)-carboxamidino]methylene}-erythromycin-A is reacted with silyl deprotecting agent such as pyridine-hydrogenfluoride, or aqueous hydrochloric acid, in acetonitrile at a temperature ranging from 20° C. to 35° C. to provide the ketolide compound of formula (I) where $R_3$ is H.

For the compounds of formula (I) obtained as above, where Q bears a substituent such as t-butoxycarbonylamino, the t-butoxycarbonyl group was deprotected by stirring it with trifluoroacetic acid in acetonitrile at 0° C. to 35° C. for 1 hr followed by purification to provide ketolide compound of formula (I).

For the compounds of formula (I) obtained as above, where Q bears a substituent such as O-benzyloxy, the benzyl group was deprotected by stirring it with 10% palladium on carbon under hydrogen pressure in methanol at 25° C. to 35° C. followed by purification to provide ketolide compound of formula (I).

(11S,21R)- 3-decladinosyl-11,12-dideoxy-2-fluoro-6-O-methyl-3-oxo-2'-O-triethylsilyl-12,11-{oxycarbonyl-[E-(N-hydroxy)-carboxamidino]methylene}-erythromycin A in toluene is reacted in the presence of suitable base such as potassium hydride or potassium tertbutoxide and a phase transfer catalyst 18-crown-6 ether, with racemic or enantiomerically pure appropriate side chain of formula Z—C*H(R1)-P-Q where Z is mesylate or nosylate ester and $R_1$, P and Q are as described, at a temperature ranging from 25° C. to 35° C. to provide corresponding etherified compound as (11S,21R)- 3-decladinosyl-11,12-dideoxy-2-fluoro-6-O-methyl-3-oxo-2'-O-triethylsilyl-12,11-{oxycarbonyl-[E-(N-heteroaryl-heteroaryl-(RS) or (R) or (S)-alkoxy)-carboxamidino]methylene}-erythromycin-A.

The compound (11S,21R)- 3-decladinosyl-11,12-dideoxy-2-fluoro-6-O-methyl-3-oxo-2'-O-triethylsilyl-12,11-{oxycarbonyl-[E-(N-heteroaryl-heteroaryl-(RS) or (R) or (S)-alkoxy)-carboxamidino]methylene}-erythromycin-A is reacted with silyl deprotecting agent such as pyridine-hydrogenfluoride or aqueous hydrochloric acid, in acetonitrile at a temperature ranging from 20° C. to 35° C. to provide the ketolide compound of formula (I) where $R_3$ is F.

For the compounds of formula (I) obtained as above, where Q bears a substituent such as t-butoxycarbonylamino, the t-butoxycarbonyl group was deprotected by stirring it with trifluoroacetic acid in acetonitrile at 0° C. to 35° C. for 1 hr followed by purification to provide ketolide compound of formula (I).

For the compounds of Formula (I) obtained as above, where Q bears a substituent such as O-benzyloxy, the benzyl group was deprotected by stirring it with 10% palladium on carbon under hydrogen pressure in methanol at 25° C. to 35° C. followed by purification to provide ketolide compound of formula (I).

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

(11S,21R)-3-Decladinosyl-11,12-dideoxy-2-fluoro-6-O-methyl-3-oxo-12,11-{oxycarbonyl-[E-N-(5-pyrimidin-2-yl-isoxazol-3-yl)-methoxy]-carboxamidino]methylene}-erythromycin A Step-1: Preparation of (11S,21R)-3-decladinosyl-11,12-dideoxy-2-fluoro-6-O-methyl-3-oxo-2'-O-triethylsilyl-12,11-{oxycarbonyl-[E-N-(5-pyrimidin-2-yl-isoxazol-3-yl)-methoxy]-carboxamidino]methylene}-erythromycin A To the stirred suspension of potassium hydride (1.46 gm, 30% suspension in mineral oil), followed by 18-crown-6-ether (0.660 gm)) in toluene (300 ml) was added (11S,21R)-3-decladinosyl-11,12-dideoxy-2-fluoro-6-O-methyl-3-oxo-2'-O-triethylsilyl-12,11-{oxycarbonyl-[E-(N-hydroxy)-carboxamidino]methylene}-erythromycin A (8 g) at 30° C. It was stirred for 5 minutes. To the reaction mixture, 2-(3-bromomethyl-isoxazol-5-yl)-pyrimidine (2.9 gm) was added. The reaction mixture was stirred for 30 minutes. It was quenched by pouring it in aqueous saturated ammonium chloride solution (50 ml) under stirring. The mixture was extracted with ethyl acetate (250 ml×2). Combined organic layer was dried over Na$_2$SO$_4$ and evaporated under vacuum to provide a crude mass, which was purified by using silica gel column chromatography (12% to 15% acetone in hexane) to provide title compound as step-1 product in 5 gm quantity in 53% yield as a off white solid.

MS: m/z: 961.4 (M+1)

Step-2: Preparation of (11S,21R)-3-decladinosyl-11,12-dideoxy-2-fluoro-6-O-methyl-3-oxo-12,11-{oxycarbonyl-[E-N-(5-pyrimidin-2-yl-isoxazol-3-yl)-methoxy]-carboxamidino]methylene}-erythromycin A A mixture of (11S,21R)-3-decladinosyl-11,12-dideoxy-2-fluoro-6-O-methyl-3-oxo-2'-O- triethylsilyl-12,11-{oxycarbonyl-[E-N-(5-pyrimidin-2-yl-isoxazol-3-yl)-methoxy]-carboxamidino]methylene}-erythromycin A (5 gm) obtained as above in step-1, and 70% HF-pyridine solution (0.225 ml) in acetonitrile (50 ml) was stirred at 30° C. for 2 hr under N$_2$ atmosphere. After completion of reaction, reaction was quenched with addition of aqueous sodium bicarbonate solution (50 ml). The mixture was evaporated under vacuum to half of the volume, and water (20 ml) was added to the residue to provide a suspension which was filtered under suction. The solid was washed with water, followed by ether to afford title compound of example-1 in 3.1 gm quantity as a white solid in 71% yield.

MS: m/z: 847.1 (M+1)

Following examples were prepared by using the procedure described in Example-1 as above and utilizing the respective side chains as shown:

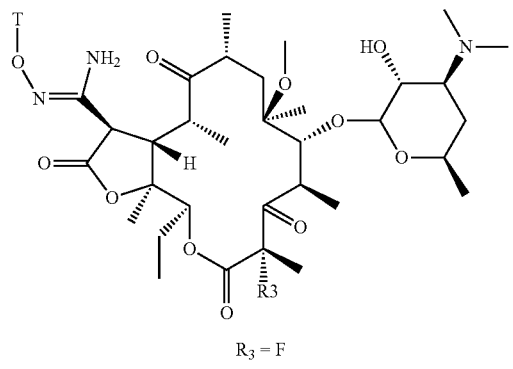

Formula I

R$_3$ = F

| Example No. | T | Side chain used for coupling | Mp (° C.) | Mass (M + 1) |
|---|---|---|---|---|
| 2 | | 2-(5-Bromomethyl-isoxazol-3-yl)-pyrimidine | 156-158 | 847.9 |
| 3 | | 3-(2-Bromomethyl-pyrimidin-5-yl)-isoxazole | 196-197 | 847.9 |
| 4 | | 2-tert-Butyloxycarbonylamino 6-(3-bromomethyl-isoxazol-5-yl)-pyridine | 215-217 | 861.9 |

-continued

| Example No. | T | Side chain used for coupling | Mp (° C.) | Mass (M + 1) |
| --- | --- | --- | --- | --- |
| 5 | (3-pyridin-2-yl-isoxazol-5-yl with CH2 linker) | 2-(3-Bromomethyl-isoxazol-5-yl)-pyridine | 193-194 | 846.9 |
| 6 | (5-(6-aminopyridin-2-yl)-1,3,4-thiadiazol-2-yl with CH2 linker) | 2-tert-butyloxycarbonylamino-6-(5-Bromomethyl-1,3,4-thiadiazol-2-yl)-pyridine | 230-232 | 879.0 |
| 7 | (5-pyrimidin-2-yl-1,3,4-thiadiazol-2-yl with CH2 linker) | 2-(5-Bromomethyl-1,3,4-thiadiazol-2-yl)-pyrimidine | 192-194 | 864.9 |
| 8 | (5-pyrazin-2-yl-1,3,4-thiadiazol-2-yl with CH2 linker) | 2-(5-Bromomethyl-1,3,4-thiadiazol-2-yl)-pyrazine | 223-225 | 864.9 |
| 9 | (5-(6-aminopyridin-3-yl)-1,3,4-thiadiazol-2-yl with CH2 linker) | 2-tert-Butyloxycarbonylamino-5-(5-bromomethyl-1,3,4-thiadiazol-2-yl)-pyridine | 202-204 | 879.0 |
| 10 | (5-pyridin-2-yl-1,3,4-thiadiazol-2-yl with CH2 linker) | 2-(5-Bromomethyl-1,3,4-thiadiazol-2-yl)-pyridine | 207-210 | 864.0 |
| 11 | (3-pyrazin-2-yl-isoxazol-5-yl with CH2 linker) | 2-(3-Bromomethyl-isoxazol-5-yl)-pyrazine | 196-197 | 847.0 |

| Example No. | T | Side chain used for coupling | Mp (° C.) | Mass (M + 1) |
|---|---|---|---|---|
| 12 | [thiadiazole-pyrazine-NH2 structure] | 2-tert-Butyloxycarbonylamino-5-(5-bromomethyl-1,3,4-thiadiazol-2-yl)-pyrazine | 178-180 | 879.0 |
| 13 | [thiadiazole-pyrimidine-NH2 structure] | 6-tert-Butyloxy carbonylamino-2-[5-bromomethyl-1,3,4-thiadiazol-2-yl]-pyrimidine | 210-214 | 879.0 |
| 14 | [pyrimidine-pyrazine structure] | 2-(2-Bromomethyl-pyrimidin-5-yl)-pyrazine | 169-171 | 858.1 |
| 15 | [thiadiazole-benzene-NH2 structure] | 3-tert-butyloxy carbonylamino-1-(5-bromomethyl-1,3,4-thiadiazol-2-yl)-benzene | 180-185 | 878.1 |
| 16 | [bipyridine-NH2 structure] | 2-di-(tert-butyloxy carbonyl)-amino-6-(2-bromomethyl-pyridin-6-yl)-pyridine. | 150-152 | 872.0 |
| 17 | [isoxazole-pyrimidine-NH2 structure] | 6-tert-butyloxy carbonylamino-2-(3-bromomethyl-isoxazol-5-yl)-pyrimidine. | — | 862.1 |

Example 18

(11S,21R)-3-decladinosyl-11,12-dideoxy-2-fluoro-6-O-methyl-3-oxo-12,11-{oxycarbonyl-[E-N-[1-(5-pyridin-2-yl-1,3,4-thiadiazol-2-yl)-(S)-ethoxy]-carboxamidino]methylene}-erythromycin A Step-1: Preparation of (11S,21R)-3-decladinosyl-11,12-dideoxy-2-fluoro-6-O-methyl-3-oxo-2'-O-triethylsilyl-12,11-{oxycarbonyl-[E-N-[1-(5-pyridin-2-yl-1,3,4-thiadiazol-2-yl)-(S)-ethoxy]-carboxamidino]methylene}-erythromycin A To the stirred solution of (11S,21R)-3-decladinosyl-11,12-dideoxy-2-fluoro-6-O-methyl-3-oxo-2'-O-triethylsilyl-12,11-{oxycarbonyl-[E-(N-hydroxy)-carboxamidino]methylene}-erythromycin A (3.5 g) in toluene (50 ml) was added potassium hydride (0.07 g, 30% suspension in mineral oil), 18-crown-6-ether (0.2 g) followed by (R)-2-(5-(1-nosyloxy-ethyl)-1,3,4-thiadiazol-2-yl)-pyridine (1.5 gm) at 0° C. temperature. The reaction mixture was stirred for 4 h. It was quenched by pouring it in aqueous saturated ammonium chloride solution (50 ml). The mixture was extracted with ethyl acetate (100 ml×2). Combined organic layer was dried over $Na_2SO_4$ evaporated under vacuum to provide a crude compound to provide step-1 product in 4.0 gm quantity (92%) as a syrup which was used as such for the next reaction.

MS: m/z: 991.3 (M+1)

Step-2: Preparation of (11S,21R)-3-decladinosyl-11,12-dideoxy-2-fluoro-6-O-methyl-3-oxo-12,11-{oxycarbonyl-[E-N-[1-(5-pyridin-2-yl-1,3,4-thiadiazol-2-yl)-(S)-ethoxy]-carboxamidino]methylene}-erythromycin A The mixture of step-1 product (11S,21R)-3-decladinosyl-11,12-dideoxy-2-fluoro-6-O-methyl-3-oxo-2'-O-triethylsilyl-12,11-{oxycarbonyl-[E-N-[1-(5-pyridin-2-yl-1,3,4-thiadiazol-2-yl)-(S)-ethoxy]-carboxamidino]methylene}-erythromycin A (4 g), and 70% HF-pyridine solution (0.400 ml) dissolved in acetonitrile (40 ml) was stirred at 30° C. for 2 hr under N₂ atmosphere. After completion of reaction, reaction was quenched with addition of aqueous sodium bicarbonate solution (50 ml). The mixture was evaporated under vacuum to half of the volume. Water (20 ml) was added to the crude product to provide a suspension, which was filtered under suction. The solid was washed water followed by ether to afford crude compound, which was purified by recrystallization using ethyl acetate and methanol (1:4) to provide 2-fluoro-ketolide compound of invention in 1.3 gm (37%) quantity was a white solid.

Retention time 21.29 (HPLC purity 91.66%), M.p.=133-135° C., MS=(m/z)=877.1 (M+1)

Following examples were prepared by using the procedure describes in example 18 and utilizing corresponding p-nitrophenylsulfonyl (nosyl) ester analogues of respective side chains:

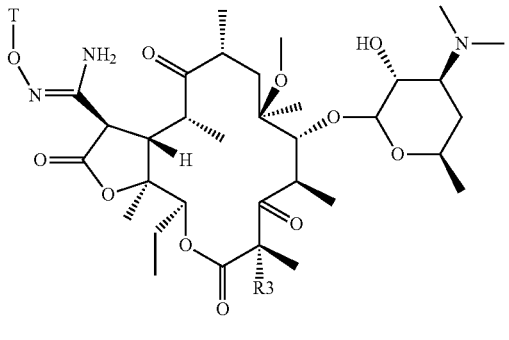

$R_3 = F$

| Example No | T | Side chain used for coupling | Mp (° C.) | Mass (M + 1) |
|---|---|---|---|---|
| 19 | H₃C—[thiadiazole-pyridine-NH₂] | (S)-2-tert-Butyloxycarbonylamino-6-[5-(1-methanesulfonyloxy-ethyl)-1,3,4-thiadiazol-2-yl]-pyridine | 208-210 | 893.1 |
| 20 | H₃C—[thiadiazole-pyridine-NH₂] | (R)-2-tert-Butyloxycarbonylamino-6-[5-(1-methanesulfonyloxy-ethyl)-1,3,4-thiadiazol-2-yl]-pyridine | 230-232 | 893.1 |
| 21 | H₃C—[thiadiazole-pyrimidine] | (R)-2-[5-(1-methanesulfonyloxy-ethyl)-1,3,4-thiadiazol-2-yl]-pyrimidine | 168-170 | 879.1 |
| 22 | H₃C—[thiadiazole-pyrazine] | (R)-[5-(1-nosyloxy-ethyl)-1,3,4-thiadiazol-2-yl]-pyrazine | 232.234 | 879.1 |
| 23 | H₃C—[isoxazole-pyrimidine] | (R)-[3-(1-nosyloxy-ethyl)-isoxazol-5-yl]-pyrimidine | 170-172 | 861.1 |

-continued

| Example No | T | Side chain used for coupling | Mp (° C.) | Mass (M + 1) |
|---|---|---|---|---|
| 24 | 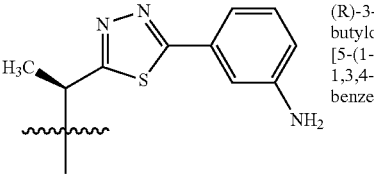 | (R)-3-tert-butyloxycarbonylamino-[5-(1-nosyloxy-ethyl)-1,3,4-thiadiazol-2-yl]-benzene | 244-245 | 892.0 |
| 25 | 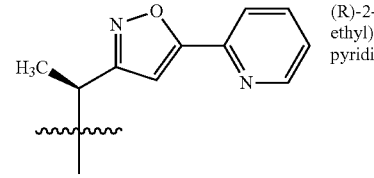 | (R)-2-[3-(1-nosyloxy-ethyl)-isoxazol-5-yl]-pyridine | 194-196 | 860.1 |
| 26 | 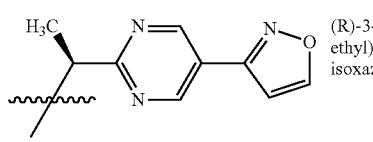 | (R)-3-[2-(1-nosyloxy-ethyl)-pyrimidin-5-yl]-isoxazole | 193-195 | 861.1 |
| 27 | 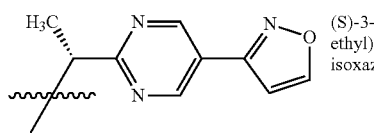 | (S)-3-[2-(1-nosyloxy-ethyl)-pyrimidin-5-yl]-isoxazole | 152-154 | 861.1 |
| 28 | 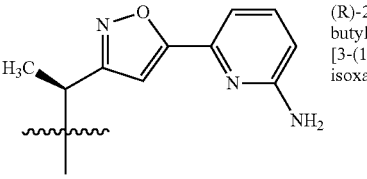 | (R)-2-tert-butyloxycarbonylamino-6-[3-(1-nosyloxy-ethyl)-isoxazol-5-yl]-pyridine | 205-207 | 875.1 |
| 29 | 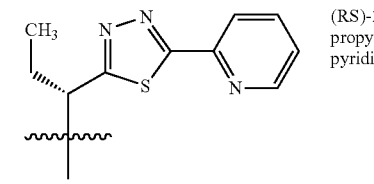 | (RS)-2-[5-(1-nosyloxy-propyl)-thiadiazol-2-yl]-pyridine | 208-210 | 891.3 |
| 30 | 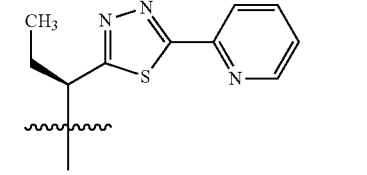 [SMILES: *[C@@H](CC)c1nnc(-c2ccccn2)s1] |  | 210-212 | 891.3 |

Example 31

(11S,21R)-3-decladinosyl-11,12-dideoxy-6-O-methyl-3-oxo-12,11-{oxycarbonyl-[E-N-[1-(5-pyridin-2-yl-1,3,4-thiadiazol-2-yl)-(RS)-ethoxy]-carboxamidino]methylene}-erythromycin A

Step-1: Preparation of (11S,21R)-3-decladinosyl-11,12-dideoxy-6-O-methyl-2'-O-triethylsilyl-12,11-{oxycarbonyl-[E-N-[1-(5-pyridin-2-yl-1,3,4-thiadiazol-2-yl)-(RS)-ethoxy]-carboxamidino]methylene}-erythromycin A To the stirred solution of (11S,21R)- 3-decladinosyl-11,12-dideoxy-6-O-methyl-2'-O-triethylsilyl-12,11-{oxycarbonyl-[E-(N-hydroxy)-carboxamidino]methylene}-erythromycin A (1.5 g) in toluene (20 ml) was added potassium hydride (0.3 g, 30% suspension in mineral oil), 18-crown-6-ether (0.1 g) followed by (RS)-2-[5-(1-bromo-ethyl)-1,3,4-thiadiazol-2-yl]-pyridine (0.7 gm) at 30° C. temperature. The reaction mixture was stirred for 30 minutes. It was quenched by pouring it in aqueous saturated ammonium chloride solution (10 ml). The mixture was extracted with ethyl acetate (100 ml×2). Combined organic layer was dried over $Na_2SO_4$ evaporated under vacuum to provide a crude mass which was purified by using silica gel column chromatography (15% Acetone:Hexane) to provide step-1 product in 1.5 gm quantity (80%) as a off white solid.

MS=(m/z)=975.3 (M)

Step-2: Preparation of (11S,21R)-3-decladinosyl-11,12-dideoxy-6-O-methyl-3-oxo-2'-O-triethylsilyl-12,11-{oxycarbonyl-[E-N-[1-(5-pyridin-2-yl-1,3,4-thiadiazol-2-yl)-(RS)-ethoxy]-carboxamidino]methylene}-erythromycin A To the stirred solution of N-chlorosuccinimide (1.5 gm) in dichloromethane (75 ml) was added dimethyl sulfide (2 ml) at −10° C. The reaction mixture was stirred at −10° C. for 30 min. The step-1 product (1.5 gm) dissolved in dichloromethane (25 ml) was added to the reaction mixture at −40° C. The resulting reaction mixture was stirred at −40° C. temperature for 3 hr. Triethyl amine (5 ml) was added and stirred for overnight at 30° C. The reaction mixture was poured in aqueous saturated sodium bicarbonate solution (20 ml) and the mixture was extracted with dichloromethane (50 ml×2). The combined organic layer was dried over $Na_2SO_4$ and evaporated under vacuum to provide crude mass which was purified by using silica gel column chromatography (12% Acetone:Hexane) to provide step-2 product as a semi solid in 1.2 gm quantity (80%).

MS=(m/z)=973.4 (M)

Step-3: Preparation of (11S,21R)-3-decladinosyl-11,12-dideoxy-6-O-methyl-3-oxo-12,11-{oxycarbonyl-[E-N-[1-(5-pyridin-2-yl-1,3,4-thiadiazol-2-yl)-(RS)-ethoxy]-carboxamidino]methylene}-erythromycin A The mixture of step-2 product (1.2 gm) and 70% HF-pyridine solution (0.2 ml) in acetonitrile (20 ml) was stirred at 30° C. for 2 hr under $N_2$ atmosphere. Aqueous sodium bicarbonate solution was added (10 ml) and the mixture was extracted with dichloromethane (50 ml×2). Combined organic layer was dried over sodium sulfate and evaporated under vacuum to obtain crude mass. The crude mass was purified by using silica gel column chromatography (3% MeOH in $CHCl_3$) provided the title compound in 0.7 gm (59%) as a off white solid.

HPLC analysis showed mixture was in 44.97 (at 21.42 minutes) and 52.09 (at 25.25 minutes) proportion. M.p.=135-137° C., MS=(m/z)=859.3 (M⁺)

Example 32

Isolation of (11S,21R)-3-decladinosyl-11,12-dideoxy-6-O-methyl-3-oxo-12,11-{oxycarbonyl-[E-N-[1-(5-pyridin-2-yl-1,3,4-thiadiazol-2-yl)-(R)-ethoxy]-carboxamidino]methylene}-erythromycin A The 0.5 gm diastereomeric mixture obtained in example 31 was separated on preparative HPLC by using VMC-ODS-A column, 0.05 ammonium acetate buffer:acetonitrile (60:40 ratio) mobile phase adjusted to pH 7 by ammonia and acetic acid and flow rate 18 ml/min at UV detection at 215 nm The title compound was obtained with retention time 21.39 (HPLC purity 93.20%), M.p.=140-142° C., MS=(m/z)=860.1 (M+1)

Example 33

Isolation of (11S,21R)-3-decladinosyl-11,12-dideoxy-6-O-methyl-3-oxo-12,11-{oxycarbonyl-[E-N-[1-(5-pyridin-2-yl-1,3,4-thiadiazol-2-yl)-(S)-ethoxy]-carboxamidino]methylene}-erythromycin A Utilizing the same HPLC conditions, the title compound was obtained with retention time 25.11 (HPLC purity 98.52%), M.p.=128-130° C., MS=(m/z)=860.1 (M+1).

Following examples were prepared by using the procedure describes in example 31 and utilizing corresponding bromo analogues of respective side chains followed by preparative HPLC separation of diastereomeric mixture.

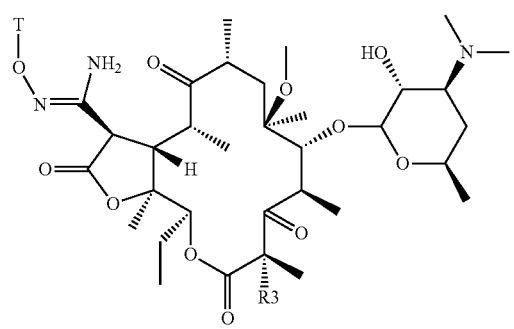

$R_3 = H$

| Example No | T | Side chain used for coupling | Mp (° C.) | Mass (M + 1) |
|---|---|---|---|---|
| 34 | (isoxazol-3-yl-pyridine with CH(CH₃) linker) | (RS)-2-[5-(1-bromo-ethyl)-isoxazol-3-yl]-pyridine | 220-221 | 842.9 |
| 35 | (isoxazol-3-yl-pyridine with CH(CH₃) linker) | | 216-218 | 842.9 |
| 36 | (isoxazol-3-yl-pyridine with CH(CH₃) linker) | | 118-120 | 842.9 |
| 37 | (isoxazol-5-yl-pyrimidine with CH(CH₃) linker) | (RS)-2-[3-(1-bromo-ethyl)-isoxazol-5-yl]-pyrimidine | 116-117 | 843.9 |
| 38 | (isoxazol-5-yl-pyrimidine with CH(CH₃) linker) | | 241-243 | 843.9 |
| 39 | (isoxazol-5-yl-pyrimidine with CH(CH₃) linker) | | 121-123 | 843.9 |
| 40 | (isoxazol-5-yl-pyridine with CH(CH₃) linker) | (RS)-2-[3-(1-bromo-ethyl)-isoxazol-5-yl]-pyridine | 210-212 | 842.9 |
| 41 | (isoxazol-5-yl-pyridine with CH(CH₃) linker) | | 138-140 | 842.9 |

-continued

| Example No | T | Side chain used for coupling | Mp (° C.) | Mass (M + 1) |
|---|---|---|---|---|
| 42 | (3-ethyl-isoxazol-5-yl)-pyridine with CH3 branch | (RS)-2-[3-(1-bromo-propyl)-isoxazol-5-yl]-pyridine | 112-114 | 857.0 |
| 43 | (3-ethyl-isoxazol-5-yl)-pyridine with CH3 branch | | 174-176 | 857.0 |
| 44 | 5-(1,3,4-thiadiazol-2-yl)-pyrimidine with H3C branch | (RS)-[5-(1-bromo-ethyl)-1,3,4-thiadiazol-2-yl]-pyrimidine | 173-175 | 861.1 |
| 45 | 5-(1,3,4-thiadiazol-2-yl)-pyrimidine with H3C branch | | 204-206 | 861.1 |
| 46 | 5-(1,3,4-thiadiazol-2-yl)-pyrimidine with H3C branch | | 170-172 | 861.1 |
| 47 | 5-(1,3,4-thiadiazol-2-yl)-6-amino-pyridine with H3C branch | (RS)-2-tert-butyloxycarbonylamino-5-[5-(1-bromo-ethyl)-1,3,4-thiadiazol-2-yl]-pyridine | 164-166 | 875.0 |
| 48 | 5-(1,3,4-thiadiazol-2-yl)-6-amino-pyridine with H3C branch | | 170-172 | 875.1 |
| 49 | 5-(1,3,4-thiadiazol-2-yl)-6-amino-pyridine with H3C branch | | 138-140 | 875.1 |

| Example No | T | Side chain used for coupling | Mp (° C.) | Mass (M + 1) |
|---|---|---|---|---|
| 50 | H₃C-CH(-)- attached to 2-(1,3,4-thiadiazol-5-yl)pyrazine (wedge/racemic) | (RS)-[5-(1-bromo-ethyl)-1,3,4-thiadiazol-2-yl]-pyrazine | 206-208 | 861.1 |
| 51 | H₃C-CH(-)- attached to 2-(1,3,4-thiadiazol-5-yl)pyrazine (hashed wedge) | | 178-180 | 861.1 |
| 52 | H₃C-CH(-)- attached to 2-(1,3,4-thiadiazol-5-yl)pyrazine (solid wedge) | | 206-208 | 861.1 |
| 53 | H₃C-CH(-)- attached to 2-(1,3,4-oxadiazol-5-yl)pyridine | (RS)-2-[5-(1-bromo-ethyl)-1,3,4-oxadiazol-2-yl]-pyridine | 120-122 | 843.1 |

Alternate Method for Preparation of Example-33

(11S,21R)-3-decladinosyl-11,12-dideoxy-6-O-methyl-3-oxo-12,11-{oxycarbonyl-[E-N-[1-(5-pyridin-2-yl-1,3,4-thiadiazol-2-yl)-(S)-ethoxy]-carboxamidino]methylene}-erythromycin A Step-1: Preparation of (11S,21R)-3-decladinosyl-11, 12-dideoxy-6-O-methyl-2'-O-triethylsilyl-12,11-{oxycarbonyl-[E-N-[1-(5-pyridin-2-yl-1,3,4-thiadiazol-2-yl)-(S)-ethoxy]-carboxamidino]methylene}-erythromycin A To the stirred solution of (11S,21R)- 3-decladinosyl-11, 12-dideoxy-6-O-methyl-2'-O-triethylsilyl-12,11-{oxycarbonyl-[E-(N-hydroxy)-carboxamidino]methylene}-erythromycin A (35.0 g) in toluene (350 ml) was sequentially added 18-crown-6-ether (1.96 g) followed by potassium t-butoxide (5.6 g) at 30° C. The blue coloured suspension was stirred for 10 minutes to provide a clear solution. To this solution, was added (R)-2-[5-(1-nosyloxy-ethyl)-1,3,4-thiadiazol-2-yl]-pyridine (19.4 gm, prepared from methyl-D-lactate) at 30° C. temperature as a solid followed by toluene (70 ml). The reaction mixture was stirred for 30 minutes at 30° C. The reaction mixture was quenched with 3% aqueous ammonium chloride solution (200 ml) as TLC showed complete conversion of starting material. (TLC system: hexane:ethyl acetate: diethylamine 5:5:2). The mixture was extracted with ethyl acetate (250 ml×2). Combined organic layer was washed with brine and dried over Na₂SO₄, evaporated under vacuum to provide a crude mass as yellow foam in 47 gm quantity, which was used as it is, for the next reaction.

Mass (M+)=975.4, HPLC=Chemical purity=73.7%, diastereomeric purity=99.42%.

Step-2: Preparation of (11S,21R)-3-decladinosyl-11, 12-dideoxy-6-O-methyl-3-oxo-2'-O-triethylsilyl-12, 11-{oxycarbonyl-[E-N-[1-(5-pyridin-2-yl-1,3,4-thiadiazol-2-yl)-(S)-ethoxy]-carboxamidino]methylene}-erythromycin A To the stirred solution of N-chlorosuccinimide (18.02 gm) in dichloromethane (180 ml) was added dimethyl sulfide (11.2 ml) at −20° C. to −15° C. The reaction mixture was stirred at −20° C.-15° C. for 30 min. The step-1 product (46.7 gm) dissolved in dichloromethane (300 ml) was added to the reaction mixture at −50° C. to −40° C. via addition funnel. The resulting reaction mixture was stirred at −40° C.-35° C. temperature for 3 hr. Triethyl amine (15.6 ml) was added at −40° C. and stirred until reaction mixture became clear at 30° C. To the reaction mixture was added under stirring ethyl acetate (880 ml) followed by 0.5 N aqueous sodium hydroxide solution (410 ml). The layers were separated after 30 minutes stirring. It was washed successively with water (410 ml) followed by brine solution (410 ml). The organic layer was dried over Na₂SO₄ and evaporated under vacuum to provide yellow foam in 49 gm quantity, which was subjected for the next reaction without any purification.

Mass (M+)=973.3, HPLC=Chemical purity=79.35%, Chiral purity=97.82%,

Step-3: Preparation of (11S,21R)-3-decladinosyl-11, 12-dideoxy-6-O-methyl-3-oxo-12,11-{oxycarbonyl-[E-N-[1-(5-pyridin-2-yl-1,3,4-thiadiazol-2-yl)-(S)-ethoxy]-carboxamidino]methylene}-erythromycin A The mixture of step-2 product (48 gm) and 2N aqueous hydrochloric acid (50 ml) in acetonitrile (125 ml) was stirred at 30° C. for 4 hr. To the clear red coloured solution was diluted with water (300 ml) and approximately 125 ml volume of solvents were removed below 55° C. under vacuum. The reaction mixture was cooled to 25° C. and extracted with ethyl acetate (150 ml). The aqueous layer was basified using aqueous potassium carbonate (100 ml, 18% w/v). The suspension was extracted with ethyl acetate (250 ml×2). Organic layer was washed with brine (150 ml) and concentrated under vacuum to provide light brown foam in 42 gm quantity. The crude foam was purified using warm (40° C.) ethanol (84 ml). The suspension was filtered at suction at 10° C. The solid cake was washed with chilled ethanol (10 ml×2). Drying of solid provided light yellow powder in 22.3 gm quantity in 52% yield after three steps.

Mass (M+)=859.3, HPLC purity 96.48%, M.p.=135°-137° C.

Following examples were prepared by using the procedure described above for the preparation of example 33, and utilizing corresponding either p-nitrophenylsulfonyl (nosyl) ester or methanesulfonyl ester analogues of respective side chains:

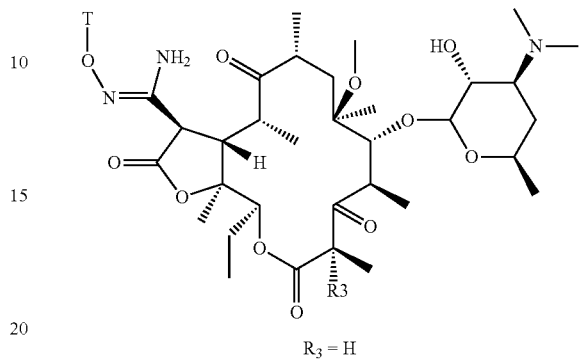

$R_3 = H$

| Example No | T | Side chain used for coupling | Mp (° C.) | Mass (M + 1) |
|---|---|---|---|---|
| 54 | | (R)-2-tert-butyloxy carbonylamino-6-[5-(1-methanesulfonyloxy-ethyl)-1,3,4-thiadiazol-2-yl]-pyridine | 197-200 | 875.0 |
| 55 | | (S)-2-tert-butyloxy carbonylamino-6-[5-(1-methanesulfonyloxy-ethyl)-1,3,4-thiadiazol-2-yl]-pyridine | 205-207 | 875.1 |
| 56 | | (R)-3-tert-butyloxycarbonylamino-[5-(1-nosyloxy-ethyl)-1,3,4-thiadiazol-2-yl]-benzene | 242-244 | 874.0 |
| 57 | | (R)-2-benzyloxy-6-[5-(1-nosyloxy-ethyl)-1,3,4-thiadiazol-2-yl]-pyridine | 168-170 | 876.0 |
| 58 | | (R)-3-[2-(1-nosyloxy-ethyl)-pyrimidin-5-yl]-isoxazole | 172-174 | 843.1 |

| Example No | T | Side chain used for coupling | Mp (° C.) | Mass (M + 1) |
|---|---|---|---|---|
| 59 |  | (R)-2-tert-butyloxycarbonylamino-6-[3-(1-nosyloxy-ethyl)-isoxazol-5-yl]-pyridine | 170-172 | 858.0 |
| 60 | 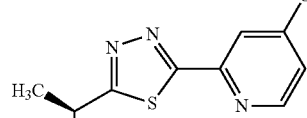 | (R)-4-benzyloxy-2-[5-(1-nosyloxy-ethyl)-isoxazol-2-yl]-pyridine | 150-152 | 876.0 |
| 61 | 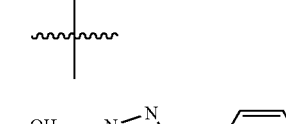 | (RS)-2-[5-(2-t-butyl dimethylsilyloxy-1-nosyloxy-ethyl)-1,3,4-thiadiazol-2-yl]-pyridine | 96-105 | 876.0 |
| 62 | 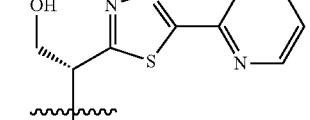 | | 98-108 | 876.0 |
| 63 | 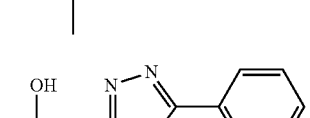 | (RS)-2-[5-(1-nosyloxy-propyl)-thiadiazol-2-yl]-pyridine | 140-144 | 874.0 |
| 64 | 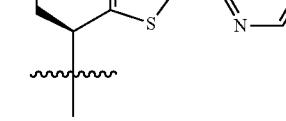 | | 206-208 | 874.0 |
| 65 | 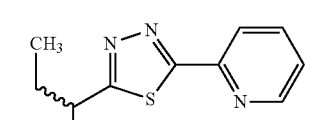 | | 186-188 | 874.0 |

Biological Protocols & Activities

In Vitro Evaluation of Compounds of the Invention

The antibacterial activity of compounds of the invention was evaluated by determining the minimal inhibitory concentration (MIC) according to standard CLSI agar dilution method. The media used for preculture and main culture were Tryptic Soya broth (Difco) and Mueller Hinton medium (Difco), respectively. The Mueller Hinton agar was supplemented with 5% sheep blood for streptococci and pneumococci, and with haemoglobin as well as NAD (nicotinamide adenine dinucleotide) for *Haemophilus influenzae*, respectively. Overnight cultures were diluted with buffered saline (pH 7.2) to the final cell density of $5 \times 10^6$-$10^7$ CFU/ml, and each bacterial suspension was applied with a replicator (Denley's multipoint inoculator, UK) onto a series of Mueller-Hinton agar plates containing antibacterial agents at various concentrations. Final inoculum was approximately $10^4$ CFU/spot. The plates were incubated for 18 hrs at 37° C. The MIC was defined as the lowest concentration of an antibacterial agent that inhibits the development of visible microbial growth on agar.

The compounds of the invention inhibited the growth of these bacteria with MICs in the range of about 0.007-0.25 mcg/ml (S pneumoniae sensitive strains, Telithromycin MIC 0.007-0.015 mcg/ml), 0.007-2.0 mcg/ml (S pneumoniae mef strains, Telithromycin MIC 0.015-1.0 mcg/ml), 0.007-2.0 mcg/ml (S pneumoniae ermb strains, Telithromycin MIC 0.007-0.50 mcg/ml), 0.12->16 mcg/ml (S pneumoniae 3773, a high level ermb strain, Telithromycin MIC 4.0 mcg/ml), 0.12->16 mcg/ml (S pyogene 3530, a high level ermb strain, MIC Telithromycin MIC 16.0 mcg/ml), 1-8 mcg/ml (H influenzae, Telithromycin MIC 4.0-8.0 mcg/ml).

In Vivo Evaluation of Compounds of the Invention

The in vivo efficacy of compounds of the invention was evaluated by determining $ED_{50}$ by oral administration of compounds to group of mice (6 mice/dose group) intraperitoneally infected with ($5 \times 10^7$-$1 \times 10^8$ CFU/mouse) S pneumoniae 3773. Two doses of compounds of the invention and Telithromycin were administered at 1 hour and 4 hour after infection. On day seven, percentage of animals surviving in various dose groups were employed to determine $ED_{50}$ (Dose protecting 50% of infected mice)

Some of the compounds of the invention showed superior oral efficacy against S. pneumoniae 3773 infection in mice ($ED_{50}$ 6.25-50 mg/Kg) compared to Telithromycin ($ED_{50}$ 75-100 mg/Kg)

The invention claimed is:

1. A compound of formula (I) or a pharmaceutically acceptable salt, solvate, hydrate, or a polymorph thereof,

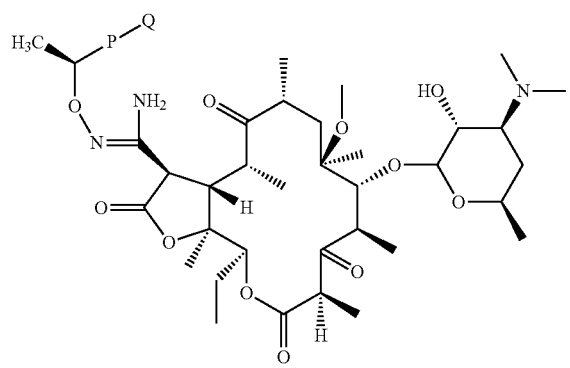

wherein,
P is thiadiazole;
Q is pyridine or pyrimidine, and;
P is attached to Q via carbon-carbon link.

2. A pharmaceutical composition comprising a compound of formula (I) according to claim 1 or a pharmaceutically acceptable salt, solvate, or a polymorph thereof, optionally, with one or more pharmaceutically acceptable excipient.

3. A pharmaceutical composition of claim 2 wherein the composition is administered parenterally or orally.

4. A method of treating infection caused by a microorganism in a subject, said method comprising administering to the subject in need thereof, a therapeutically effective amount of a compound of formula (I) according to claim 1 or a pharmaceutically acceptable salt, solvate, hydrate, or a polymorph thereof.

5. A method for prophylactic treatment of a subject, comprising administering to a subject at risk of infection caused by microorganism, a prophylactically effective amount of a compound of formula (I) according to claim 1 or a pharmaceutically acceptable salt, solvate, hydrate, or a polymorph thereof.

6. A method of treating infection caused by a microorganism in a subject, comprising administering to the subject in need thereof, a pharmaceutical composition according to claim 2.

7. A method for prophylactic treatment of a subject, comprising administering to a subject at risk of infection caused by microorganism, a pharmaceutical composition according to claim 2.

8. A method according to any one of the claims 4 to 7, wherein the microorganism is at least one microorganism selected from a bacteria, fungi, protozoa, yeast, mold, or mildew.

9. A compound, which is:

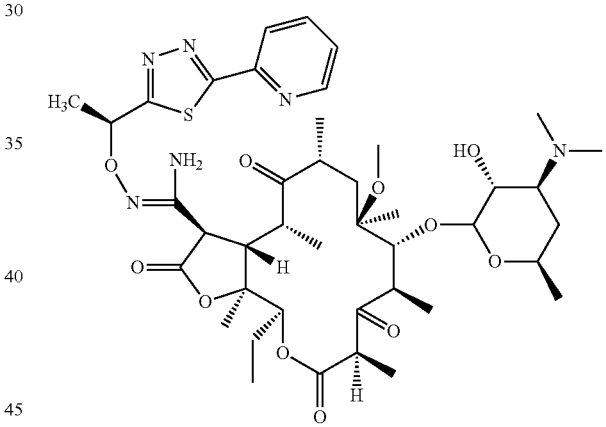

or a pharmaceutically acceptable salt, solvate, hydrate, or a polymorph thereof.

10. A pharmaceutical composition comprising a compound according to claim 9; or a pharmaceutically acceptable salt, solvate, or a polymorph thereof.

11. A method of treating infection caused by a microorganism in a subject, said method comprising administering to the subject in need thereof, a compound according to claim 9; or a pharmaceutically acceptable salt, solvate, hydrate, or a polymorph thereof.

12. A method for prophylactic treatment of a subject, comprising administering to a subject at a risk of infection caused by microorganism, a compound according to claim 9; or a pharmaceutically acceptable salt, solvate, hydrate, or a polymorph thereof.

13. A method of treating infection caused by a microorganism in a subject, said method comprising administering to the subject a pharmaceutical composition according to claim 10.

14. A compound which is:

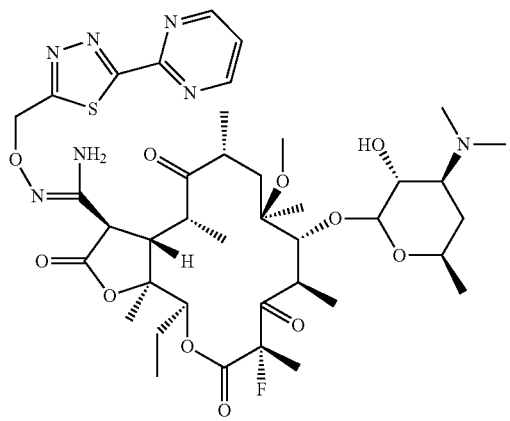 [SMILES: CC[C@@H]1OC(=O)[C@@](C)(F)C(=O)[C@H](C)[C@@H](OC2O[C@H](C)C[C@H](N(C)C)[C@H]2O)[C@](C)(OC)C[C@@H](C)C(=O)[C@H](C)[C@H]2[C@H](/C(N)=N/OCc3nnc(-c4ncccn4)s3)C(=O)O[C@@]21C]

or a pharmaceutically acceptable salt, solvate, hydrate, or a polymorph thereof.

15. A pharmaceutical composition comprising a compound according to claim 14; or a pharmaceutically acceptable salt, solvate, or a polymorph thereof.

16. A method of treating infection caused by a microorganism in a subject, said method comprising administering to the subject in need thereof, a compound according to claim 14; or a pharmaceutically acceptable salt, solvate, hydrate, or a polymorph thereof.

17. A method for prophylactic treatment of a subject, comprising administering to a subject at a risk of infection caused by microorganism, a compound according to claim 14; or a pharmaceutically acceptable salt, solvate, hydrate, or a polymorph thereof.

18. A method of treating infection caused by a microorganism in a subject, said method comprising administering to the subject a pharmaceutical composition according to claim 15.

* * * * *